United States Patent
Hayashi et al.

(10) Patent No.: US 10,100,061 B2
(45) Date of Patent: Oct. 16, 2018

(54) OXAZEPINE COMPOUND AND AGRICULTURAL/HORTICULTURAL INSECTICIDE CONTAINING SAID COMPOUND AS ACTIVE INGREDIENT, AND METHOD FOR USING THE SAME

(71) Applicant: NIHON NOHYAKU CO., LTD., Chuo-ku, Tokyo (JP)

(72) Inventors: Nobuyuki Hayashi, Kawachinagano (JP); Toshihiko Shigenari, Kawachinagano (JP); Kosuke Fukatsu, Kawachinagano (JP)

(73) Assignee: NIHON NOHYAKU CO., LTD., Tokyo (JP)

(*) Notice: Subject to any disclaimer, the term of this patent is extended or adjusted under 35 U.S.C. 154(b) by 0 days.

(21) Appl. No.: 15/504,953

(22) PCT Filed: Aug. 18, 2015

(86) PCT No.: PCT/JP2015/073063
§ 371 (c)(1),
(2) Date: Feb. 17, 2017

(87) PCT Pub. No.: WO2016/027790
PCT Pub. Date: Feb. 25, 2016

(65) Prior Publication Data
US 2017/0260199 A1  Sep. 14, 2017

(30) Foreign Application Priority Data
Aug. 19, 2014  (JP) .................. 2014-166390

(51) Int. Cl.
C07D 498/04 (2006.01)
C07D 498/14 (2006.01)
A01N 43/90 (2006.01)
A61K 31/553 (2006.01)

(52) U.S. Cl.
CPC .......... *C07D 498/04* (2013.01); *A01N 43/90* (2013.01); *A61K 31/553* (2013.01); *C07D 498/14* (2013.01)

(58) Field of Classification Search
CPC ...................... C07D 498/04; C07D 498/14
See application file for complete search history.

(56) References Cited

U.S. PATENT DOCUMENTS

2013/0210883 A1  8/2013  Grillari et al.

FOREIGN PATENT DOCUMENTS

| EP | 0374753 A2 | 6/1990 |
| EP | 0427529 A1 | 5/1991 |
| EP | 0451878 A1 | 10/1991 |
| EP | 0558999 A2 | 9/1993 |
| WO | 9307278 A1 | 4/1993 |
| WO | 9534656 A1 | 12/1995 |
| WO | 2001025241 A2 | 4/2001 |
| WO | 03039255 A1 | 5/2003 |
| WO | 03052073 A2 | 6/2003 |
| WO | 2004026030 A2 | 4/2004 |

OTHER PUBLICATIONS

Notification of Transmittal of Translation of the International Preliminary Report on Patentability (PCT/IB/338) dated Mar. 2, 2017, with International Preliminary Report on Patentability (PCT/IB/373) and Written Opinion of the International Searching Authority (PCT/ISA/237), for corresponding international application PCT/JP2015/073063.
Delye, Weed resistance to acetyl coenzyme a carboxylase inhibitors: an update, Weed Science, 2005, 728-746, vol. 53.
Extended European Search Report (EESR) dated Dec. 8, 2017, issued for European counterpart patent application No. EP15833026.6.
Gura T., Repairing the Genome's Spelling Mistakes, Science, Jul. 16, 1999, 316-318, vol. 285.
International Search Report (ISR) dated Nov. 10, 2015, issued for International application No. PCT/JP2015/073063.
Parker et. al., Dominant mutations causing alterations in acetyl-coenzyme A carboxylase confer tolerance to cyclohexanedione and aryloxyphenoxypropionate herbicides in maize, Proc. Natl. Acad. Sci. USA, Sep. 1990, pp. 7175-7179, vol. 87.

*Primary Examiner* — Bruck Kifle
(74) *Attorney, Agent, or Firm* — Law Office of Katsuhiro Arai

(57) ABSTRACT

An oxazepine compound, or salt thereof, has General Formula (I):

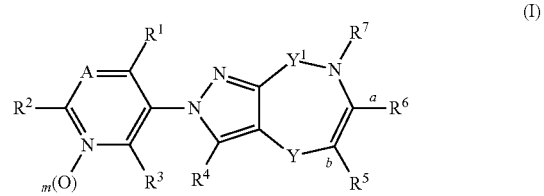

wherein $R^1$, $R^2$, $R^3$ and $R^4$ may be identical or different, representing a hydrogen atom, halogen atom, alkyl group, etc.; $R^5$ and $R^6$ may be identical or different, representing a hydrogen atom, alkyl group, or phenyl group, pyridyl group, etc., that may be substituted together with a carbon atom to which $R^5$ or $R^6$ is bonded; $R^7$ represents a hydrogen atom, alkyl group, alkynyl group, cyano alkyl group, alkoxy alkyl group, etc.; Y represents an oxygen atom, S, NH, etc.; $Y^1$ represents a C=O, C=S, $CH_2$ group, etc.; A represents a CH group, etc.; and m represents 0 or 1], as well as an agricultural/horticultural insecticide using such oxazepine compound or salt thereof as its active ingredient, and method for using the same.

12 Claims, No Drawings

OXAZEPINE COMPOUND AND AGRICULTURAL/HORTICULTURAL INSECTICIDE CONTAINING SAID COMPOUND AS ACTIVE INGREDIENT, AND METHOD FOR USING THE SAME

This application is the U.S. National Phase under 35 U.S.C. § 371 of International Application PCT/JP2015/073063, filed Aug. 18, 2015, which claims priority to Japanese Patent Application No. 2014-166390, filed Aug. 19, 2014. The International Application was published under PCT Article 21(2) in a language other than English.

TECHNICAL FIELD

The present invention relates to an agricultural/horticultural insecticide containing an oxazepine compound or salt thereof as its active ingredient, as well as a method for using the same.

BACKGROUND ART

Patent Literature 1 and Patent Literature 2 describe that a certain type of dibenzoxazepine compound possesses insecticidal activity.

BACKGROUND ART LITERATURE

Patent Literature

Patent Literature 1: International Patent Laid-open No. 2003/039255
Patent Literature 2: International Patent Laid-open No. 2004/026030

SUMMARY OF THE INVENTION

Problems to be Solved by the Invention

Pest insects, etc., are still causing serious damage to production of agricultural, horticultural and other crops, and due to the reasons such as emergence of pest insects that are resistant to existing chemicals, etc., there is a need to develop new agricultural/horticultural insecticides and miticides. As farm workers age, there is also a need for various labor-saving applications of agricultural/horticultural insecticides, as well as a need to create agricultural/horticultural insecticides having properties suitable for such applications.

Means for Solving the Problems

Through repeated studies in earnest to develop a new agricultural/horticultural insecticide, the inventors of the present invention found that an oxazepine compound or salt thereof expressed in General Formula (I), as proposed by the present invention, would be useful as an agricultural/horticultural insecticide, and completed the present invention accordingly.

To be specific, the present invention relates to the following:

[1] An oxazepine compound, or salt thereof, expressed by General Formula (I):

[Chemical 1]

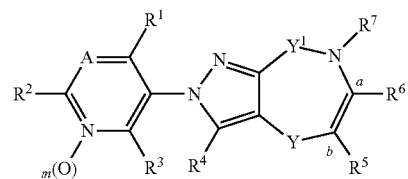

[in the formula, $R^1$, $R^2$, $R^3$ and $R^4$ may be identical or different, representing:
(a1) a hydrogen atom;
(a2) a halogen atom;
(a3) a ($C_1$-$C_8$) alkyl group;
(a4) a ($C_3$-$C_8$) cycloalkyl group;
(a5) a ($C_1$-$C_8$) alkoxy group;
(a6) a halo ($C_1$-$C_8$) alkyl group;
(a7) a ($C_1$-$C_8$) alkyl thio group;
(a8) a ($C_1$-$C_8$) alkyl sulfinyl group;
(a9) a ($C_1$-$C_8$) alkyl sulfonyl group;
(a10) a phenyl sulfonyl group;
(a11) an amino group; or
(a12) a ($C_1$-$C_8$) alkyl carbonyl amino group;
$R^5$ and $R^6$ may be identical or different, representing:
(b1) a hydrogen atom;
(b2) a halogen atom;
(b3) a ($C_1$-$C_8$) alkyl group; or
(b4) $R^5$ and $R^6$ which form Structural Formula $Q^1$, $Q^2$, $Q^3$, $Q^4$, $Q^5$, $Q^6$, $Q^7$, or $Q^8$ below together with carbon atoms to which the substitution groups are bonded:

[Chemical 2]

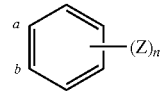

Q1

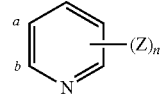

Q2

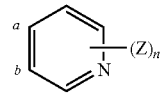

Q3

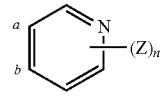

Q4

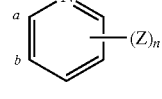

Q5

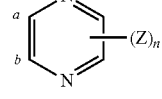

Q6

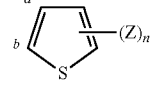

Q7

-continued

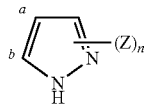
Q8

(in the formula, Z may be identical or different, representing (a) a halogen atom, (b) a cyano group, (c) a nitro group, (d) an amino group, (e) a di $(C_1-C_6)$ alkyl amino group ($(C_1-C_6)$ alkyl may be identical or different), (f) a $(C_1-C_6)$ alkyl group, (g) a $(C_1-C_6)$ alkoxy group, (h) a halo $(C_1-C_6)$ alkyl group, (i) a halo $(C_1-C_6)$ alkoxy group, (p) a hydroxyl group, (q) a nitro group, (r) a $(C_1-C_6)$ alkoxy $(C_1-C_6)$ alkyl group, (s) a di $(C_1-C_6)$ alkoxy $(C_1-C_6)$ alkyl group (alkyl in di $(C_1-C_6)$ alkoxy may be identical or different, and may be bonded to an identical or different carbon atom), (t) a phenyl group, (u) a mono $(C_1-C_6)$ alkyl amino group, (v) a mono formyl amino group, (w) a mono $(C_1-C_6)$ alkyl carbonyl amino group, (x) a mono $(C_1-C_6)$ alkyl sulfonyl amino group, (y) a bis $(C_1-C_6)$ alkyl sulfonyl amino group (alkyl in bis $(C_1-C_6)$ alkyl may be identical or different), (z) a $(C_1-C_6)$ alkoxy carbonyl group, (aa) a hydroxy carbonyl group, (ab) a $(C_1-C_6)$ alkyl sulfonyl amino carbonyl group, (ac) a $(C_1-C_6)$ alkyl sulfonyl group, (ad) a halo $(C_1-C_6)$ alkyl sulfonyl group, or (ae) an amino sulfonyl group, and n represents an integer of 0 to 2; and a and b each represent a bonding position);

$R^7$ represents:
(c1) a hydrogen atom;
(c2) a $(C_1-C_{12})$ alkyl group;
(c3) a $(C_2-C_8)$ alkenyl group;
(c4) a $(C_2-C_8)$ alkynyl group;
(c5) a cyano $(C_1-C_8)$ alkyl group;
(c6) a $(C_3-C_8)$ cycloalkyl group;
(c7) a halo $(C_1-C_8)$ alkyl group;
(c8) a halo $(C_2-C_8)$ alkenyl group;
(c9) a halo $(C_2-C_8)$ alkynyl group;
(c10) a $(C_1-C_8)$ alkoxy $(C_1-C_8)$ alkyl group;
(c11) a $(C_1-C_8)$ alkyl thio $(C_1-C_8)$ alkyl group;
(c12) a $(C_1-C_8)$ alkyl sulfinyl $(C_1-C_8)$ alkyl group;
(c13) a $(C_1-C_8)$ alkyl sulfonyl $(C_1-C_8)$ alkyl group;
(c14) a $(C_1-C_8)$ alkyl carbonyl group;
(c15) a $(C_1-C_8)$ alkoxy carbonyl group;
(c16) a $(C_1-C_8)$ alkoxy carbonyl $(C_1-C_8)$ alkyl group;
(c17) an amino $(C_1-C_8)$ alkyl group;
(c18) a di $((C_1-C_8)$ alkyl) amino $(C_1-C_8)$ alkyl group (in the formula, alkyl in di $(C_1-C_8)$ alkyl may be identical or different);
(c19) a non-aromatic heterocyclic $(C_1-C_8)$ alkyl group;
(c20) a non-aromatic heterocyclic $(C_1-C_8)$ alkyl group having, on its ring, one to five substitution group(s) which may be identical or different and selected from (a) halogen atom, (b) cyano group, (c) nitro group, (af) formyl group, (f) $(C_1-C_6)$ alkyl group, and (g) $(C_1-C_6)$ alkoxy group;
(c21) a phenyl group;
(c22) a phenyl group having, on its ring, one to five substitution group(s) which may be identical or different and selected from (a) halogen atom, (b) cyano group, (c) nitro group, (af) formyl group, (f) $(C_1-C_6)$ alkyl group, (h) halo $(C_1-C_6)$ alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group, and (o) halo $(C_1-C_6)$ alkyl sulfonyl group;
(c23) a phenyl $(C_1-C_8)$ alkyl group;
(c24) a phenyl $(C_1-C_8)$ alkyl group having, on its ring, one to five substitution group(s) which may be identical or different and selected from (a) halogen atom, (b) cyano group, (c) nitro group, (af) formyl group, (f) $(C_1-C_6)$ alkyl group, (h) halo $(C_1-C_6)$ alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group and (o) halo $(C_1-C_6)$ alkyl sulfonyl group;
(c25) a phenyl carbonyl $(C_1-C_6)$ alkyl group;
(c26) a phenyl carbonyl $(C_1-C_8)$ alkyl group having, on its ring, one to five substitution group(s) which may be identical or different and selected from (a) halogen atom, (b) cyano group, (c) nitro group, (af) formyl group, (f) $(C_1-C_6)$ alkyl group, (h) halo $(C_1-C_6)$ alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group, and (o) halo $(C_1-C_6)$ alkyl sulfonyl group;
(c27) an aromatic heterocyclic group;
(c28) an aromatic heterocyclic group having, on its ring, one to three substitution group(s) which may be identical or different and selected from (a) halogen atom, (b) cyano group, (c) nitro group, (af) formyl group, (f) $(C_1-C_6)$ alkyl group, (h) halo $(C_1-C_6)$ alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group, and (o) halo $(C_1-C_6)$ alkyl sulfonyl group;
(c29) an aromatic heterocyclic $(C_1-C_8)$ alkyl group;
(c30) an aromatic heterocyclic $(C_1-C_8)$ alkyl group having, on its ring, one to three substitution group(s) which may be identical or different and selected from (a) halogen atom, (b) cyano group, (c) nitro group, (af) formyl group, (f) $(C_1-C_6)$ alkyl group, (h) halo $(C_1-C_6)$ alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group, and (o) halo $(C_1-C_6)$ alkyl sulfonyl group;
(c31) a $(C_1-C_8)$ alkyl sulfonyl group;
(c32) an amino carbonyl $(C_1-C_8)$ alkyl group;
(c33) a di $((C_1-C_8)$ alkyl) amino $(C_1-C_8)$ alkyl group (in the formula, alkyl in di $(C_1-C_8)$ alkyl may be identical or different);
(c34) a $(C_1-C_8)$ alkyl carbonyloxy $(C_1-C_8)$ alkyl group;
(c35) a di $(C_1-C_8)$ alkoxy $(C_1-C_8)$ alkyl group (in the formula, alkyl in di $(C_1-C_8)$ alkyl may be identical or different, and may be bonded to an identical or different carbon);
(c36) a formyl group;
(c37) a di $((C_1-C_8)$ alkyl) amino carbonyl group (in the formula, alkyl in di $(C_1-C_8)$ alkyl may be identical or different;
(c38) a formyl $(C_1-C_8)$ alkyl group;
(c39) a $(C_1-C_8)$ alkoxy imino $(C_1-C_8)$ alkyl group;
(c40) a halo $(C_1-C_8)$ alkyl thio $(C_1-C_8)$ alkyl group;

(c41) a halo $(C_1-C_8)$ alkyl sulfinyl $(C_1-C_8)$ alkyl group;
(c42) a halo $(C_1-C_8)$ alkyl sulfonyl $(C_1-C_8)$ alkyl group;
(c43) a $(C_3-C_8)$ cycloalkyl $(C_1-C_8)$ alkyl group; or
(c44) a cyano halo $(C_1-C_8)$ alkyl group;
A represents a CH, C—$R^8$ (in the formula, $R^8$ represents (a) a halogen atom, (b) a cyano group, (c) a nitro group, (af) a formyl group, (f) a $(C_1-C_6)$ alkyl group, (h) a halo $(C_1-C_6)$ alkyl group, (g) a $(C_1-C_6)$ alkoxy group, or (i) a halo $(C_1-C_6)$ alkoxy group) or nitrogen atom;
Y represents an oxygen atom, S, SO, $SO_2$, NH or N—$R^9$ (in the formula, $R^9$ represents a $(C_1-C_6)$ alkyl group);
$Y^1$ represents a C=O, C=S or $CH_2$ group, or a chemical group expressed by [Chemical 3] together with an adjoining nitrogen atom:

[Chemical 3]

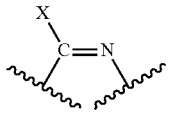

(in the formula, X represents:
(d1) a halogen atom;
(d2) a cyano group;
(d3) a tri $(C_1-C_6)$ alkyl silyl $(C_2-C_6)$ alkynyl group (the alkyl group in the tri $(C_1-C_6)$ alkyl silyl group may be identical or different);
(d4) a $NR^{10}R^{11}$ (in the formula, $R^{10}R^{11}$ may be identical or different, representing a hydrogen atom, hydroxyl group, $(C_1-C_6)$ alkyl group, $(C_2-C_6)$ alkenyl group, $(C_3-C_6)$ cycloalkyl group, halo $(C_1-C_6)$ alkyl group or non-aromatic heterocyclic group);
(d5) a $(C_1-C_6)$ alkoxy $(C_1-C_6)$ alkoxy group;
(d6) a $(C_1-C_6)$ alkyl thio $(C_1-C_6)$ alkoxy group;
(d7) a $(C_1-C_6)$ alkyl thio group;
(d8) a $(C_1-C_6)$ alkoxy group; or
(d9) a halo $(C_1-C_6)$ alkoxy group); and
m represents an integer of 0 or 1].

[2] An oxazepine compound, or salt thereof, according to [1] above, wherein:
$R^1$, $R^2$, $R^3$ and $R^4$ may be identical or different, representing:
(a1) a hydrogen atom;
(a2) a halogen atom;
(a3) a $(C_1-C_8)$ alkyl group;
(a10) a phenyl sulfonyl group;
(a11) an amino group; or
(a12) a $(C_1-C_8)$ alkyl carbonyl amino group;
$R^5$ and $R^6$ may be identical or different, representing:
(b1) a hydrogen atom;
(b3) a $(C_1-C_8)$ alkyl group; or
(b4) $R^5$ and $R^6$ which form Structural Formula $Q^1$, $Q^2$, $Q^3$, $Q^4$, $Q^5$, $Q^6$, $Q^7$, or $Q^8$ together with carbon atoms to which they are bonded;
$R^7$ is:
(c1) a hydrogen atom;
(c2) a $(C_1-C_{12})$ alkyl group;
(c3) a $(C_2-C_8)$ alkenyl group;
(c4) a $(C_2-C_8)$ alkynyl group;
(c5) a cyano $(C_1-C_8)$ alkyl group;
(c6) a $(C_3-C_8)$ cycloalkyl group;
(c7) a halo $(C_1-C_8)$ alkyl group;
(c10) a $(C_1-C_8)$ alkoxy $(C_1-C_8)$ alkyl group;
(c11) a $(C_1-C_8)$ alkyl thio $(C_1-C_8)$ alkyl group;
(c12) a $(C_1-C_8)$ alkyl sulfinyl $(C_1-C_8)$ alkyl group;
(c13) a $(C_1-C_8)$ alkyl sulfonyl $(C_1-C_8)$ alkyl group;
(c14) a $(C_1-C_8)$ alkyl carbonyl group;
(c16) a $(C_1-C_8)$ alkoxy carbonyl $(C_1-C_8)$ alkyl group;
(c18) a di $((C_1-C_8)$ alkyl) amino $(C_1-C_8)$ alkyl group (in the formula, alkyl in di $(C_1-C_8)$ alkyl may be identical or different);
(c19) a non-aromatic heterocyclic $(C_1-C_8)$ alkyl group;
(c20) a non-aromatic heterocyclic $(C_1-C_8)$ alkyl group having, on its ring, one to five substitution group(s) which may be identical or different and selected from (a) halogen atom, (b) cyano group, (c) nitro group, (af) formyl group, (f) $(C_1-C_6)$ alkyl group and (g) $(C_1-C_6)$ alkoxy group;
(c21) a phenyl group;
(c23) a phenyl $(C_1-C_8)$ alkyl group;
(c24) a phenyl $(C_1-C_8)$ alkyl group having, on its ring, one to five substitution group(s) which may be identical or different and selected from (a) halogen atom, (b) cyano group, (c) nitro group, (af) formyl group, (f) $(C_1-C_6)$ alkyl group, (h) halo $(C_1-C_6)$ alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group and (o) halo $(C_1-C_6)$ alkyl sulfonyl group;
(c26) a phenyl carbonyl $(C_1-C_8)$ alkyl group having, on its ring, one to five substitution group(s) which may be identical or different and selected from (a) halogen atom, (b) cyano group, (c) nitro group, (af) formyl group, (f) $(C_1-C_6)$ alkyl group, (h) halo $(C_1-C_6)$ alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group, and (o) halo $(C_1-C_6)$ alkyl sulfonyl group;
(c27) an aromatic heterocyclic group;
(c29) an aromatic heterocyclic $(C_1-C_8)$ alkyl group;
(c30) an aromatic heterocyclic $(C_1-C_8)$ alkyl group having, on its ring, one to three substitution group(s) which may be identical or different and selected from (a) halogen atom, (b) cyano group, (c) nitro group, (af) formyl group, (f) $(C_1-C_6)$ alkyl group, (h) halo $(C_1-C_6)$ alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group, and (o) halo $(C_1-C_6)$ alkyl sulfonyl group;
(c31) a $(C_1-C_8)$ alkyl sulfonyl group;
(c32) an amino carbonyl $(C_1-C_8)$ alkyl group;
(c33) a di $((C_1-C_8)$ alkyl) amino $(C_1-C_8)$ alkyl group (in the formula, alkyl in di $(C_1-C_8)$ alkyl may be identical or different);
(c34) a $(C_1-C_8)$ alkyl carbonyloxy $(C_1-C_8)$ alkyl group;
(c35) a di $(C_1-C_8)$ alkoxy $(C_1-C_8)$ alkyl group (in the formula, alkyl in di $(C_1-C_8)$ alkyl may be identical or different);
(c36) a formyl group;
(c37) a di $((C_1-C_8)$ alkyl) amino carbonyl group (in the formula, alkyl in di $(C_1-C_8)$ alkyl may be identical or different);
(c38) a formyl $(C_1-C_8)$ alkyl group;
(c39) a $(C_1-C_8)$ alkoxy imino $(C_1-C_8)$ alkyl group;
(c40) a halo $(C_1-C_8)$ alkyl thio $(C_1-C_8)$ alkyl group;
(c41) a halo $(C_1-C_8)$ alkyl sulfinyl $(C_1-C_8)$ alkyl group;
(c42) a halo $(C_1-C_8)$ alkyl sulfonyl $(C_1-C_8)$ alkyl group;

(c43) a $(C_3\text{-}C_8)$ cycloalkyl $(C_1\text{-}C_8)$ alkyl group; or
(c44) a cyano halo $(C_1\text{-}C_8)$ alkyl group;
A is a CH, C—$R^8$ (in the formula, $R^8$ represents (a) a halogen atom, (b) a cyano group, (c) a nitro group, (af) a formyl group, (f) a $(C_1\text{-}C_6)$ alkyl group, (h) a halo $(C_1\text{-}C_6)$ alkyl group, (g) a $(C_1\text{-}C_6)$ alkoxy group, or (i) a halo $(C_1\text{-}C_6)$ alkoxy group) or nitrogen atom;
Y is an oxygen atom, S or NH;
$Y^1$ is a C=O, C=S or $CH_2$ group; and
m is 0 or 1.

[3] An oxazepine compound, or salt thereof, according to [1] or [2] above, wherein: $R^1$, $R^2$, $R^3$, and $R^4$ may be identical or different, representing:
(a1) a hydrogen atom; or
(a2) a halogen atom;
$R^5$ and $R^6$ form Structural Formula $Q^1$ or $Q^7$ together with carbon atoms to which they are bonded;
$R^7$ is:
(c1) a hydrogen atom;
(c2) a $(C_1\text{-}C_{12})$ alkyl group;
(c4) a $(C_2\text{-}C_8)$ alkynyl group;
(c5) a cyano $(C_1\text{-}C_8)$ alkyl group; or
(c10) a $(C_1\text{-}C_8)$ alkoxy $(C_1\text{-}C_8)$ alkyl group;
A is a CH;
Y is an oxygen atom;
$Y^1$ is a C=O; and
m is 0.

[4] An agricultural/horticultural insecticide characterized in that it contains, as its active ingredient, a compound or salt thereof according to any one of [1] to [3] above.

[5] A method for use of agricultural/horticultural insecticide, characterized in that an agricultural/horticultural insecticide according to [4] above is applied to plants or soil by an effective amount.

[6] Use of a compound or salt thereof according to any one of [1] to [3] above, as an agricultural/horticultural insecticide.

Effects of the Invention

The oxazepine compound or salt thereof as proposed by the present invention has excellent effects as an agricultural/horticultural insecticide. It is also effective on pest insects that live on dogs, cats, and other pets, or cows, sheep, and other livestock.

MODE FOR CARRYING OUT THE INVENTION

In the definition of General Formula (I) expressing the oxazepine compound proposed by the present invention:

"Halo" refers to "halogen atom" and represents a chlorine atom, bromine atom, iodine atom or fluorine atom;

"$(C_1\text{-}C_8)$ alkyl group" represents, for example, a methyl group, ethyl group, normal propyl group, isopropyl group, normal butyl group, isobutyl group, secondary butyl group, tertiary butyl group, normal pentyl group, isopentyl group, tertiary pentyl group, neopentyl group, 2,3-dimethyl propyl group, 1-ethyl propyl group, 1-methyl butyl group, 2-methyl butyl group, normal hexyl group, isohexyl group, 2-hexyl group, 3-hexyl group, 2-methyl pentyl group, 3-methyl pentyl group, 1,1,2-trimethyl propyl group, 3,3-dimethyl butyl group, normal heptyl group, 2-heptyl group, 3-heptyl group, 2-methyl hexyl group, 3-methyl hexyl group, 4-methyl hexyl group, isoheptyl group, normal octyl group, or other straight-chain or branched-chain alkyl group with a carbon atom number of 1 to 8;

"$(C_1\text{-}C_{12})$ alkyl group" represents, for example, a methyl group, ethyl group, normal propyl group, isopropyl group, normal butyl group, isobutyl group, secondary butyl group, tertiary butyl group, normal pentyl group, isopentyl group, tertiary pentyl group, neopentyl group, 2,3-dimethyl propyl group, 1-ethyl propyl group, 1-methyl butyl group, normal hexyl group, isohexyl group, 1,1,2-trimethyl propyl group, heptyl group, octyl group, nonyl group, decyl group, undecyl group, dodecyl group, or other straight-chain or branched-chain alkyl group with a carbon atom number of 1 to 12;

"$(C_2\text{-}C_8)$ alkenyl group" represents, for example, a vinyl group, allyl group, isopropenyl group, 1-butenyl group, 2-butenyl group, 2-methyl-2-propenyl group, 1-methyl-2-propenyl group, 2-methyl-1-propenyl group, pentenyl group, 1-hexenyl group, 3,3-dimethyl-1-butenyl group, heptenyl group, octenyl group, or other straight-chain or branched-chain alkenyl group with a carbon atom number of 2 to 8; and "$(C_2\text{-}C_8)$ alkynyl group" represents, for example, an ethynyl group, 1-propynyl group, 2-propynyl group, 1-butynyl group, 2-butynyl group, 3-butynyl group, 3-methyl-1-propynyl group, 2-methyl-3-propynyl group, pentynyl group, 1-hexynyl group, 3-methyl-1-butynyl group, 3,3-dimethyl-1-butynyl group, heptynyl group, octynyl group, or other straight-chain or branched-chain alkynyl group with a carbon atom number of 2 to 8.

"$(C_3\text{-}C_8)$ cycloalkyl group" represents, for example, a cyclopropyl group, cyclobutyl group, cyclopentyl group, cyclohexyl group, cycloheptyl group, cyclooctyl group, or other cyclic alkyl group with a carbon atom number of 3 to 8;

"$(C_1\text{-}C_8)$ alkoxy group" represents, for example, a methoxy group, ethoxy group, normal propoxy group, isopropoxy group, normal butoxy group, secondary butoxy group, tertiary butoxy group, normal pentyloxy group, isopentyloxy group, tertiary pentyloxy group, neopentyloxy group, 2,3-dimethyl propyloxy group, 1-ethyl propyloxy group, 1-methyl butyloxy group, normal hexyloxy group, isohexyloxy group, 1,1,2-trimethyl propyloxy group, normal heptyloxy group, normal octyloxy group, or other straight-chain or branched-chain alkoxy group with a carbon atom number of 1 to 8;

"$(C_1\text{-}C_8)$ alkyl thio group" represents, for example, a methyl thio group, ethyl thio group, normal propyl thio group, isopropyl thio group, normal butyl thio group, secondary butyl thio group, tertiary butyl thio group, normal pentyl thio group, isopentyl thio group, tertiary pentyl thio group, neopentyl thio group, 2,3-dimethyl propyl thio group, 1-ethyl propyl thio group, 1-methyl butyl thio group, normal hexyl thio group, isohexyl thio group, 1,1,2-trimethyl propyl thio group, normal heptyl thio group, normal octyl thio group, or other straight-chain or branched-chain alkyl thio group with a carbon atom number of 1 to 8;

"$(C_1\text{-}C_8)$ alkyl sulfinyl group" represents, for example, a methyl sulfinyl group, ethyl sulfinyl group, normal propyl sulfinyl group, isopropyl sulfinyl group, normal butyl sulfinyl group, secondary butyl sulfinyl group, tertiary butyl sulfinyl group, normal pentyl sulfinyl group, isopentyl sulfinyl group, tertiary pentyl sulfinyl group, neopentyl sulfinyl group, 2,3-dimethyl propyl sulfinyl group, 1-ethyl propyl sulfinyl group, 1-methyl butyl sulfinyl group, normal hexyl sulfinyl group, isohexyl sulfinyl group, 1,1,2-trimethyl propyl sulfinyl group, normal heptyl sulfinyl group, normal octyl sulfinyl group, or other straight-chain or branched-chain alkyl sulfinyl group with a carbon atom number of 1 to 8; and "($C_1$-$C_8$) alkyl sulfonyl group" represents, for example, a methyl sulfonyl group, ethyl sulfonyl group, normal propyl sulfonyl group, isopropyl sulfonyl group, normal butyl sulfonyl group, secondary butyl sulfonyl group, tertiary butyl sulfonyl group, normal pentyl sulfonyl group, isopentyl sulfonyl group, tertiary pentyl sulfonyl group, neopentyl sulfonyl group, 2,3-dimethyl propyl sulfonyl group, 1-ethyl propyl sulfonyl group, 1-methyl butyl sulfonyl group, normal hexyl sulfonyl group, isohexyl sulfonyl group, 1,1,2-trimethyl propyl sulfonyl group, normal heptyl sulfonyl group, normal octyl sulfonyl group, or other straight-chain or branched-chain alkyl sulfonyl group with a carbon atom number of 1 to 8.

"($C_1$-$C_8$) alkyl carbonyl group" represents, for example, a methyl carbonyl group (acetyl group), ethyl carbonyl group, normal propyl carbonyl group, isopropyl carbonyl group, normal butyl carbonyl group, secondary butyl carbonyl group, tertiary butyl carbonyl group, normal pentyl carbonyl group, isopentyl carbonyl group, tertiary pentyl carbonyl group, neopentyl carbonyl group, 2,3-dimethyl propyl carbonyl group, 1-ethyl propyl carbonyl group, 1-methyl butyl carbonyl group, normal hexyl carbonyl group, isohexyl carbonyl group, 1,1,2-trimethyl propyl carbonyl group, normal heptyl carbonyl group, normal octyl carbonyl group, or other straight-chain or branched-chain alkyl carbonyl group with a carbon atom number of 1 to 8.

"($C_1$-$C_8$) alkoxy carbonyl group" represents, for example, a methoxy carbonyl group, ethoxy carbonyl group, normal propoxy carbonyl group, isopropoxy carbonyl group, normal butoxy carbonyl group, tertiary butoxy carbonyl group, normal pentyloxy carbonyl group, isopentyloxy carbonyl group, tertiary pentyloxy carbonyl group, neopentyloxy carbonyl group, 2,3-dimethyl propyloxy carbonyl group, 1-ethyl propyloxy carbonyl group, 1-methyl butyloxy carbonyl group, normal hexyloxy carbonyl group, isohexyloxy carbonyl group, 1,1,2-trimethyl propyloxy carbonyl group, normal heptyloxy carbonyl group, normal octyloxy carbonyl group, or other straight-chain or branched-chain alkoxy carbonyl group with a carbon atom number of 1 to 8.

"($C_1$-$C_6$) alkyl group" represents, for example, a methyl group, ethyl group, normal propyl group, isopropyl group, normal butyl group, isobutyl group, secondary butyl group, tertiary butyl group, normal pentyl group, isopentyl group, tertiary pentyl group, neopentyl group, 2,3-dimethyl propyl group, 1-ethyl propyl group, 1-methyl butyl group, 2-methyl butyl group, normal hexyl group, isohexyl group, 2-hexyl group, 3-hexyl group, 2-methyl pentyl group, 3-methyl pentyl group, 1,1,2-trimethyl propyl group, 3,3-dimethyl butyl group, or other straight-chain or branched-chain alkyl group with a carbon atom number of 1 to 6;

"($C_2$-$C_6$) alkenyl group" represents, for example, a vinyl group, allyl group, isopropenyl group, 1-butenyl group, 2-butenyl group, 2-methyl-2-propenyl group, 1-methyl-2-propenyl group, 2-methyl-1-propenyl group, pentenyl group, 1-hexenyl group, 3,3-dimethyl-1-butenyl group, or other straight-chain or branched-chain alkenyl group with a carbon atom number of 2 to 6; and "($C_2$-$C_6$) alkynyl group" represents, for example, an ethynyl group, 1-propynyl group, 2-propynyl group, 1-butynyl group, 2-butynyl group, 3-butynyl group, 3-methyl-1-propynyl group, 2-methyl-3-propynyl group, pentynyl group, 1-hexynyl group, 3-methyl-1-butynyl group, 3,3-dimethyl-1-butynyl group, or other straight-chain or branched-chain alkynyl group with a carbon atom number of 2 to 6.

"($C_3$-$C_6$) cycloalkyl group" represents, for example, a cyclopropyl group, cyclobutyl group, cyclopentyl group, cyclohexyl group, or other cyclic alkyl group with a carbon atom number of 3 to 6;

"($C_1$-$C_6$) alkoxy group" represents, for example, a methoxy group, ethoxy group, normal propoxy group, isopropoxy group, normal butoxy group, secondary butoxy group, tertiary butoxy group, normal pentyloxy group, isopentyloxy group, tertiary pentyloxy group, neopentyloxy group, 2,3-dimethyl propyloxy group, 1-ethyl propyloxy group, 1-methyl butyloxy group, normal hexyloxy group, isohexyloxy group, 1,1,2-trimethyl propyloxy group, or other straight-chain or branched-chain alkoxy group with a carbon atom number of 1 to 6;

"($C_1$-$C_6$) alkyl thio group" represents, for example, a methyl thio group, ethyl thio group, normal propyl thio group, isopropyl thio group, normal butyl thio group, secondary butyl thio group, tertiary butyl thio group, normal pentyl thio group, isopentyl thio group, tertiary pentyl thio group, neopentyl thio group, 2,3-dimethyl propyl thio group, 1-ethyl propyl thio group, 1-methyl butyl thio group, normal hexyl thio group, isohexyl thio group, 1,1,2-trimethyl propyl thio group, or other straight-chain or branched-chain alkyl thio group with a carbon atom number of 1 to 6;

"($C_1$-$C_6$) alkyl sulfinyl group" represents, for example, a methyl sulfinyl group, ethyl sulfinyl group, normal propyl sulfinyl group, isopropyl sulfinyl group, normal butyl sulfinyl group, secondary butyl sulfinyl group, tertiary butyl sulfinyl group, normal pentyl sulfinyl group, isopentyl sulfinyl group, tertiary pentyl sulfinyl group, neopentyl sulfinyl group, 2,3-dimethyl propyl sulfinyl group, 1-ethyl propyl sulfinyl group, 1-methyl butyl sulfinyl group, normal hexyl sulfinyl group, isohexyl sulfinyl group, 1,1,2-trimethyl propyl sulfinyl group, or other straight-chain or branched-chain alkyl sulfinyl group with a carbon atom number of 1 to 6; and "($C_1$-$C_6$) alkyl sulfonyl group" represents, for example, a methyl sulfonyl group, ethyl sulfonyl group, normal propyl sulfonyl group, isopropyl sulfonyl group, normal butyl sulfonyl group, secondary butyl sulfonyl group, tertiary butyl sulfonyl group, normal pentyl sulfonyl group, isopentyl sulfonyl group, tertiary pentyl sulfonyl group, neopentyl sulfonyl group, 2,3-dimethyl propyl sulfonyl group, 1-ethyl propyl sulfonyl group, 1-methyl butyl sulfonyl group, normal hexyl sulfonyl group, isohexyl sulfonyl group, 1,1,2-trimethyl propyl sulfonyl group, or other straight-chain or branched-chain alkyl sulfonyl group with a carbon atom number of 1 to 6.

With the aforementioned "alkyl group," "alkenyl group," "alkynyl group," "alkoxy group," "alkyl thio group," "alkyl sulfinyl group" and "alkyl sulfonyl group," one, two or more halogen atom(s) may be substituted at a substitutable position(s), and if two or more halogen atoms are substituted, the halogen atoms may be identical or different. When halogen-atom-substituted, they are referred to as "haloalkyl group," "haloalkenyl group," "haloalkynyl group," "haloalkoxy group," "haloalkyl thio group," "haloalkyl sulfinyl group," and "haloalkyl sulfonyl group," respectively.

The expressions "($C_1$-$C_6$)," "($C_1$-$C_8$)," "($C_2$-$C_6$)," "($C_2$-$C_8$)," "($C_3$-$C_6$)," "($C_3$-$C_8$)," etc., each represent a range of carbon atom numbers for each of the various substitution groups. The aforementioned definition also applies to groups to which the aforementioned substitution groups are linked; for example, "($C_1$-$C_8$) alkoxy ($C_1$-$C_8$) alkyl group" indicates that a straight-chain or branched-chain alkoxy group with a carbon number of 1 to 8 is bonded to a straight-chain or branched-chain alkyl group with a carbon number of 1 to 8.

Two substitution groups $R^5$ and $R^6$ may together form an aromatic ring or aromatic heterocyclic group. In this case, the aromatic ring is a phenyl group, while the aromatic heterocyclic group may be pyridyl, pyrimidinyl, pyridadinyl, pyradinyl, triadinyl, thienyl, furanyl, thiazoyl, oxazoyl, etc., but among these, a phenyl group, pyridyl group, pyradinyl group, thienyl group, and thiazoyl group are preferred.

Under the present invention, an "aromatic hexacyclic ring" may be pyridyl, pyrimidinyl, pyridadinyl, pyradinyl, triadinyl, thienyl, furanyl, thiazoyl, oxazoyl, etc.

Also, under the present invention, a "non-aromatic heterocyclic ring" may be, for example, pyrrolidinyl, piperidinyl, morpholinyl, thiomorpholinyl, piperadinyl, 4-methyl piperadinyl, oxazolidinyl, thiazolidinyl, imidazolidinyl, oxazolinyl, thiazolinyl, isoxazolinyl, imidazolinyl, dioxolanyl, tetrahydrofuranyl, dihydrofuran-2(3H)-one, or other monocyclic non-aromatic heterocyclic group.

The salt of oxazepine compound expressed by General Formula (I) according to the present invention may be, for example, hydrochloride salt, sulfate salt, nitrate salt, phosphate salt or other salt of inorganic acid, or acetate salt, fumarate salt, maleate salt, oxalate salt, methane sulfonate salt, benzene sulfonate salt, paratoluene sulfonate salt or other salt of organic acid, or salt made with a sodium ion, potassium ion, calcium ion, trimethyl ammonium, or other inorganic or organic base.

The oxazepine compound or salt thereof expressed by General Formula (I) according to the present invention may have one or more asymmetric centers, or two or more types of optical isomers or diastereomers, in its structural formula, and the present invention covers individual optical isomers as well as all mixtures containing such optical isomers at any ratios. Also, the oxazepine compound or salt thereof expressed by General Formula (I) according to the present invention may have two types of geometric isomers derived from carbon-carbon double bonds in its structural formula, and the present invention covers individual geometric isomers as well as all mixtures containing such geometric isomers at any ratios.

A preferable embodiment of the oxazepine compound expressed by General Formula (I) according to the present invention is shown below.

Preferably $R^1$, $R^2$, $R^3$, and $R^4$, being identical or different, are each:
a hydrogen atom;
a halogen atom;
a ($C_1$-$C_8$) alkyl group;
a phenyl sulfonyl group;
an amino group; or
a ($C_1$-$C_8$) alkyl carbonyl amino group; or
more preferably they, being identical or different, are each a hydrogen atom or halogen atom.

Preferably $R^5$ and $R^6$, being identical or different, are each:
a hydrogen atom; or
a ($C_1$-$C_8$) alkyl group; or
$R^5$ and $R^6$ are each expressed by Structural Formula $Q^1$, $Q^2$, $Q^3$, $Q^4$, $Q^5$, $Q^6$, $Q^7$, or $Q^8$ together with a carbon atom bonded to it; or
more preferably $R^5$ and $R^6$ are each expressed by Structural Formula $Q^1$ or $Q^7$ together with a carbon atom bonded to it.

Preferably $R^7$ is:
(c1) a hydrogen atom;
(c2) a ($C_1$-$C_{12}$) alkyl group;
(c3) a ($C_2$-$C_8$) alkenyl group;
(c4) a ($C_2$-$C_8$) alkynyl group;
(c5) a cyano ($C_1$-$C_8$) alkyl group;
(c6) a ($C_3$-$C_8$) cycloalkyl group;
(c7) a halo ($C_1$-$C_8$) alkyl group;
(c10) a ($C_1$-$C_8$) alkoxy ($C_1$-$C_8$) alkyl group;
(c11) a ($C_1$-$C_8$) alkyl thio ($C_1$-$C_8$) alkyl group;
(c12) a ($C_1$-$C_8$) alkyl sulfinyl ($C_1$-$C_8$) alkyl group;
(c13) a ($C_1$-$C_8$) alkyl sulfonyl ($C_1$-$C_8$) alkyl group;
(c14) a ($C_1$-$C_8$) alkyl carbonyl group;
(c16) a ($C_1$-$C_8$) alkoxy carbonyl ($C_1$-$C_8$) alkyl group;
(c18) a di (($C_1$-$C_8$) alkyl) amino ($C_1$-$C_8$) alkyl group (in the formula, alkyl in di ($C_1$-$C_8$) alkyl may be identical or different);
(c19) a non-aromatic heterocyclic ($C_1$-$C_8$) alkyl group;
(c20) an identical or different non-aromatic heterocyclic ($C_1$-$C_8$) alkyl group having, on its ring, one to five substitution group(s) selected from (a) halogen atom, (b) cyano group, (c) nitro group, (af) formyl group, (f) ($C_1$-$C_6$) alkyl group, and (g) ($C_1$-$C_6$) alkoxy group;
(c21) a phenyl group;
(c23) a phenyl ($C_1$-$C_8$) alkyl group;
(c24) an identical or different phenyl ($C_1$-$C_8$) alkyl group having, on its ring, one to five substitution group(s) selected from (a) halogen atom, (b) cyano group, (c) nitro group, (af) formyl group, (f) ($C_1$-$C_6$) alkyl group, (h) halo ($C_1$-$C_6$) alkyl group, (g) ($C_1$-$C_6$) alkoxy group, (i) halo ($C_1$-$C_6$) alkoxy group, (ag) ($C_3$-$C_6$) cycloalkyl ($C_1$-$C_6$) alkoxy group, (j) ($C_1$-$C_6$) alkyl thio group, (k) halo ($C_1$-$C_6$) alkyl thio group, (l) ($C_1$-$C_6$) alkyl sulfinyl group, (m) halo ($C_1$-$C_6$) alkyl sulfinyl group, (n) ($C_1$-$C_6$) alkyl sulfonyl group, and (o) halo ($C_1$-$C_6$) alkyl sulfonyl group;
(c26) an identical or different phenyl carbonyl ($C_1$-$C_8$) alkyl group having, on its ring, one to five substitution group(s) selected from (a) halogen atom, (b) cyano group, (c) nitro group, (af) formyl group, (f) ($C_1$-$C_6$) alkyl group, (h) halo ($C_1$-$C_6$) alkyl group, (g) ($C_1$-$C_6$) alkoxy group, (i) halo ($C_1$-$C_6$) alkoxy group, (ag) ($C_3$-$C_6$) cycloalkyl ($C_1$-$C_6$) alkoxy group, (j) ($C_1$-$C_6$) alkyl thio group, (k) halo ($C_1$-$C_6$) alkyl thio group, (l) ($C_1$-$C_6$) alkyl sulfinyl group, (m) halo ($C_1$-$C_6$) alkyl sulfinyl group, (n) ($C_1$-$C_6$) alkyl sulfonyl group, and (o) halo ($C_1$-$C_6$) alkyl sulfonyl group;
(c27) an aromatic heterocyclic group;
(c29) an aromatic heterocyclic ($C_1$-$C_8$) alkyl group;
(c30) an identical or different aromatic heterocyclic ($C_1$-$C_8$) alkyl group having, on its ring, one to three substitution group(s) selected from (a) halogen atom, (b) cyano group, (c) nitro group, (af) formyl group, (f) ($C_1$-$C_6$) alkyl group, (h) halo ($C_1$-$C_6$) alkyl group, (g) ($C_1$-$C_6$) alkoxy group, (i) halo ($C_1$-$C_6$) alkoxy group, (ag) ($C_3$-$C_6$) cycloalkyl ($C_1$-$C_6$) alkoxy group, (j) ($C_1$-$C_6$) alkyl thio group, (k) halo ($C_1$-$C_6$) alkyl thio group, (l) ($C_1$-$C_6$) alkyl sulfinyl group, (m) halo ($C_1$-$C_6$) alkyl sulfinyl group, (n) ($C_1$-$C_6$) alkyl sulfonyl group, and (o) halo ($C_1$-$C_6$) alkyl sulfonyl group;
(c31) a ($C_1$-$C_8$) alkyl sulfonyl group;
(c32) an amino carbonyl ($C_1$-$C_8$) alkyl group;
(c33) a di (($C_1$-$C_8$) alkyl) amino ($C_1$-$C_8$) alkyl group (in the formula, alkyl in di ($C_1$-$C_8$) alkyl may be identical or different);
(c34) a ($C_1$-$C_8$) alkyl carbonyloxy ($C_1$-$C_8$) alkyl group;
(c35) a di ($C_1$-$C_8$) alkoxy ($C_1$-$C_8$) alkyl group (in the formula, alkyl in di ($C_1$-$C_8$) alkyl may be identical or different);
(c36) a formyl group;
(c37) a di (($C_1$-$C_8$) alkyl) amino carbonyl group (in the formula, alkyl in di ($C_1$-$C_8$) alkyl may be identical or different);
(c38) a formyl ($C_1$-$C_8$) alkyl group;
(c39) a ($C_1$-$C_8$) alkoxy imino ($C_1$-$C_8$) alkyl group;

(c40) a halo $(C_1-C_8)$ alkyl thio $(C_1-C_8)$ alkyl group;
(c41) a halo $(C_1-C_8)$ alkyl sulfinyl $(C_1-C_8)$ alkyl group;
(c42) a halo $(C_1-C_8)$ alkyl sulfonyl $(C_1-C_8)$ alkyl group;
(c43) a $(C_3-C_8)$ cycloalkyl $(C_1-C_8)$ alkyl group; or
(c44) a cyano halo $(C_1-C_8)$ alkyl group; or
more preferably $R^7$ is:
(c1) a hydrogen atom;
(c2) a $(C_1-C_{12})$ alkyl group;
(c4) a $(C_2-C_8)$ alkynyl group;
(c5) a cyano $(C_1-C_8)$ alkyl group; or
(c10) a $(C_1-C_8)$ alkoxy $(C_1-C_8)$ alkyl group.

Preferably A is a CH, C—$R^8$ (in the formula, $R^8$ represents (a) a halogen atom, (b) a cyano group, (c) a nitro group, (af) a formyl group, (f) a $(C_1-C_6)$ alkyl group, (h) a halo $(C_1-C_6)$ alkyl group, (g) a $(C_1-C_6)$ alkoxy group, or (i) a halo $(C_1-C_6)$ alkoxy group) or nitrogen atom; or
more preferably A is a CH.
Preferably Y is an oxygen atom, S or NH; or
more preferably Y is an oxygen atom.
Preferably $Y^1$ is a C=O, C=S or $CH_2$ group; or
more preferably $Y^1$ is a C=O.
Preferably m is 0.

Various compounds according to the present invention can be manufactured using the manufacturing methods below, for example; however, the present invention is not limited to the following.

Manufacturing Method 1

[Chemical 4]

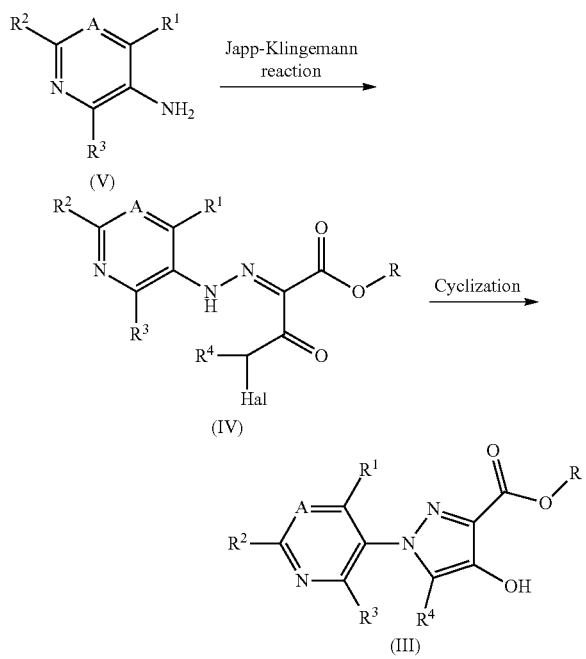

{In the formula, $R^1$, $R^2$, $R^3$, $R^4$, and A are the same as those mentioned above, while Hal represents a halogen atom and R represents an alkyl group of $C_1$ to $C_3$.}

Manufacturing Method of General Formula (III) from General Formula (V)

This reaction allows the above compound to be manufactured using an amino compound expressed by General Formula (V) as the starting material according to the method described in US2013/0210883, J. Med. Chem.,2009, 52, 2652-2655 or Org. React. 1959, 10, 143-178.

Manufacturing Method 2

[Chemical 5]

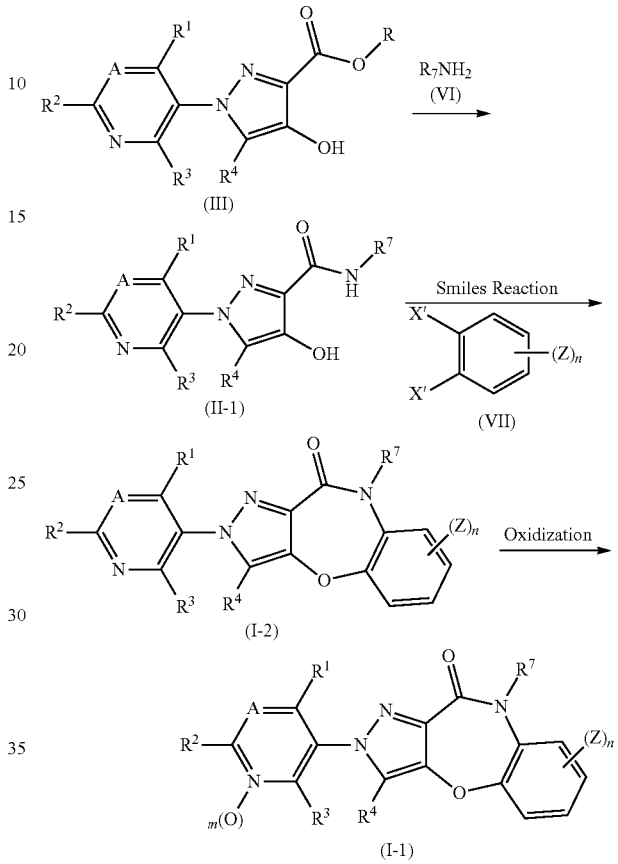

{In the formula, $R^1$, $R^2$, $R^3$, $R^4$, $R^7$, A, Z, m, and n are the same as those mentioned above, while X' represents a halogen atom, nitro group or other leaving group, and R represents an alkyl group of $C_1$ to $C_3$.}

Manufacturing Method of General Formula (II-1) from General Formula (III)

This reaction allows an amide compound expressed by General Formula (II-1) to be manufactured according to the method described in J. Med. Chem., 2009, 52, 2652-2655, using a 4-hydroxy pyrazole compound expressed by General formula (III) that has been manufactured according to Manufacturing Method 1 above, and an amine expressed by General Formula (VI).

Or, an amide compound expressed by General Formula (II-I) can be manufactured by hydrolyzing a 4-hydroxy pyrazole compound (III) to derive a carboxylic acid, and then causing the carboxylic acid and the amine (VI) to react with a condensing agent in the presence of an inert solvent and a base.

The base used in the hydrolytic reaction may be, for example, sodium hydroxide, potassium hydroxide, sodium carbonate, potassium carbonate, sodium hydrogen carbonate, potassium hydrogen carbonate, or other inorganic base, etc., which is normally used by an amount in a range of 1.0 to 10 molar times the amount of the 4-hydroxy pyrazole compound expressed by General Formula (III).

The acid used in the hydrolytic reaction may be, for example, hydrochloric acid, sulfuric acid, nitric acid, phosphoric acid, etc., which is used by an amount in a range of 1.0 to 10 molar times the amount of the 4-hydroxy pyrazole compound expressed by General Formula (III).

The inert solvent used in the hydrolytic reaction may be any solvent so long as it does not significantly inhibit the progression of this reaction, such as methanol, ethanol, isopropanol, or other alcohol; diethyl ether, methyl tertiary butyl ether (hereinafter referred to as "MTBE"), dioxane, tetrahydrofuran (hereinafter referred to as "THF"), or other chain or cyclic ether; dimethyl formamide, dimethyl acetamide, or other amide; acetone, methyl ethyl ketone, or other ketone; acetonitrile or other nitrile, or water, where any of these inert solvents may be used alone or two or more of them may be mixed together. The reaction temperature may be selected as anywhere between room temperature and the boiling point of the inert solvent used, and the reaction time, which varies depending on the reaction scale and reaction temperature, may be selected in a range of several minutes to 48 hours. Once the reaction is complete, the target substance may be isolated using any normal method from the reaction system that contains the target substance, and, if necessary, the isolated substance may be refined by means of re-crystallization, column chromatography, etc., to manufacture the target substance.

An amide compound expressed by General Formula (II-1) can be manufactured by causing a carboxylic acid manufactured through the aforementioned hydrolytic reaction, and an amine expressed by General Formula (VI), to react with a condensing agent in the presence of an inert solvent and a base.

The condensing agent used for the condensation reaction may be, for example, diethyl phosphorocyanidate (DEPC), carbonyl diimidazole (CDI), 1,3-dicyclohexyl carbodiimide (DCC), chlorocarbonic ester, 2-chloro-1-methyl pyridinium iodide, etc., which may be used by any amount selected as deemed appropriate in a range of 1 to 1.5 molar times the amount of the carboxylic acid.

The base used for the condensation reaction may be, for example, sodium hydroxide, potassium hydroxide, sodium carbonate, potassium carbonate, sodium hydrogen carbonate, potassium hydrogen carbonate or other inorganic base; sodium acetate, potassium acetate, or other acetate; triethyl amine, diisopropyl ethyl amine, 1,8-diaza bicycl [5.4.0] undec-7-ene, or other tertiary amine; pyridine, dimethyl aminopyridine, or other aromatic compound containing nitrogen, etc., which is normally used by an amount in a range of 1 to 10 molar times the amount of the amide compound expressed by General Formula (II-1).

The inert solvent used for the condensation reaction may be any solvent so long as it does not significantly inhibit the progression of this reaction, such as benzene, toluene, xylene, or other aromatic hydrocarbon; methylene chloride, chloroform, carbon tetrachloride, or other halogenated hydrocarbon; chlorobenzene, dichlorobenzene, or other halogenated aromatic hydrocarbon; diethyl ether, MTBE, dioxane, THF, or other chain or cyclic ether; ethyl acetate or other ester; dimethyl formamide, dimethyl acetamide, or other amide; acetone, methyl ethyl ketone, or other ketone; or other inert solvent, where any of these inert solvents may be used alone or two or more of them may be mixed together.

Since this reaction is an equimolar reaction, the carboxylic acid and amine only need to be used by an equimolar amount; however, either reaction agent may be used by an excessive amount. The reaction temperature may be selected as anywhere between room temperature and the boiling point of the inert solvent used, and the reaction time, which varies depending on the reaction scale and reaction temperature, may be selected in a range of several minutes to 48 hours.

Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of General Formula (I-2) from General Formula (II-1)

An oxazepine compound expressed by General Formula (I-2) can be manufactured according to the method described in ACS Comb. Sci. 2011, 13, 547-553 (Smiles Rearrangement), using an amide compound expressed by General Formula (II-1) that has been manufactured according to the aforementioned manufacturing method, and a benzene expressed by General Formula (VII).

Manufacturing Method of General Formula (I-1) from General Formula (I-2)

An oxazepine compound expressed by General Formula (I-1) can be manufactured by causing an oxazepine compound expressed by General Formula (I-2) to react with an oxidizing agent in an inert solvent. The oxidizing agent used for this reaction may be manganese dioxide or other manganese compound; oxidizing agent such as sodium chromate or other chromate; iron chloride, copper iodide, or other metal halogenation agent, iodine, bromine, or other halogen; hydrogen peroxide solution, perbenzoic acid, m-chloroperbenzoic acid, or other peroxide, or the like. Among others, hydrogen peroxide solution, perbenzoic acid, or m-chloroperbenzoic acid is preferred. Any of these oxidizing agents may be selected as deemed appropriate and used by an amount in a range of 1 to 5 molar times, or preferably in a range of 1 to 2 molar times, the amount of the oxazepine compound expressed by General Formula (I-2).

The inert solvent used for this reaction may be any solvent so long as it does not significantly inhibit the progression of this reaction, such as benzene, toluene, xylene, or other aromatic hydrocarbon; methylene chloride, chloroform, carbon tetrachloride, or other halogenated hydrocarbon; chlorobenzene, dichlorobenzene, or other halogenated aromatic hydrocarbon; acetonitrile or other nitrile; ethyl acetate or other ester; formic acid, acetic acid, or other organic acid; N,N-dimethyl formamide, N,N-dimethyl acetamide, 1,3-dimethyl-2-imidazolinone, water, or other polar solvent, where any of these inert solvents may be used alone or two or more of them may be mixed together.

For this reaction, any reaction temperature may be selected as deemed appropriate in a range of 0° C. to the reflux temperature of the inert solvent used. The reaction time, which varies depending on the reaction scale and reaction temperature, etc., may be selected as deemed appropriate in a range of several minutes to 48 hours.

Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method 3

[Chemical 6]

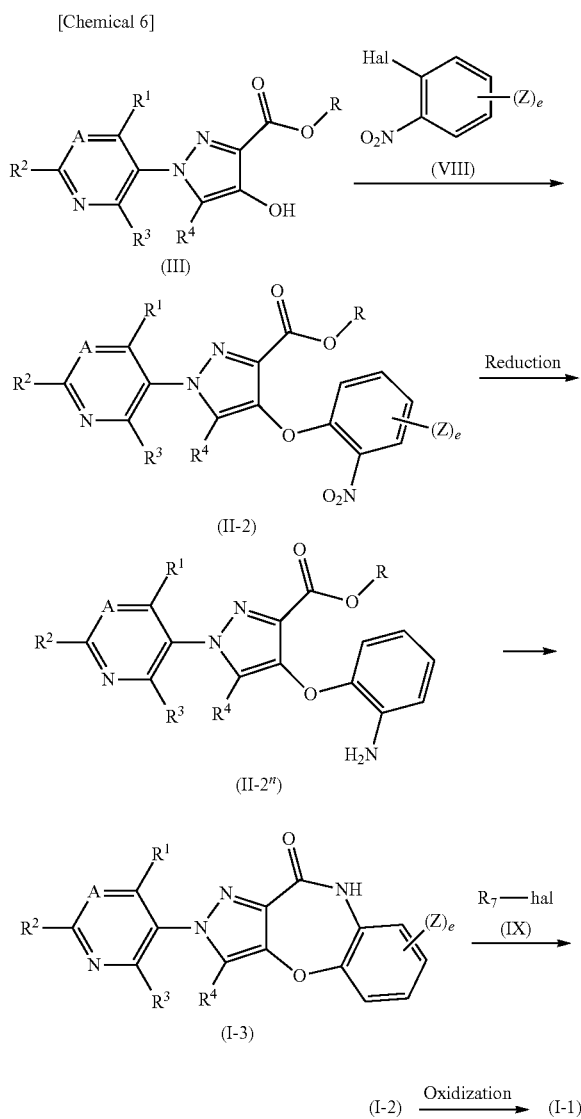

{In the formula, $R^1$, $R^2$, $R^3$, $R^4$, $R^7$, A, Z, m, and n are the same as those mentioned above, while Hal represents a halogen atom, and R represents an alkyl group of $C_1$ to $C_3$.}

Manufacturing Method of General Formula (II-2) from General Formula (III)

A nitrophenyl ether compound expressed by General Formula (II-2) can be manufactured by causing a 4-hydroxy pyrazole compound expressed by General Formula (III) to react with a nitrobenzene expressed by General Formula (VIII) in the presence of an inert solvent and a base.

The base used for this reaction may be sodium hydroxide, potassium hydroxide, sodium carbonate, potassium carbonate, cesium carbonate, sodium hydrogen carbonate, potassium hydrogen carbonate, or other inorganic base, sodium hydride, potassium hydride, or other alkali metal hydride, sodium methoxide, sodium ethoxide, tertiary butoxy potassium, or other alkali metal alkoxide, methyl lithium, normal butyl lithium, or other alkyl lithium, etc.

This base is normally used by an amount in a range of 1.0 to 10 molar times the amount of the 4-hydroxy pyrazole compound expressed by General Formula (III).

The inert solvent used for this reaction may be any solvent so long as it does not significantly inhibit the progression of this reaction, such as methanol, ethanol, isopropanol, or other alcohol; diethyl ether, MTBE, dioxane, THF, or other chain or cyclic ether; dimethyl formamide, dimethyl acetamide, or other amide; acetone, methyl ethyl ketone, or other ketone; acetonitrile or other nitrile, etc., where any of these inert solvents may be used alone or two or more of them may be mixed together. Since this reaction is an equimolar reaction, the 4-hydroxy pyrazole compound and nitrobenzene need to be used by an equimolar amount; however, either reaction agent may be used by an excessive amount.

Since this reaction is an equimolar reaction, each compound needs to be used by an equimolar amount; however, either compound may be used by an excessive amount. The reaction temperature may be selected as anywhere between room temperature and the boiling point of the inert solvent used, and the reaction time, which varies depending on the reaction scale and reaction temperature, may be selected in a range of several minutes to 48 hours.

Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of General Formula (II-2$^a$) from General Formula (II-2)

An aminophenyl ether compound expressed by General Formula (II-2$^a$) can be manufactured by reducing in an inert solvent a nitrophenyl ether compound expressed by General Formula (II-2).

Inert solvents that can be used for this reaction include, for example, methanol, ethanol and other alcohols, THF, dioxane, and other ether, acetic acid, hydrochloric acid, sulfuric acid, and other organic acids or inorganic acids, water, etc., where any of these inert solvents may be used alone or two or more of them may be mixed together. Additionally, an aqueous solution of the acid used as a reducing agent, as described below, may be used directly as an inert solvent. Reducing agents that can be used for this reaction are, for example, metal-acid, metal-salt, etc., where examples of metal include iron, tin, and zinc, examples of acid include hydrochloric acid, sulfuric acid, and other mineral acids, acetic acid and other organic acids, and examples of salt include tin chloride, ammonium chloride, ect. Any of the above can be combined together.

The reducing agent may be used by any amount selected as deemed appropriate in a range of 1 to 10 molar times in the case of a metal, or 0.05 to 10 molar times in the case of an acid or salt, the amount of the nitrophenyl ether expressed by General Formula (II-2). The reaction temperature may be selected in a range of 0 to 150° C., while the reaction time, which varies depending on the reaction scale, reaction temperature, etc., may be selected as deemed appropriate in a range of several minutes to 48 hours.

Or, the contact hydrogenation method may be used in the presence of a catalyst, where the catalyst may be, for example, palladium carbon, Raney nickel, etc. The hydrogen pressure may be selected in a range of 1 atm to 5 atm. Inert solvents that can be used include, for example, methanol, ethanol, and other alcohols, THF, dioxane, and other ethers, acetic acid and other organic acids, water, etc.

Once the reaction is complete, the target substance may be isolated using any normal method from the reaction system that contains the target substance, and, if necessary, the isolated substance may be refined according to the re-crystallization method, distillation method, column chromatography method, etc., to manufacture the target substance. Alternatively, after this reaction is complete the reaction system may be used directly for the next reaction without isolating the target substance.

Manufacturing Method of General Formula (I-3) from General Formula (II-2$^a$)

An oxazepine compound expressed by General Formula (I-3) can be manufactured by causing an aminophenyl ether compound expressed by General Formula (II-2$^a$) to react in the presence of an inert solvent and a base.

The base used for this reaction may be sodium hydroxide, potassium hydroxide, sodium carbonate, potassium carbonate, cesium carbonate, sodium hydrogen carbonate, potassium hydrogen carbonate, or other inorganic base, sodium hydride, potassium hydride, or other alkali metal hydride, sodium methoxide, sodium ethoxide, tertiary butoxy potassium, or other alkali metal alkoxide, methyl lithium, normal butyl lithium, or other alkyl lithium, etc.

This base is normally used by an amount in a range of 1.0 to 10 molar times the amount of the aminophenyl ether compound expressed by General Formula (II-2$^a$).

The inert solvent used for the this reaction may be any solvent so long as it does not significantly inhibit the progression of this reaction, such as methanol, ethanol, isopropanol, or other alcohol; diethyl ether, MTBE, dioxane, THF, or other chain or cyclic ether; dimethyl formamide, dimethyl acetamide, or other amide; acetone, methyl ethyl ketone, or other ketone; or acetonitrile or other nitrile, where any of these inert solvents may be used alone or two or more of them may be mixed together. The reaction temperature may be selected as anywhere between room temperature and the boiling point of the inert solvent used, and the reaction time, which varies depending on the reaction scale and reaction temperature, may be selected in a range of several minutes to 48 hours.

Once the reaction is complete, the target substance may be isolated using any normal method from the reaction system that contains the target substance, and, if necessary, the isolated substance may be refined by means of re-crystallization, column chromatography, etc., to manufacture the target substance.

Manufacturing Method of General Formula (I-2) from General Formula (I-3)

A compound expressed by General Formula (I-2) can be manufactured by causing an oxazepine compound expressed by General Formula (I-3) to react with a R$_7$-Hal (Hal is the same as the one described above) expressed by General Formula (IX) in the presence of an inert solvent and a base.

The base used for this reaction may be sodium hydroxide, potassium hydroxide, sodium carbonate, potassium carbonate, cesium carbonate, sodium hydrogen carbonate, potassium hydrogen carbonate, or other inorganic base, sodium hydride, potassium hydride, or other alkali metal hydride, sodium methoxide, sodium ethoxide, tertiary butoxy potassium, or other alkali metal alkoxide, methyl lithium, normal butyl lithium, or other alkyl lithium, etc.

This base is normally used by an amount in a range of 1.0 to 10 molar times the amount of the oxazepine compound expressed by General Formula (I-3).

The inert solvent used for the this reaction may be any solvent so long as it does not significantly inhibit the progression of this reaction, such as methanol, ethanol, isopropanol, or other alcohol; diethyl ether, MTBE, dioxane, THF, or other chain or cyclic ether; dimethyl formamide, dimethyl acetamide, or other amide; acetone, methyl ethyl ketone, or other ketone; or acetonitrile or other nitrile, where any of these inert solvents may be used alone or two or more of them may be mixed together. Since this reaction is an equimolar reaction, the oxazepine compound expressed by General Formula (I-3) and R$_7$-Hal expressed by General Formula (IX) need to be used by an equimolar amount; however, either reaction agent may be used by an excessive amount.

The reaction temperature may be selected as anywhere between room temperature and the boiling point of the inert solvent used, and the reaction time, which varies depending on the reaction scale and reaction temperature, may be selected in a range of several minutes to 48 hours.

Once the reaction is complete, the target substance may be isolated using any normal method from the reaction system that contains the target substance, and, if necessary, the isolated substance may be refined by means of re-crystallization, column chromatography, etc., to manufacture the target substance.

Similarly, concerning the manufacturing method of a compound (I) having a structure of $Q^2$, $Q^3$, $Q^4$ or $Q^5$ in General Formula (I), this compound can be manufactured in the same manner using a dihalopyridine instead of the compound (VII) disclosed in Manufacturing Method 2, or using a 2-halo-3-nitropyridine instead of the compound (VIII) disclosed in Manufacturing Method 3.

Additionally, concerning the manufacture of a compound (I) having a structure of $Q^6$ in General Formula (I), this compound can be manufactured in the same manner using a dihalopyradine instead of the compound (VII) disclosed in Manufacturing Method 2, or using a 2-halo-3-nitropyradine instead of the compound (VIII) disclosed in Manufacturing Method 3.

Furthermore, concerning the manufacture of a compound (I) having a structure of $Q^7$ or $Q^8$ in General Formula (I), this compound can be manufactured in the same manner using a 2-halo-3-nitrothiophene or 5-halo-4-nitropyrazole instead of the compound (VIII) disclosed in Manufacturing Method 3.

Manufacturing Method of General Formula (I-1) from General Formula (I-2)

A compound expressed by General Formula (I-1) can be manufactured according to the method described in Manufacturing Method 2 above.

Manufacturing Method 4

[Chemical 7]

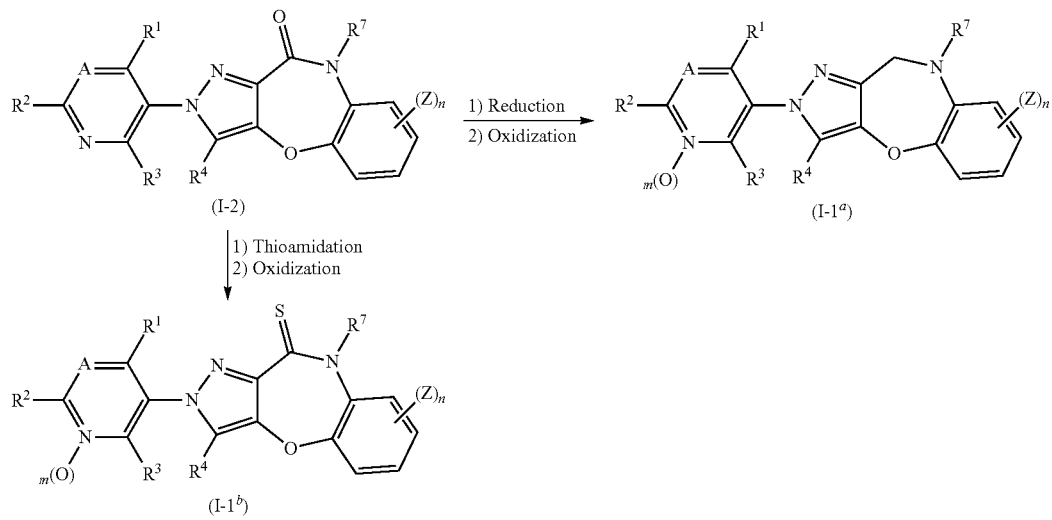

{In the formula, $R^1$, $R^2$, $R^3$, $R^4$, $R^7$, A, Z, m, and n are the same as those mentioned above.}

Manufacturing Method of General Formula (I-1$^a$) from General Formula (I-2)

A compound expressed by General Formula (I-1$^a$) can be manufactured by reducing, and then oxidizing, an oxazepine compound expressed by General Formula (I-2).

Reducing agents that can be used for the reduction reaction include, for example, sodium borohydride, lithium borohydride, zinc borohydride, lithium aluminum hydride, diisobutyl aluminum hydride, and other metal hydrogen complex compounds. The reducing agent may be used by an amount selected as deemed appropriate in a range of approx. 0.25 to 10 molar times the amount of the oxazepine compound expressed by General Formula (I-2).

The inert solvent used for this reaction may be any solvent so long as it does not significantly inhibit the progression of this reaction, such as methanol, ethanol, or other alcohol, THF, dioxane, or other ether, methylene chloride, chloroform, carbon tetrachloride, or other halogenated hydrocarbon, etc., where any of these inert solvents may be used alone or two or more of them may be mixed together. The reaction temperature may be selected as anywhere between approx. −20° C. and the boiling point of the solvent used, and the reaction time, which varies depending on the reaction scale, reaction temperature, etc., may be selected as deemed appropriate in a range of several minutes to approx. 48 hours. Once the reaction is complete, the target substance may be isolated using any normal method from the reaction system that contains the target substance, and, if necessary, the isolated substance may be refined according to the re-crystallization method, distillation method, column chromatography method, etc., to manufacture the target substance. Alternatively, after this reaction is complete the reaction system may be used directly for the next reaction without isolating the target substance.

The oxidization reaction in this reaction can be performed according to the method described in Manufacturing Method 2 above.

Manufacturing Method of General Formula (I-1$^b$) from General Formula (I-2)

A thioamide compound expressed by General Formula (I-1$^b$) can be manufactured by thiocarbonylating, and then oxidizing, an oxazepine compound expressed by General Formula (I-2).

The reagent that can be used in the thiocarbonylation reaction is not limited in any way, and phosphorus pentasulfide, Lawesson's reagent [2,4-bis (4-methoxy phenyl)-1,3-dithia-2,4-diphosphetane-2,4-disulfide], etc., may be used. The thiocarbonylation reagent can be used by an amount in a range of 0.5 to 5 molar times, or preferably 1 to 2 molar times, the amount of the oxazepine compound expressed by General Formula (I-2). The reaction temperature can be anywhere between 0° C. and the boiling point of the solvent, but preferably it is between room temperature and 150° C. The inert solvent used for this reaction may be any solvent so long as it does not significantly inhibit the progression of this reaction, such as benzene, toluene, xylene, diethyl ether, THF, dioxane, acetonitrile, or N,N-dimethyl formamide. The thioamide compound according to the general formula, as produced by this reaction, may be refined by means of re-crystallization or column chromatography.

The oxidization reaction in this reaction can be performed according to the method described in Manufacturing Method 2 above.

Manufacturing Method 5

[Chemical 8]

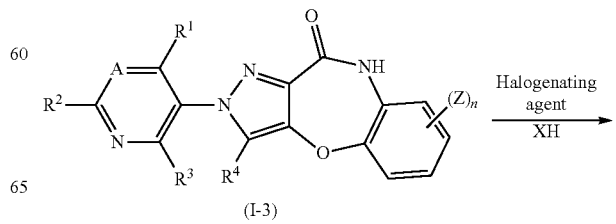

-continued

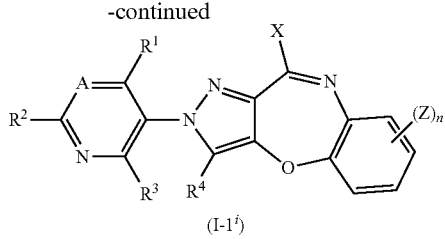

(I-1$^i$)

[In the formula, H represents a hydrogen atom, while $R^1$, $R^2$, $R^3$, $R^4$, A, Z, X, and n are the same as those mentioned above.]

A halide expressed by General Formula (I-1$^i$) can be derived by causing a compound (I-3) manufactured according to Manufacturing Method 3 to react with a thionyl chloride, phosphorus oxychloride, phosphorus trichloride, phosphorus tribromide, or other halogenating agent in the presence of a solvent or without any solvent.

The amount of halogenating agent may be selected as deemed appropriate in a range of 1.0 to 5 molar times the amount of the oxazepine compound expressed by General Formula (I-3). The reaction temperature can be anywhere between 0° C. and the boiling point of the solvent, but preferably it is between room temperature and 150° C. The inert solvent used for this reaction may be any solvent so long as it does not significantly inhibit the progression of this reaction, such as benzene, toluene, xylene, or other aromatic hydrocarbon, chlorobenzene, dichlorobenzene, or other halogenated aromatic hydrocarbon, methylene chloride, chloroform, carbon tetrachloride, or other halogenated hydrocarbon, diethyl ether or other ether, etc. The halide produced by this reaction may be refined by means of re-crystallization. Additionally, a compound expressed by General Formula (I-1') can be manufactured by causing the isolated product or unisolated product to react with a halogenating agent XH in the presence of a solvent and a base.

The amount of halogenating agent XH may be selected as deemed appropriate in a range of 1.0 to 5 molar times the amount of the oxazepine compound expressed by General Formula (I-1$^i$).

The base used for this reaction may be sodium hydroxide, potassium hydroxide, sodium carbonate, potassium carbonate, cesium carbonate, sodium hydrogen carbonate, potassium hydrogen carbonate, or other inorganic base, sodium hydride, potassium hydride, or other alkali metal hydride, sodium methoxide, sodium ethoxide, tertiary butoxy potassium, or other alkali metal alkoxide, methyl lithium, normal butyl lithium, or other alkyl lithium, etc. The inert solvent used for this reaction may be any solvent so long as it does not significantly inhibit the progression of this reaction, such as benzene, toluene, xylene, or other aromatic hydrocarbon; methylene chloride, chloroform, carbon tetrachloride, or other halogenated hydrocarbon; chlorobenzene, dichlorobenzene, or other halogenated aromatic hydrocarbon; acetonitrile or other nitrile; ethyl acetate or other ester; formic acid, acetic acid, or other organic acid; or N,N-dimethyl formamide, N,N-dimethyl acetamide, 1,3-dimethyl-2-imidazolinone, or other polar solvent, where any of these inert solvents may be used alone or two or more of them may be mixed together.

For this reaction, the reaction temperature may be selected as deemed appropriate in a range of 0° C. to the reflux temperature of the inert solvent used. The reaction time, which varies depending on the reaction scale, reaction temperature, etc., may be selected as deemed appropriate in a range of several minutes to 48 hours.

Once the reaction is complete, the target substance may be isolated using any normal method from the reaction system that contains the target substance, and, if necessary, the isolated substance may be refined by means of re-crystallization, column chromatography, etc., to manufacture the target substance.

The following illustrates representative examples of the oxazepine compound expressed by General Formula (I) according to the present invention, in Tables 1 to 11 and 13 to 26; it should be noted, however, that the present invention is not limited to these examples.

In the tables, "Me" represents a methyl group, "Et" represents an ethyl group, "Pr" represents a propyl group, "Bu" represents a butyl group, "Hex" represents a hexyl group, "Oct" represents an octyl group, "Bn" represents a benzyl group, "Ph" represents a phenyl group, "Py" represents a pyridyl group, "thaizol" represents a thiazoyl group, "n-" represents "normal," "t-" represents "tertiary," and "c-" represents "cyclo." For the physical property, either the melting point (° C.) or refractive index $n_D$ (measurement temperature; ° C.) is indicated.

Table 12 shows the $^1$H-NMR data of the compounds denoted by "NMR" in the "Physical property" columns of Tables 1 to 11 and 13 to 26.

[Chemical 9]

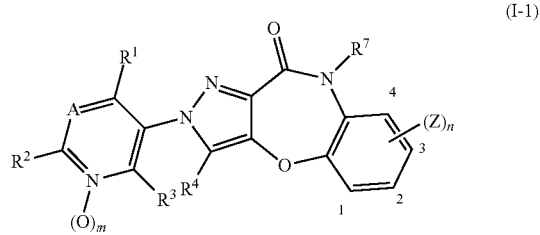

TABLE 1

| Compound No. | A | $R^1$ | $R^7$ | $(Z)_n$ | Physical property |
|---|---|---|---|---|---|
| 1-1 | CH | H | H | H | 259-262 |
| 1-2 | CH | H | Me | H | 195-196 |
| 1-3 | CH | H | CH$_2$C≡CH | H | 142-146 |
| 1-4 | CH | H | CH$_2$CN | H | 213-215 |
| 1-5 | CH | H | CH$_2$CF$_3$ | H | 211-213 |
| 1-6 | CH | H | H | 1-F | 297-299 |
| 1-7 | CH | H | Me | 1-F | 253-255 |
| 1-8 | CH | H | CH$_2$C≡CH | 1-F | 220-222 |
| 1-9 | CH | H | CH$_2$CN | 1-F | 195-197 |
| 1-10 | CH | H | H | 2-F | 285-288 |
| 1-11 | CH | H | Me | 2-F | 225-226 |
| 1-12 | CH | H | CH$_2$C≡CH | 2-F | 205-209 |
| 1-13 | CH | H | CH$_2$CN | 2-F | 212-214 |
| 1-14 | CH | H | H | 3-F | 294-296 |
| 1-15 | CH | H | Me | 3-F | 186-187 |
| 1-16 | CH | H | CH$_2$C≡CH | 3-F | 90-92 |
| 1-17 | CH | H | CH$_2$CN | 3-F | 173-175 |
| 1-18 | CH | H | H | 4-F | |
| 1-19 | CH | H | Me | 4-F | 235-237 |
| 1-20 | CH | H | CH$_2$C≡CH | 4-F | |

$R^2$, $R^3$, $R^4$ = H, m = 0

TABLE 2

| Compound No. | A | R¹ | R⁷ | (Z)ₙ | Physical property |
|---|---|---|---|---|---|
| 1-21 | CH | H | CH₂CN | 4-F | |
| 1-22 | CH | H | H | 1-Cl | 155-159 |
| 1-23 | CH | H | Me | 1-Cl | 224-226 |
| 1-24 | CH | H | CH₂C≡CH | 1-Cl | |
| 1-25 | CH | H | CH₂CN | 1-Cl | |
| 1-26 | CH | H | H | 2-Cl | >280 |
| 1-27 | CH | H | Me | 2-Cl | 241-243 |
| 1-28 | CH | H | CH₂C≡CH | 2-Cl | 193-196 |
| 1-29 | CH | H | CH₂CN | 2-Cl | 239-242 |
| 1-30 | CH | H | H | 2-Me | >280 |
| 1-31 | CH | H | Me | 2-Me | 217-221 |
| 1-32 | CH | H | CH₂C≡CH | 2-Me | 100-105 |
| 1-33 | CH | H | CH₂CN | 2-Me | 234-237 |
| 1-34 | CH | H | Me | 2-CF₃ | 211-212 |
| 1-35 | CH | H | CH₂C≡CH | 2-CF₃ | 201-204 |
| 1-36 | CH | H | CH₂CN | 2-CF₃ | 195-196 |
| 1-37 | CH | H | H | 3-CF₃ | 238-243 |
| 1-38 | CH | H | Me | 3-CF₃ | 174-177 |
| 1-39 | CH | H | H | 2-OMe | 289-291 |
| 1-40 | CH | H | Me | 2-OMe | 160-162 |
| 1-41 | CH | H | CH₂C≡CH | 2-OMe | 183-187 |
| 1-42 | CH | H | CH₂CN | 2-OMe | 214-215 |
| 1-43 | CH | H | Me | 2-NO₂ | 281-282 |
| 1-44 | CH | H | H | 3-NH₂ | 296-298 |
| 1-45 | CH | H | Me | 3-NH₂ | 195-198 |

R², R³, R⁴ = H, m = 0

TABLE 3

| Compound No. | A | R¹ | R⁷ | (Z)ₙ | Physical property |
|---|---|---|---|---|---|
| 1-46 | CH | H | Me | 3-NMe₂ | NMR |
| 1-47 | CH | H | Me | 2-CN | 269-271 |
| 1-48 | CH | H | CH₂C≡CH | 2-CN | 255-258 |
| 1-49 | CH | H | CH₂CN | 2-CN | |
| 1-50 | CH | H | H | 3-CN | 298-300 |
| 1-51 | CH | H | n-Bu | H | 1.3083(24.8° C.) |
| 1-52 | CH | H | n-Hex | H | 103-105 |
| 1-53 | CH | H | n-Oct | H | 96-98 |
| 1-54 | CH | H | c-Oct | H | |
| 1-55 | CH | H | CH₂CH=CH₂ | H | 1.3384(24.9° C.) |
| 1-56 | CH | H | Bn(4-MeO) | H | 179-181 |
| 1-57 | CH | H | CH₂(Py-2-yl) | H | 186-188 |
| 1-58 | CH | H | CH₂(Py-3-yl) | H | 110-113 |
| 1-59 | CH | H | CH₂(Py-4-yl) | H | |
| 1-60 | CH | H | CH₂(2-Cl-Py-5-yl) | H | |
| 1-61 | CH | H | CH₂(2-Cl-thaizol-5-yl) | H | |
| 1-62 | CH | H | CH₂CH₂Ph | H | 1.3182(24.5° C.) |
| 1-63 | CH | H | Ph | H | |
| 1-64 | CH | H | Py-2-yl | H | |
| 1-65 | CH | H | Py-3-yl | H | |
| 1-66 | CH | H | Py-4-yl | H | |
| 1-67 | CH | H | CH₂OCH₃ | H | 80-86 |
| 1-68 | CH | H | CH₂CH₂OCH₃ | H | 132-134 |
| 1-69 | CH | H | CH₂CH₂NMe₂ | H | >300 |

R², R³, R⁴ = H, m = 0

TABLE 4

| Compound No. | A | R¹ | R⁷ | (Z)ₙ | Physical property |
|---|---|---|---|---|---|
| 1-70 | CH | H | CH₂CH₂–N(piperidine) | H | 1.3875 (24.8° C.) |
| 1-71 | CH | H | CH₂CH₂–N(morpholine) | H | 157-159 |

TABLE 4-continued

| Compound No. | A | R¹ | R⁷ | (Z)ₙ | Physical property |
|---|---|---|---|---|---|
| 1-72 | CH | H | CH₂CH₂–N(N-Me piperazine) | H | |
| 1-73 | CH | H | C(=O)Me | H | 231-234 |
| 1-74 | CH | H | CH₂CO₂Me | H | 95-98 |
| 1-75 | CH | H | CH₂CO₂t-Bu | H | 120-125 |
| 1-76 | CH | H | CH₂C(=O)(4-ClPh) | H | NMR |
| 1-77 | CH | H | CH(CH₃)CN | H | 1.3527 (24.8° C.) |
| 1-78 | N | H | H | H | |
| 1-79 | N | H | Me | H | 225-230 |
| 1-80 | CF | H | Me | 2-F | 205-207 |
| 1-81 | CF | H | CH₂C≡CH | 2-F | 137-140 |
| 1-82 | CF | H | CH₂CN | 2-F | 254-255 |
| 1-83 | CBr | H | Me | H | 183-186 |
| 1-84 | CH | Me | Me | 2-F | 200-202 |
| 1-85 | CH | Me | CH₂C≡CH | 2-F | 134-136 |
| 1-86 | CH | Me | CH₂CN | 2-F | 212-214 |
| 1-87 | CH | H | Me | 2-NH₂ | 211-213 |

R², R³, R⁴ = H, m = 0

[Chemical 10]

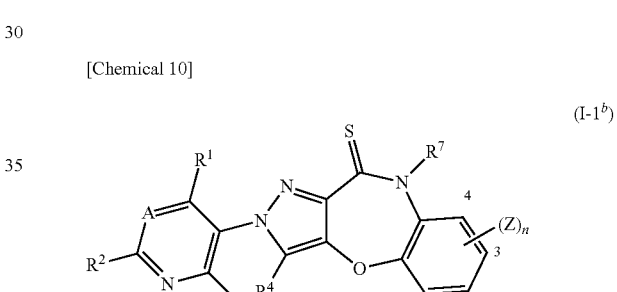

(I-1ᵇ)

TABLE 5

| Compound No. | A | R⁷ | (Z)ₙ | Physical property |
|---|---|---|---|---|
| 2-1 | CH | H | H | 228-231 |
| 2-2 | CH | Me | H | 206-210 |
| 2-3 | CH | CH₂C≡CH | H | |
| 2-4 | CH | CH₂CN | H | |
| 2-5 | CH | H | 3-F | 210-211 |

R¹, R², R³, R⁴ = H, m = 0

[Chemical 11]

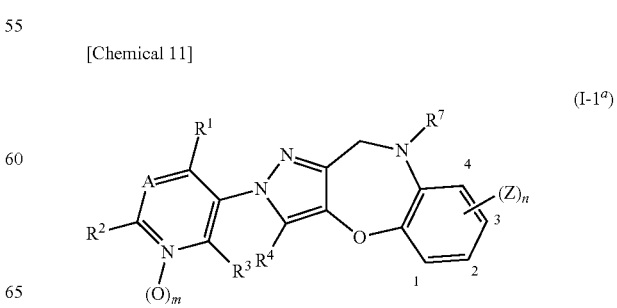

(I-1ᵃ)

TABLE 6

| Compound No. | A | R⁷ | (Z)ₙ | Physical property |
|---|---|---|---|---|
| 3-1 | CH | H | H | 238-241 |
| 3-2 | CH | Me | H | |
| 3-3 | CH | CH₂C≡CH | H | NMR |
| 3-4 | CH | CH₂CN | H | |
| 3-5 | CH | CH₂CN | 2-F | |
| 3-6 | CH | H | 3-F | 186-188 |
| 3-7 | CH | Me | 3-F | |
| 3-8 | CH | CH₂C≡CH | 3-F | |
| 3-9 | CH | C(=O)Me | 3-F | 190-191 |

$R^1, R^2, R^3, R^4 = H, m = 0$

[Chemical 12]

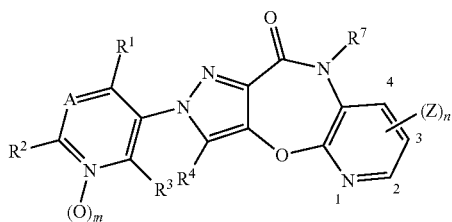

(I-1$^c$)

TABLE 7

| Compound No. | A | R⁷ | (Z)ₙ | Physical property |
|---|---|---|---|---|
| 4-1 | CH | H | H | |
| 4-2 | CH | Me | H | |
| 4-3 | CH | CH₂C≡CH | H | |
| 4-4 | CH | CH₂CN | H | |
| 4-5 | CH | H | 3-Me | |
| 4-6 | CH | Me | 3-Me | |
| 4-7 | CH | CH₂C≡CH | 3-Me | |
| 4-8 | CH | CH₂CN | 3-Me | |
| 4-9 | CH | H | 3-CF₃ | |
| 4-10 | CH | Me | 3-CF₃ | 216-219 |
| 4-11 | CH | CH₂C≡CH | 3-CF₃ | |
| 4-12 | CH | CH₂CN | 3-CF₃ | |

$R^1, R^2, R^3, R^4 = H, m = 0$

[Chemical 13]

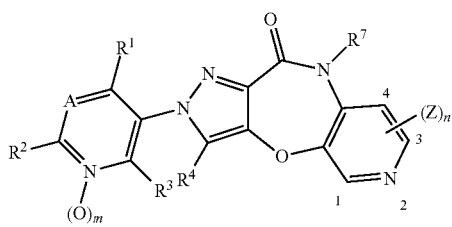

(I-1$^d$)

TABLE 8

| Compound No. | A | R⁷ | (Z)ₙ | Physical property |
|---|---|---|---|---|
| 5-1 | CH | H | H | |
| 5-2 | CH | Me | H | 258-262 |
| 5-3 | CH | CH₂C≡CH | H | |
| 5-4 | CH | CH₂CN | H | |

$R^1, R^2, R^3, R^4 = H, m = 0$

[Chemical 14]

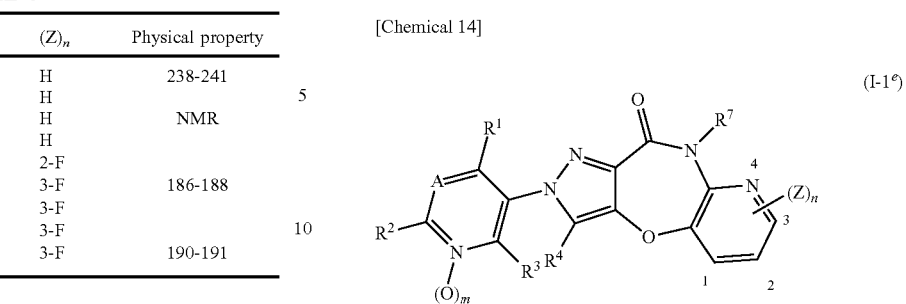

(I-1$^e$)

TABLE 9

| Compound No. | A | R⁷ | (Z)ₙ | Physical property |
|---|---|---|---|---|
| 6-1 | CH | H | 2-CF₃ | >280 |
| 6-2 | CH | Me | 2-CF₃ | 211-213 |
| 6-3 | CH | Et | 2-CF₃ | 135-137 |
| 6-4 | CH | n-Pr | 2-CF₃ | |
| 6-5 | CH | i-Pr | 2-CF₃ | 168-172 |
| 6-6 | CH | c-Pr | 2-CF₃ | 145-148 |
| 6-7 | CH | CH₂C≡CH | 2-CF₃ | 176-180 |
| 6-8 | CH | CH₂C≡CCH₃ | 2-CF₃ | |
| 6-9 | CH | CH₂CH₂F | 2-CF₃ | |
| 6-10 | CH | CH₂CHF₂ | 2-CF₃ | |
| 6-11 | CH | CH₂CF₃ | 2-CF₃ | 140-143 |
| 6-12 | CH | CF₂CHF₂ | 2-CF₃ | |
| 6-13 | CH | CF₂CF₃ | 2-CF₃ | |
| 6-14 | CH | CH₂CH₂CF₃ | 2-CF₃ | |
| 6-15 | CH | CH₂CF₂CF₃ | 2-CF₃ | |
| 6-16 | CH | CF₂CF₂CF₃ | 2-CF₃ | |
| 6-17 | CH | Bn | 2-CF₃ | 188-189 |
| 6-18 | CH | Ph | 2-CF₃ | 110-113 |
| 6-19 | CH | Py-2-yl | 2-CF₃ | |
| 6-20 | CH | Py-3-yl | 2-CF₃ | 135-138 |

$R^1, R^2, R^3, R^4 = H, m = 0$

TABLE 10

| Compound No. | A | R⁷ | (Z)ₙ | Physical property |
|---|---|---|---|---|
| 6-21 | CH | CH₂CH₂SCH₃ | 2-CF₃ | 192-193 |
| 6-22 | CH | CH₂CH₂SOCH₃ | 2-CF₃ | 103-106 |
| 6-23 | CH | CH₂CH₂SO₂CH₃ | 2-CF₃ | NMR |
| 6-24 | CH | CH(CH₃)CH₂SCH₃ | 2-CF₃ | |
| 6-25 | CH | CH(CH₃)CH₂SOCH₃ | 2-CF₃ | NMR |
| 6-26 | CH | CH(CH₃)CH₂SO₂CH₃ | 2-CF₃ | |
| 6-27 | CH | CH₂CN | 2-CF₃ | 177-180 |
| 6-28 | CH | CH(CH₃)CN | 2-CF₃ | |
| 6-29 | CH | Me | 2-CF₂CF₃ | 176-179 |
| 6-30 | CH | CH₂C≡CH | 2-CF₂CF₃ | |
| 6-31 | CH | CH₂CN | 2-CF₂CF₃ | |
| 6-32 | CH | Me | H | 199-201 |

$R^1, R^2, R^3, R^4 = H, m = 0$

[Chemical 15]

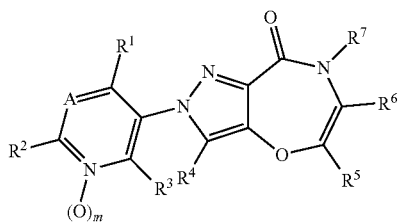

(I-1*f*)

$R^1, R^2, R^3, R^4 = H,$
$m = 0$

TABLE 11

| Compound No. | A | $R^7$ | $R^5$ | $R^6$ | Physical property |
|---|---|---|---|---|---|
| 7-1 | CH | H | H | H | 281-284 |
| 7-2 | CH | Me | H | H | 188-191 |
| 7-3 | CH | CH$_2$C≡CH | H | H | |
| 7-4 | CH | CH$_2$CN | H | H | |
| 7-5 | CH | Me | H | Me | NMR |
| 7-6 | CH | Me | Me | H | 167-169 |

TABLE 12

| Compound No. | $^1$H-NMR data (CDCl$_3$, except for 8-49 whose data is based on DMSO-d6) |
|---|---|
| 1-46 | 8.95-8.90 (1H, m), 8.63-8.55 (1H, m), 8.19-8.10 (1H, m), 7.79 (1H, s), 7.45-7.37 (1H, m), 7.08-7.01 (1H, m), 6.55-6.34 (2H, m), 3.56 (3H, s), 2.94 (3H, s), 2.83 (3H, s) |
| 1-76 | 8.95-8.92 (1H, m), 8.61-8.58 (1H, m), 8.16-8.12 (1H, m), 8.02-7.97 (2H, m), 7.86 (1H, s), 7.53-7.48 (2H, m), 7.46-7.39 (1H, m), 7.25-7.13 (4H, m), 5.33 (2H, s) |
| 3-3 | 8.92-8.88 (1H, m), 8.53-8.49 (1H, m), 7.98-7.93 (1H, m), 7.81 (1H, s), 7.54-7.50 (1H, m), 7.40-7.35 (1H, m), 7.19-7.13 (2H, m), 7.12-7.06 (1H, m), 4.40 (2H, s), 4.08 (2H, t), 2.43 (1H, t) |
| 6-23 | 8.99-8.93 (1H, m), 8.69-8.64 (1H, m), 8.61-8.58 (1H, m), 8.17-8.12 (1H, m), 7.92 (1H, s), 7.84-7.80 (1H, m), 7.50-7.43 (1H, m), 4.61-4.54 (2H, m), 3.85-3.78 (2H, m), 3.12 (3H, s) |
| 6-25 | 8.97-8.93 (1H, m), 8.66-8.60 (2H, m), 8.17-8.10 (1H, m), 7.91 (0.5H, s), 7.90 (0.5H, s), 7.82-7.78 (1H, m), 7.48-7.42 (1H, m), 5.20-5.02 (1H, m), 3.89 (0.5H, dd), 3.66-3.60 (1H, m), 3.24 (0.5H, dd), 2.72 (1.5H, s), 2.64 (1.5H, s), 1.86 (1.5H, d), 1.82 (1.5H, d) |
| 7-5 | 8.93 (1H, d), 8.60-8.58 (1H, m), 8.16-8.13 (1H, m), 7.66 (1H, s), 7.43-7.41 (1H, m), 6.29 (1H, d), 3.23 (3H, s), 1.88 (1H, d) |
| 8-23 | 8.93-8.94 (1H, d), 8.60-8.61 (1H, d), 8.13-8.16 (1H, dd), 7.85 (1H, s), 7.39-7.44 (2H, m), 6.90-6.97 (2H, m), 5.99-6.09 (1H, m), 5.30-5.35 (1H, dd), 5.25-5.28 (1H, dd), 4.65-4.67 (2H, dt) |
| 8-25 | 8.95 (1H, s), 8.63 (1H, s), 8.13-8.19 (1H, m), 7.86 (1H, s), 7.74-7.80 (1H, m), 7.42-7.47 (1H, m), 6.87-6.99 (2H, m), 5.28 (2H, s), 3.62 (3H, s) |
| 8-27 | 8.93-8.97 (1H, m), 8.60-8.61 (1H, m), 8.13-8.16 (1H, s), 7.85 (1H, s), 7.35-7.46 (2H, m), 6.94-7.02 (2H, m), 3.99-4.01 (2H, d), 2.27 (1H, m), 1.59 (1H, m) |
| 8-28 | 8.94 (1H, s), 8.60-8.61 (1H, d), 8.13-8.16 (1H, m), 7.86 (1H, s), 7.41-7.44 (1H, m), 7.29-7.31 (1H, m), 6.95-7.01 (2H, m), 3.98-3.99 (2H, d), 1.85-1.87 (1H, m), 1.43 (6H, m) |
| 8-34 | 8.95 (1H, brds), 8.62 (1H, brds), 8.12-8.14 (1H, d), 7.85 (1H, s), 7.42-7.43 (1H, m), 7.28-7.32 (1H, m), 6.96-7.02 (1H, m), 4.15-4.18 (2H, t), 3.38-3.41 (2H, t), 1.89-1.96 (2H, m), 1.79-1.86 (2H, m) |
| 8-40 | 8.94 (1H, brds), 8.61 (1H, brds), 8.12-8.15 (1H, m), 7.84 (1H, s), 7.41-7.44 (1H, s), 7.21-7.27 (1H, m), 7.04-7.07 (1H, dd), 6.89-6.93 (1H, m), 4.15-4.18 (2H, t), 3.39-3.42 (2H, t), 1.83-1.98 (4H, m) |
| 8-43 | 8.94 (1H, brds), 8.59 (1H, brds), 8.11-8.13 (1H, m), 7.88 (1H, s), 7.55-7.60 (1H, m), 7.41-7.43 (1H, m), 6.93-6.99 (2H, m), 5.30-5.33 (1H, m), 4.25-4.26 (2H, m), 3.87-4.00 (2H, m) |
| 8-47 | 8.92-8.94 (1H, d), 8.60-8.62 (1H, d), 8.12-8.15 (1H, m), 7.86 (1H, s), 7.41-7.44 (1H, m), 7.21-7.27 (2H, m), 6.92-6.95 (1H, m), 5.17 (2H, s), 2.30 (3H, s) |
| 8-49 | 9.08-9.09 (1H, d), 8.82 (1H, s), 8.62-8.63 (1H, dd), 8.24-8.27 (1H, m), 7.59-7.62 (2H, m), 7.40-7.44 (1H, m), 7.18-7.23 (H, m), 5.62 (2H, s), 3.02 (3H, s) |
| 8-51 | 8.93-8.94 (1H, d), 8.61-8.63 (1H, dd), 8.12-8.15 (1H, m), 7.86 (1H, s), 7.42-7.45 (1H, m), 7.23-7.27 (1H, m), 7.02-7.05 (1H, dd), 6.94-6.97 (1H, m), 4.22-4.25 (2H, t), 2.45-2.48 (2H, t), 2.12-217 (2H, q) |
| 8-115 | 8.94 (1H, d), 8.62-8.53 (1H, m), 8.16-8.13 (1H, m), 7.86 (1H, s), 7.45-7.42 (1H, m), 7.17 (1H, d), 7.07-7.05 (1H, m), 4.79 (2H, s), 2.39 (1H, s) |
| 8-129 | 8.98-8.99 (1H, d), 8.63-8.65 (1H, m), 8.14-8.17 (1H, m), 8.04 (1H, brds), 7.97 (1H, s), 7.42-7.47 (1H, m), 6.95-7.01 (1H, m), 6.78-6.80 (1H, m) |
| 15-6 | 8.71 (1H, s), 8.47 (1H, d), 7.87-7.85 (1H, m), 7.67 (1H, s), 6.66 (1H, d), 6.61 (1H, d), 4.01 (3H, s) |

[Chemical 16]

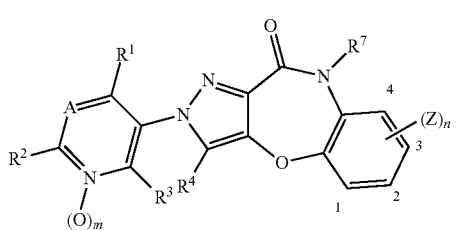

(I-1)

TABLE 13

| Compound No. | A | R¹ | R⁷ | (Z)ₙ | Physical property |
|---|---|---|---|---|---|
| 8-1 | CH | H | SO₂Me | H | 204-207 |
| 8-2 | CH | H | CH₂SCH₃ | H | 1.3237 (25.9° C.) |
| 8-3 | CH | H | CH₂SOCH₃ | H | 185-189 |
| 8-4 | CH | H | CH₂SO₂CH₃ | H | 218-220 |
| 8-5 | CH | H | CH₂C≡CCH₃ | H | 157-160 |
| 8-6 | CH | H | CH₂CH=C(CH₃)₂ | H | 163-167 |
| 8-7 | CH | H | CH₂C(=O)N(CH₃)₂ | H | 106 |
| 8-8 | CH | H | CH₂CH₂C(=O)NH₂ | H | 219-221 |
| 8-9 | CH | H | CH₂OC(=O)CH₃ | H | 177-179 |
| 8-10 | CH | H | CH₂CH(OCH₃)₂ | H | 147-153 |
| 8-11 | CH | H | 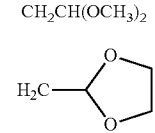 | H | 163-166 |
| 8-12 | CH | H | CHO | H | 234-235 |
| 8-13 | CH | H | CO₂CH₃ | H | 189-192 |
| 8-14 | CH | H | C(=O)N(CH₃)₂ | H | 1.3921 (27.0° C.) |
| 8-15 | CH | H | CH₂CHO | H | 185-190 |
| 8-16 | CH | H | CH₂C(=NOCH₃)H | H | 156-167 |
| 8-17 | CH | H | CH₂CH₂SCH₂CH₂CF₃ | H | 1.3800 (26.4° C.) |
| 8-18 | CH | H | CH₂CH₂SOCH₂CH₂CF₃ | H | 120-129 |
| 8-19 | CH | H | CH₂CH₂SO₂CH₂CH₂CF₃ | H | 71-78 |
| 8-20 | CH | H | CH₂CF₂CF₃ | H | 95-98 |

R², R³, R⁴ = H, m = 0

TABLE 14

| Compound No. | A | R¹ | R⁷ | (Z)ₙ | Physical property |
|---|---|---|---|---|---|
| 8-21 | CH | H | CH₂OCH₂CH₃ | H | 133-134 |
| 8-22 | CH | H | CH₂OCH₃ | 1-F | 157-159 |
| 8-23 | CH | H | CH₂CH=CH₂ | 2-F | NMR |
| 8-24 | CH | H | CH₂SCH₃ | 2-F | 164-169 |
| 8-25 | CH | H | CH₂OCH₃ | 2-F | NMR |
| 8-26 | CH | H | CH₂OCH₂CH₃ | 2-F | 164-165 |
| 8-27 | CH | H | CH₂c-Pr | 2-F | NMR |
| 8-28 | CH | H | CH₂CH(CH₃)₂ | 2-F | NMR |
| 8-29 | CH | H | CH(CH₃)CH₂CH₃ | 2-F | 1.3456 (20° C.) |
| 8-30 | CH | H | CH₂CH₂CH₂CN | 2-F | 134-138 |
| 8-31 | CH | H | 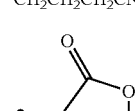 | 2-F | 231-235 |
| 8-32 | CH | H | CH(CH₃)C(=O)OC(CH₃)₃ | 2-F | 97-101 |
| 8-33 | CH | H | CHFCN | 2-F | 144-146 |
| 8-34 | CH | H | CH₂CH₂CH₂CH₂Br | 2-F | NMR |

TABLE 14-continued

| Compound No. | A | R¹ | R⁷ | (Z)ₙ | Physical property |
|---|---|---|---|---|---|
| 8-35 | CH | H | CH₂CH=CH₂ | 3-F | 117-119 |
| 8-36 | CH | H | CH₂c-Pr | 3-F | 178-179 |
| 8-37 | CH | H | (CH₂)₁₁CH₃ | 3-F | 113-115 |
| 8-38 | CH | H | CH₂CH₂Cl | 3-F | 154-157 |
| 8-39 | CH | H | CH₂CF₃ | 3-F | 208-211 |
| 8-40 | CH | H | CH₂CH₂CH₂CH₂Br | 3-F | NMR |

R², R³, R⁴ = H, m = 0

TABLE 15

| Compound No. | A | R¹ | R⁷ | (Z)ₙ | Physical property |
|---|---|---|---|---|---|
| 8-41 | CH | H | H₃C—(tetrahydrofuran-2-yl) | 3-F | 1.3456 (21° C.) |
| 8-42 | CH | H | CH₂CH(OCH₃)₂ | 3-F | 220-226 |
| 8-43 | CH | H | H₃C—(1,3-dioxolan-2-yl) | 3-F | NMR |
| 8-44 | CH | H | CH₂CH₂—morpholino | 3-F | 145-146 |
| 8-45 | CH | H | CH₂OCH₃ | 3-F | 117-119 |
| 8-46 | CH | H | CH₂OCH₂CH₃ | 3-F | 157-159 |
| 8-47 | CH | H | CH₂SCH₃ | 3-F | NMR |
| 8-48 | CH | H | CH₂SOCH₃ | 3-F | 82 |
| 8-49 | CH | H | CH₂SO₂CH₃ | 3-F | NMR |
| 8-50 | CH | H | CH(CH₃)CN | 3-F | 86-91 |
| 8-51 | CH | H | CH₂CH₂CH₂CN | 3-F | NMR |
| 8-52 | CH | H | CH₂C(=O)NH₂ | 3-F | 234-238 |
| 8-53 | CH | H | CHO | 3-F | 217-218 |
| 8-54 | CH | H | H | 3-Cl | >300 |
| 8-55 | CH | H | Me | 3-Cl | 110-111 |
| 8-56 | CH | H | CH₂C≡CH | 3-Cl | 192-194 |
| 8-57 | CH | H | CH₂CN | 3-Cl | 190-192 |
| 8-58 | CH | H | CH₂CH=CH₂ | 3-Cl | 145-147 |
| 8-59 | CH | H | Me | 4-Cl | 175-181 |
| 8-60 | CH | H | H | 2-Br | 296-298 |
| 8-61 | CH | H | Me | 2-Br | 226-229 |
| 8-62 | CH | H | H | 3-Br | >300 |
| 8-63 | CH | H | Me | 3-Br | 113-115 |
| 8-64 | CH | H | CH₂CH=CH₂ | 3-Br | 1.3627 (26.2° C.) |
| 8-65 | CH | H | CH₂C≡CH | 3-Br | 201-203 |

R², R³, R⁴ = H, m = 0

TABLE 16

| Compound No. | A | R¹ | R⁷ | (Z)ₙ | Physical property |
|---|---|---|---|---|---|
| 8-66 | CH | H | CH₂CN | 3-Br | 178-180 |
| 8-67 | CH | H | Me | 2-I | 260-264 |
| 8-68 | CH | H | H | 2-CHF₂ | 290-291 |
| 8-69 | CH | H | Me | 2-CF₃ | 188-191 |
| 8-70 | CH | H | CH₂CH=CH₂ | 3-CF₃ | 82-96 |
| 8-71 | CH | H | CH₂CH=C(CH₃)₂ | 3-CF₃ | 135-137 |
| 8-72 | CH | H | CH₂C≡CCH₃ | 3-CF₃ | 182 |
| 8-73 | CH | H | CH₂OCH₃ | 3-CF₃ | 150-153 |
| 8-74 | CH | H | CH₂SCH₃ | 3-CF₃ | 136-139 |
| 8-75 | CH | H | CH₂SOCH₃ | 3-CF₃ | 117-121 |
| 8-76 | CH | H | CH₂SO₂CH₃ | 3-CF₃ | 199-201 |
| 8-77 | CH | H | CH₂CH₂SCH₂CH₂CF₃ | 3-CF₃ | 1.5235 (26.1° C.) |

TABLE 16-continued

| Compound No. | A | R$^1$ | R$^7$ | (Z)$_n$ | Physical property |
|---|---|---|---|---|---|
| 8-78 | CH | H | CH$_2$CH$_2$SOCH$_2$CH$_2$CF$_3$ | 3-CF$_3$ | 75-82 |
| 8-79 | CH | H | CH$_2$CH$_2$SO$_2$CH$_2$CH$_2$CF$_3$ | 3-CF$_3$ | 198-201 |
| 8-80 | CH | H | CH$_2$OC(=O)CH$_3$ | 3-CF$_3$ | 176-177 |
| 8-81 | CH | H | CH$_2$CH(OCH$_3$)$_2$ | 3-CF$_3$ | 193-195 |
| 8-82 | CH | H | H$_2$C—(1,3-dioxolan-2-yl) | 3-CF$_3$ | 188-190 |
| 8-83 | CH | H | C(=O)CH$_3$ | 3-CF$_3$ | 184-190 |
| 8-84 | CH | H | C(=O)OCH$_3$ | 3-CF$_3$ | 181-193 |
| 8-85 | CH | H | C(=O)N(CH$_3$)$_2$ | 3-CF$_3$ | 120-131 |
| 8-86 | CH | H | SO$_2$CH$_3$ | 3-CF$_3$ | 178-180 |
| 8-87 | CH | H | CH$_2$CHO | 3-CF$_3$ | 183 |
| 8-88 | CH | H | CH$_2$C(=NOCH$_3$)H | 3-CF$_3$ | 172-182 |
| 8-89 | CH | H | CH$_2$C(=O)OCH$_3$ | 3-CF$_3$ | 120-122 |
| 8-90 | CH | H | CH$_2$C(=O)N(CH$_3$)$_2$ | 3-CF$_3$ | 195-196 |

R$^2$, R$^3$, R$^4$ = H, m = 0

TABLE 17

| Compound No. | A | R$^1$ | R$^7$ | (Z)$_n$ | Physical property |
|---|---|---|---|---|---|
| 8-91 | CH | H | CH$_2$CH$_2$C(=O)NH$_2$ | 3-CF$_3$ | 95-104 |
| 8-92 | CH | H | Me | 4-CF$_3$ | 160 |
| 8-93 | CH | H | H | 2-CF(CF$_3$)$_2$ | 298-300 |
| 8-94 | CH | H | Me | 2-CF(CF$_3$)$_2$ | 168-170 |
| 8-95 | CH | H | CH$_2$C≡CH | 2-CF(CF$_3$)$_2$ | 171-173 |
| 8-96 | CH | H | CH$_2$CN | 2-CF(CF$_3$)$_2$ | 280-283 |
| 8-97 | CH | H | CH$_2$CH$_2$SCH$_3$ | 2-CF(CF$_3$)$_2$ | 161-164 |
| 8-98 | CH | H | CH$_2$CH$_2$SOCH$_3$ | 2-CF(CF$_3$)$_2$ | 1.4288 (19.9° C.) |
| 8-99 | CH | H | CH$_2$CH$_2$SO$_2$CH$_3$ | 2-CF(CF$_3$)$_2$ | 111-114 |
| 8-100 | CH | H | C(=O)CH$_3$ | 2-CF(CF$_3$)$_2$ | 155-157 |
| 8-101 | CH | H | CH$_2$C≡CH | 3-CN | 225-227 |
| 8-102 | CH | H | CH$_2$CN | 3-CN | 234-236 |
| 8-103 | CH | H | Me | 2-NHC(=O)Me | 250-252 |
| 8-104 | CH | H | Me | 2-NHSO$_2$Me | >300 |
| 8-105 | CH | H | Me | 2-N(SO$_2$Me)$_2$ | 228-231 |
| 8-106 | CH | H | Me | 2-C(=O)OMe | 233-234 |
| 8-107 | CH | H | Me | 2-C(=O)OH | >300 |
| 8-108 | CH | H | Me | 2-C(=O)NHSO$_2$CH$_3$ | 202-204 |
| 8-109 | CH | H | Me | 2-SO$_2$CH$_3$ | 267-281 |
| 8-110 | CH | H | Me | 2-SO$_2$CF$_3$ | 187 |
| 8-111 | CH | H | Me | 2-SO$_2$NH$_2$ | 310-312 |
| 8-112 | CH | H | Me | 1-Me | 196-199 |
| 8-113 | CH | H | H | 3-Me | 277-280 |
| 8-114 | CH | H | Me | 3-Me | 174-178 |
| 8-115 | CH | H | CH$_2$CN | 3-Me | NMR |

R$^2$, R$^3$, R$^4$ = H, m = 0

TABLE 18

| Compound No. | A | R$^1$ | R$^7$ | (Z)$_n$ | Physical property |
|---|---|---|---|---|---|
| 8-116 | CH | H | Me | 4-Me | 205-208 |
| 8-117 | CH | H | H | 3-Ph | 294-296 |
| 8-118 | CH | H | CH$_2$C≡CH | 3-Ph | 134-137 |
| 8-119 | CH | H | CH$_2$CN | 3-Ph | 111-115 |
| 8-120 | CH | H | H | 3-CH(OMe)$_2$ | 163-165 |
| 8-121 | CH | H | H | 2-OCH$_2$OCH$_3$ | 262-264 |
| 8-122 | CH | H | Me | 2-OCH$_2$OCH$_3$ | 225-228 |
| 8-123 | CH | H | Me | 2-OH | 293-295 |
| 8-124 | CH | H | Me | 2-OCHF$_2$ | 157-159 |
| 8-125 | CH | H | Me | 2-OCF$_3$ | 169-172 |
| 8-126 | CH | H | Me | 2-NHMe | 251-253 |
| 8-127 | CH | H | Me | 2-NMe$_2$ | 224-226 |
| 8-128 | CH | H | Me | 2-NHC(=O)H | 263-266 |
| 8-129 | CH | H | H | 1,2-F$_2$ | NMR |
| 8-130 | CH | H | Me | 1,2-F$_2$ | 228-233 |
| 8-131 | CH | H | H | 1,3-F$_2$ | >300 |
| 8-132 | CH | H | Me | 1,3-F$_2$ | 268-270 |
| 8-133 | CH | H | CH$_2$CN | 1,3-F$_2$ | 190-191 |
| 8-134 | CH | H | Me | 2,4-F$_2$ | 180-185 |
| 8-135 | CH | H | Me | 2-F, 3-Me | 161-165 |
| 8-136 | CH | H | Me | 1,3-Cl$_2$ | 238-244 |
| 8-137 | CH | H | Me | 2,3-Cl$_2$ | 258-259 |
| 8-138 | CH | H | Me | 2,4-Cl$_2$ | 206-207 |
| 8-139 | CH | H | Me | 2-Cl, 3-Me | 222-227 |
| 8-140 | CH | H | Me | 2-Cl, 3-CF$_3$ | 175-179 |

R$^2$, R$^3$, R$^4$ = H, m = 0

TABLE 19

| Compound No. | A | R$^1$ | R$^7$ | (Z)$_n$ | Physical property |
|---|---|---|---|---|---|
| 8-141 | CH | H | Me | 3,4-Cl$_2$ | 197-199 |
| 8-142 | CH | H | CH$_2$C≡CH | 2-NO$_2$, 3-F | 185-190 |
| 8-143 | CH | H | Me | 2-Me, 3-F | 255-258 |
| 8-144 | CH | H | Me | 2-Me, 3-Cl | 230-232 |
| 8-145 | CH | H | Me | 2-OMe, 3-Cl | 234-237 |
| 8-146 | CH | CF$_3$ | Me | 2-F | 175-178 |
| 8-147 | CF | H | H | H | 186-188 |
| 8-148 | CF | H | Me | H | 212-214 |
| 8-149 | CF | H | CH$_2$C≡CH | H | 153-155 |
| 8-150 | CF | H | CH$_2$CN | H | 243-245 |
| 8-151 | CF | H | CH$_2$OCH$_3$ | H | 157-158 |
| 8-152 | CF | H | H | 2-F | 283-285 |
| 8-153 | CF | H | Me | 2-F | 243-245 |
| 8-154 | CF | H | CH$_2$C≡CH | 2-F | 202-205 |
| 8-155 | CF | H | CH$_2$CN | 2-F | 152-154 |

TABLE 19-continued

| Compound No. | A | R¹ | R⁷ | (Z)ₙ | Physical property |
|---|---|---|---|---|---|
| 8-156 | CF | H | CH₂OCH₃ | 2-F | 114-117 |
| 8-157 | CF | H | H | 1,3-F₂ | 293-296 |
| 8-158 | CF | H | Me | 1,3-F₂ | 253-255 |
| 8-159 | CF | H | CH₂C≡CH | 1,3-F₂ | 167-169 |
| 8-160 | CF | H | CH₂CN | 1,3-F₂ | 236-237 |
| 8-161 | CF | H | CH₂OCH₃ | 1,3-F₂ | 152-154 |
| 8-162 | C—OEt | H | Me | H | 215-217 |
| 8-163 | C—OEt | H | CH₂C≡CH | H | 183-185 |
| 8-164 | C—OEt | H | CH₂CN | H | 124-126 |

R², R³, R⁴ = H,
m = 0

[Chemical 17]

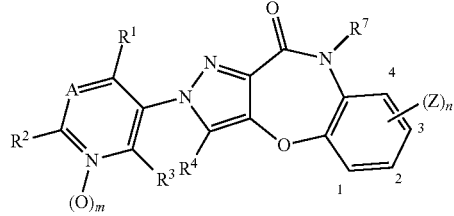

(I-1)

TABLE 20

| Compound No. | A | R² | R⁴ | R⁷ | (Z)ₙ | m | Physical property |
|---|---|---|---|---|---|---|---|
| 9-1 | CH | H | H | Me | H | 1 | 260-262 |
| 9-2 | CH | Cl | H | Me | 2-F | 0 | 190-192 |
| 9-3 | CH | H | F | H | H | 0 | 267-268 |
| 9-4 | CH | H | Cl | H | 2-Cl | 0 | 281-283 |
| 9-5 | CH | H | Cl | CH₂CN | 2-F | 0 | 100-102 |
| 9-6 | CH | H | Cl | H | 2,3-Cl₂ | 0 | >300 |
| 9-7 | CH | H | SO₂Ph | Me | 3-F | 0 | 160-167 |
| 9-8 | CH | H | NH₂ | H | H | 0 | 218-219 |
| 9-9 | CH | H | NH₂ | H | 3-F | 0 | 255-257 |
| 9-10 | CH | H | NHC(=O)Me | H | H | 0 | 241-243 |

R¹, R³ = H

[Chemical 18]

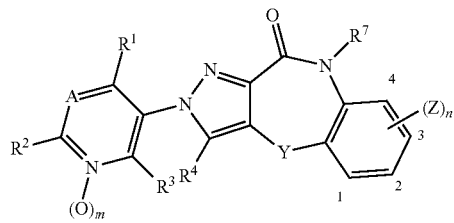

(I-1ʰ)

TABLE 21

| Compound No. | A | Y | R⁷ | (Z)ₙ | Physical property |
|---|---|---|---|---|---|
| 10-1 | CH | NH | H | H | >300 |
| 10-2 | CH | NH | Me | H | 289-290 |
| 10-3 | CH | S | H | H | 256-259 |
| 10-4 | CH | S | Me | H | 226-228 |

TABLE 21-continued

| Compound No. | A | Y | R⁷ | (Z)ₙ | Physical property |
|---|---|---|---|---|---|
| 10-5 | CH | S | CH₂C≡CH | H | 201-202 |
| 10-6 | CH | S | CH₂CN | H | 258-259 |
| 10-7 | CH | S | CH₂OCH₃ | H | 203-205 |

R¹, R², R³, R⁴ = H,
m = 0

[Chemical 19]

(I-1ⁱ)

TABLE 22

| Compound No. | A | X | (Z)ₙ | Physical property |
|---|---|---|---|---|
| 11-1 | CH | Cl | H | 126-128 |
| 11-2 | CH | Cl | 3-F | 185-186 |
| 11-3 | CH | CN | 3-F | 213-214 |
| 11-4 | CH | C≡CSiMe₃ | H | 147-149 |
| 11-5 | CH | NH₂ | H | 190-191 |
| 11-6 | CH | NHMe | 3-F | 175-176 |
| 11-7 | CH | NHc-Pr | H | 112-114 |
| 11-8 | CH | NHCH₂CHF₂ | 3-F | 170-171 |
| 11-9 | CH | NHOH | H | 238-240 |
| 11-10 | CH | NMe₂ | H | 126-128 |
| 11-11 | CH | N(CH₂CH=CH₂)₂ | 3-F | 1.3165 (21.4° C.) |
| 11-12 | CH | N(piperazinyl)—N—Me | H | 179-180 |
| 11-13 | CH | N(piperazinyl)—N—Me | 3-F | 194-196 |
| 11-14 | CH | morpholinyl | H | 177-179 |
| 11-15 | CH | morpholinyl | 3-F | 192-194 |
| 11-16 | CH | OCH₂OCH₃ | H | 78-81 |
| 11-17 | CH | OCH₂CH₂SCH₃ | 2-CF(CF₃)₂ | 99-102 |
| 11-18 | CH | SMe | 3-F | 131-132 |
| 11-19 | CH | SEt | 3-F | 116-118 |

R¹, R², R³, R⁴ = H, m = 0

[Chemical 20]

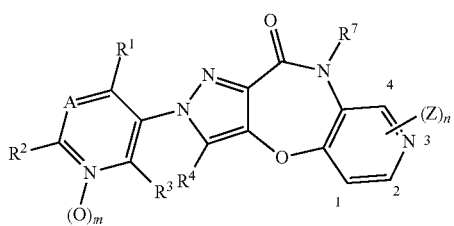

(I-1$^j$)

TABLE 23

| Compound No. | A | R$^7$ | (Z)$_n$ | Physical property |
|---|---|---|---|---|
| 12-1 | CH | Me | H | 254-260 |

R$^1$, R$^2$, R$^3$, R$^4$ = H,
m = 0

[Chemical 21]

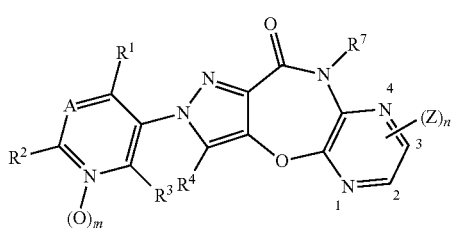

(I-1$^k$)

TABLE 24

| Compound No. | A | R$^7$ | (Z)$_n$ | Physical property |
|---|---|---|---|---|
| 13-1 | CH | Me | H | 296-298 |

R$^1$, R$^2$, R$^3$, R$^4$ = H,
m = 0

[Chemical 22]

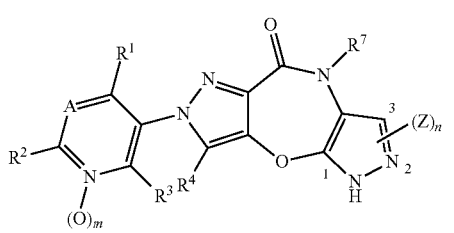

(I-1$^l$)

TABLE 25

| Compound No. | A | R$^7$ | (Z)$_n$ | Physical property |
|---|---|---|---|---|
| 14-1 | CH | H | 1,3-Me$_2$ | 270-272 |
| 14-2 | CH | Me | 1,3-Me$_2$ | 190-192 |
| 14-3 | CH | CH$_2$CH=CH$_2$ | 1,3-Me$_2$ | 1.3071 (25.9° C.) |
| 14-4 | CH | CH$_2$C≡CH | 1,3-Me$_2$ | 172-173 |
| 14-5 | CH | CH$_2$CN | 1,3-Me$_2$ | 133-135 |

R$^1$, R$^2$, R$^3$, R$^4$ = H,
m = 0

[Chemical 23]

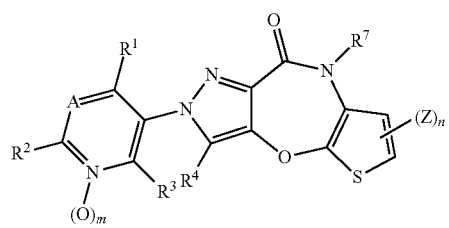

(I-1$^m$)

TABLE 26

| Compound No. | A | R$^7$ | (Z)$_n$ | Physical property |
|---|---|---|---|---|
| 15-1 | CH | H | H | 290-291 |
| 15-2 | CH | Me | H | 208-210 |
| 15-3 | CH | CH$_2$C≡CH | H | 185-186 |
| 15-4 | CH | CH$_2$CN | H | 240-243 |
| 15-5 | CF | H | H | 296-298 |
| 15-6 | CF | Me | H | NMR |
| 15-7 | CF | CH$_2$CN | H | 219-220 |
| 15-8 | CF | CH$_2$OCH$_3$ | H | 165-168 |

R$^1$, R$^2$, R$^3$, R$^4$ = H,
m = 0

An agricultural/horticultural insecticide containing, as its active ingredient, an oxazepine compound or salt thereof expressed by General Formula (I) according to the present invention is suitable for controlling various pest insects, such as agricultural pest insects, forest pest insects, horticultural pest insects, stored-grain pest insects, hygiene pest insects, nematodes, etc., that damage rice, fruit trees, vegetables, and other crops as well as flowers.

Examples of the aforementioned pest insects, nematodes, etc., include the following:

Lepidoptera pest insects include, for example, Aoiraga (*Parasa consocia*),Akakiriba (*Anomis mesogona*), Swallowtail (*Papilio xuthus*), Azukisayamushiga (*Matsumuraeses azukivora*), Azukinomeiga (*Ostrinia scapulalis*), Africa Spodoptera (*Spodoptera exempta*), Fall webworm (*Hyphantria cunea*), European corn borer (*Ostrinia furnacalis*), Armyworm (*Pseudaletia separata*), Clothes moth (*Tinea translucens*), Igusashinmushiga (*Bactra furfurana*), Straight swift (*Parnara guttata*), Inetatehamaki (*Marasmia exigua*), Ineyotou (*Sesamia inferens*), Imokibaga (*Brachmia triannulella*), Slug moth (*Monema flavescens*), Irakusaginuwaba (*Trichoplusia ni*), Ukonnomeiga (*Pleuroptya ruralis*), Umeedashaku (*Cystidia couaggaria*), Uranamishijimi (*Lampides boeticus*), Pellucid hawk moth (*Cephonodes hylas*), Tobacco budworm (*Helicoverpa armigera*), Ootobimonshachihoko (*Phalerodonta manleyi*), Oominoga (*Eumeta japonica*), Large white (*Pieris brassicae*),Lackey moth (*Malacosoma neustria testacea*), Kakinohetamushiga (*Stathmopoda masinissa*), Kakihosoga (*Cuphodes diospyrosella*), Apple leafroller (*Archips xylosteanus*), Turnip moth (*Agrotis segetum*), Kanshoshinkuihamaki (*Tetramoera schistaceana*), Swallowtail butterfly (*Papilio machaon hippocrates*), Macular bat (*Endoclite sinensis*), Ginmonhamoguiga (*Lyonetia prunifoliella*), Kinmonhosoga (*Phyllonorycter ringoneella*), Kurimiga (*Cydia kurokoi*), Kurimidorishinkuiga (*Eucoenogenes aestuosa*), Grape berry moth (*Lobesia botrana*), Kuroshitaaoiraga (*Latoia sinica*), Kurofutamonmadarameiga (*Euzophera batangensis*), Kuwaihosohamaki (*Phalonidia mesotypa*), Mulberry tiger moth (*Spilosoma imparilis*), Kuwanomeiga (*Glyphodes*

*pyloalis*), Kuwahimehamaki (*Olethreutes mori*), Common clothes moth (*Tineola bisselliella*), Swift moth (*Endoclyta excrescens*), European grain moth (*Nemapogon granellus*), Kosukashiba (*Synanthedon hector*), Codling moth (*Cydia pomonella*), Diamondback moth (*Plutella xylostella*), Rice leafroller (*Cnaphalocrocis medinalis*), Southern pink borer (*Sesamia calamistis*), Yellow stem borer (*Scirpophaga incertulas*), Shibatsutoga (*Pediasia teterrellus*), Potato moth (*Phthorimaea operculella*), Lobster moth (*Stauropus fagi persimilis*), Shiroichimonjimadarameiga (*Etiella zinckenella*), Beet armyworm (*Spodoptera exigua*), White ten bat (*Palpifer sexnotata*), Shironayotou (*Spodoptera mauritia*), Rice white giant pyralidae (*Scirpophaga innotata*), Shiromonyaga (*Xestia c-nigrum*), Sujikiriyotou (*Spodoptera depravata*), Mediterranean flour moth (*Ephestia kuehniella*), Orange moth (*Angerona prunaria*), Seguroshachihoko (*Clostera anastomosis*), Soybean looper (*Pseudoplusia includens*), Daizusayamushiga (*Matsumuraeses falcana*), Tobacco budworm (*Helicoverpa assulta*), Tamanaginuwaba (*Autographa nigrisigna*), Black cutworm (*Agrotis ipsilon*), Arna Pseudoconspersa (*Euproctis pseudoconspersa*), Smaller tea tortrix (*Adoxophyes orana*), Tea leafroller (*Caloptilia theivora*), Tea tortrix (*Homona magnanima*), Tobacco moth (*Ephestia elutella*), Chaminoga (*Eumeta minuscula*), Tsumaakashachihoko (*Clostera anachoreta*), Heliothis maritima (*Heliothis maritima*), Tenguhamaki (*Sparganothis pilleriana*), Toumorokoshimeiga (*Busseola fusca*), Tussock (*Euproctis subflava*), Tobimonooedashaku (*Biston robustum*), Tomato fruit worm (*Heliothis zea*), Nakajiroshitaba (*Aedia leucomelas*), Nashiiraga (*Narosoideus flavidorsalis*), Nashikenmon (*Viminia rumicis*), Nashichibiga (*Bucculatrix pyrivorella*), Oriental fruit moth (*Grapholita molesta*), Nashihosoga (*Spulerina astaurota*), Nashimadarameiga (*Ectomyelois pyrivorella*), Rice stem borer (*Chilo suppressalis*), Negikoga (*Acrolepiopsis sapporensis*), Indian meal moth (*Plodia interpunctella*), Haimadaranomeiga (*Hellula undalis*), Angoumois grain moth (*Sitotroga cerealella*), Common cutworm (*Spodoptera litura*), a kind of Tortricid (*Eucosma aporema*), Barahamaki (*Acleris comariana*), Himekuroiraga (*Scopelodes contractus*), Himeshiromondokuga (*Orgyia thyellina*), Fall armyworm (*Spodoptera frugiperda*), Fukinomeiga (*Ostrinia zaguliaevi*), Futaobikoyaga (*Naranga aenescens*), Futatenkagibamodoki (*Andraca bipunctata*), Grape clearwing moth (*Paranthrene regalis*), Grape sparrow (*Acosmeryx castanea*), Grape leafminer (*Phyllocnistis toparcha*), Grape hime moth (*Endopiza viteana*), Grape bombardier moth (*Eupoecillia ambiguella*), Velvet bean caterpillar (*Anticarsia gemmatalis*), Hosobahaiirohamaki (*Cnephasia cinereipalpana*), Gypsy moth (*Lymantria dispar*), Pine moth (*Dendrolimus spectabilis*), Soybean pod borer (*Leguminivora glycinivorella*), Legume pod borer (*Maruca testulalis*), Mamehimesayamushiga (*Matsumuraeses phaseoli*), Mamehosoga (*Caloptilia soyella*), Citrus leafminer (*Phyllocnistis citrella*), Maeusukinomeiga (*Omiodes indicata*), Midarekakumonhamaki (*Archips fuscocupreanus*), Mitsumonkinuwaba (*Ctenoplusis agnata*), Minoga (*Bambalina* sp.), Momoshinkuiga (*Carposina niponensis*), Momonogomadaranomeiga (*Conogethes punctiferalis*), Momosukashiba (*Synanthedon* sp.), Momohamoguriga (*Lyonetia clerkella*), Monkiageha (*Papilio helenus*), Eastern pale clouded yellow (*Colias erate poliographus*), Monkuroshachihoko (*Phalera flavescens*), Cabbage butterfly (*Pieris rapae crucivora*), White butterfly such as cabbage butterfly (*Pieris rapae*), Gold-tail (*Euproctis similis*), Yamanoimokoga (*Acrolepiopsis suzukiella*), European corn borer (*Ostrinia nubilalis*), Cabbage armyworm (*Mamestra brassicae*), Yomogiedashaku (*Ascotis selenaria*), Yomogioohosohamaki (*Phtheochroides clandestina*), Ringooohamaki (*Hoshinoa adumbratana*), Ringokareha (*Odonestis pruni japonensis*), Ringokenmon (*Triaena intermedia*), Ringokokakumonhamaki (*Adoxophyes orana fasciata*), Ringokoshinkui (*Grapholita inopinata*), Ringoshirohimehamaki (*Spilonota ocellana*), Ringohaiirohamaki (*Spilonota lechriaspis*), Ringohamakikuroba (*Illiberis pruni*), Ringohimeshinkui (*Argyresthia conjugella*), Ringohosoga (*Caloptilia zachrysa*), Ringomonhamaki (*Archips breviplicanus*), Wataakakiriba (*Anomis flava*), Pink bollworm (*Pectinophora gossypiella*), Watanomeiga (*Notarcha derogata*), Wataherikuronomeiga (*Diaphania indica*), Tobacco budworm (*Heliothis virescens*), Wataringa (*Earias cupreoviridis*), and the like.

Hemiptera pest insects include, for example, Blue grasses stink bug (*Nezara antennata*), Akasujikasumikame (*Stenotus rubrovittatus*), Red streaks stink bug (*Graphosoma rubrolineatum*), Akahigehosomidorikasumikame (*Trigonotylus coelestialium*), etc., Akahimeherikamemushi (*Aeschynteles maculatus*), Akahoshikasumikame (*Creontiades pallidifer*), Red-spotted stink bug (*Dysdercus cingulatus*), Akahoshimarukaiagaramushi (*Chrysomphalus ficus*), California red scale (*Aonidiella aurantii*), Large brown cicada (*Graptopsaltria nigrofuscata*), Chinch bug (*Blissusleucopterus*), Iseriya scale insects (*Icerya purchasi*), Unibanded stink bug (*Piezodorus hybneri*), Inekamemushi (*Lagynotomus elongatus*), Inekiirohimeyokobai (*Thaia subrufa*), Inekurokamemushi (*Scotinophara lurida*), Thorns aphid (*Sitobion ibarae*), Iwasaki stink bug (*Stariodes iwasakii*), Usuiromarukaigaramushi (*Aspidiotus destructor*), Usumonmidorikasumikame (*Taylorilygus pallidulus*), Umekobuaburamushi (*Myzusmumecola*), Plum white scale insects (*Pseudaulacaspis prunicola*), Pea aphid (*Acyrthosiphon pisum*), Okumoherikamemushi (*Anacanthocoris striicornis*), Okurotobikasumikame (*Ectometopterus micantulus*), Otogeshirahoshikamemushi (*Eysarcoris lewisi*), Oherikamemushi (*Molipteryx fuliginosa*), Ooyokobai (*Cicadella viridis*), Okabonoakaaburamushi (*Rhopalosophum rufiabdominalis*), Oribukatakaigaramushi (*Saissetia oleae*), Greenhouse whitefly (*Trialeurodes vaporariorum*), Kashihimeyokobai (*Aguriahana quercus*), Kasumi stink bugs (*Lygus* spp.), Kabawatafukimadaraaburamushi (*Euceraphis punctipennis*), Kankitsukaigaramushi (*Andaspis kashicola*), Kankitsukatakaigaramushi (*Coccus pseudomagnoliarum*), Kanshakobanenagakamemushi (*Cavelerius saccharivorus*), Kikugunbai (*Galeatus spinifrons*), Kikuhimehigenagaaburamushi (*Macrosiphoniella sanborni*), Kimarukaigaramushi (*Aonidiella citrina*), Brown marmorated stink bug (*Halyomorpha mista*), Kusugunbai (*Stephanitis fasciicarina*), Kusutogarikijirami (*Trioza camphorae*), Kumoherikamemushi (*Leptocorisa chinensis*), Kuritogarikijirami (*Trioza quercicola*), Kurumigunbai (*Uhlerites latius*), Grape leaf hopper (*Erythroneura comes*), Kuroashihosonagakamemushi (*Paromius exiguus*), Kurokatamarukaigaramushi (*Duplaspidiotus claviger*), Kurosujitsumaguroyokobai (*Nephotettix nigropictus*), Kurotobikasumikame (*Halticiellus insularis*), Kurofutsunounka (*Perkinsiella saccharicida*), Kuroringokijirami (*Psylla malivorella*), Mulberry psyllid (*Anomoneurs mori*), Comstock mealybug (*Pseudococcus longispinis*), Mulberry white scale insects (*Pseudaulacaspis pentagona*), White peach scale insects (*Pulvinaria kuwacola*), Koaokasumikame (*Apolygus lucorum*), Kobanehyotannagakamemushi (*Togo hemipterus*), Komikanaburamushi (*Toxoptera aurantii*), Satokibikonakaigaramushi (*Saccharicoccus sacchari*), Satokibinewatamushi (*Geoica lucifuga*), Satonousuirounka (*Numata muiri*), Sanhozekaigaramushi (*Comstockaspis perniciosa*), Citrus snow scale (*Unaspis citri*), Potato aphid (*Aulacorthum solani*), Shirahoshi stink bug (*Eysarcoris ventralis*), Silverleaf whitefly (*Bemisia argentifolii*), Shiroooyokobai (*Cicadella spectra*), Shiromarukaigaramushi (*Aspidiotus hederae*), Sukashihimeherikamemushi (*Liorhyssus hyalinus*), Segurohimekijirami (*Calophya nigridorsalis*), Sejirounka (*Sogatella furcifera*), Broad bean aphid (*Megoura crassicauda*), Radish aphid (*Brevicoryne brassicae*), Soybean aphid (*Aphis glycines*), Taiwankumoherikamemushi (*Leptocorisa oratorius*), Taiwantsumaguroyokobai (*Nephotettix virescens*), Taiwanhigenagaaburamushi (*Uroeucon formosanum*), Tabakokasumikame (*Cyrtopeltis tennuis*), Tabakokonajirami (*Bemisia tabaci*), Chanokatakaigaramushi (*Lecanium persicae*), Chanokurohoshikaigaramushi (*Parlatoria theae*), Chanomarukaigaramushi (*Pseudaonidia paeoniae*), Chanomidorihimeyokobai (*Empoasca onukii*), Chabaneaokamemushi (*Plautia stali*), Churippuneaburamushi (*Dysaphis tulipae*), Churippuhigenagaaburamushi (*Macrosiphum euphorbiae*), Tsutsujigunbai (*Stephanitis pyrioides*), Tsunoroumushi (*Ceroplastes ceriferus*), Tsubakikurohoshikaigaramushi (*Parlatoria camelliae*), Tsumaguroaokasumikame (*Apolygus spinolae*), Green rice leafhopper (*Nephotettix cincticeps*), Tsuyaaokamemushi (*Glaucias subpunctatus*), Tensaikasumikame (*Orthotylus flavosparsus*), Corn aphid (*Rhopalosiphum maidis*), Corn planthopper (*Peregrinus maidis*), Togeshirahoshikamemushi (*Eysarcoris parvus*), bed bugs (*Cimex lectularius*), Todokijirami (*Psylla abieti*), Brown planthopper (*Nilaparvata lugens*), Toberakijirami (*Psylla tobirae*), Nagame (*Eurydema rugosum*), Pear aphid (*Schizaphis piricola*), Nashikijirami (*Psylla pyricola*), Nashikurohoshikaigaramushi (*Parlatoreopsis pyri*), Nashigunbai (*Stephanitis nashi*), Nashikonakaigaramushi (*Dysmicoccus wistariae*), Nashishironagakaigaramushi (*Lepholeucaspis japonica*), Nashimaruaburamushi (*Sappaphis piri*), Turnip aphid (*Lipaphis erysimi*), Green onion aphid (*Neotoxoptera formosana*), Hasukubireaburamushi (*Rhopalosophum nymphaeae*), Rose leafhopper (Edwardsianarosae), Harannagakaigaramushi (Pinnaspisaspidistrae), Hannokijirami (*Psylla alni*), Hannonagayokobai (*Speusotettix subfusculus*), Hannohimeyokobai (*Alnetoidia alneti*), Hieunka (*Sogatella panicicola*), Higenagakasumikame (*Adelphocoris lineolatus*), Himeakahoshikamemushi (*Dysdercus poecilus*), Himekurokaigaramushi (*Parlatoria ziziphi*), Himegunbai (*Uhlerites debilis*), Small brown planthopper (*Laodelphax striatella*), Himenagame (*Eurydema pulchrum*), Himeharikamemushi (*Cletus trigonus*), Himefutatennagaawafuki (*Clovia punctata*), Himeyokobai (*Empoasca* sp.), Hiratakataigaramushi (*Coccus hesperidum*), Hiratahyotannagakamemushi (*Pachybrachius luridus*), Fujikonakaigaramushi (*Planococcus kraunhiae*), Futasujikasumikame (*Stenotus binotatus*), Futatenhimeyokobai (*Arboridia apicalis*), Futatenyokobai (*Macrosteles fascifrons*), Buchihigekamemushi (*Dolycoris baccarum*), Buchihigekurokasumikame (*Adelphocoris triannulatus*), Phylloxera (*Viteus vitifolii*), Ground cherry stink bug (*Acanthocoris sordidus*), Hosokumoherikamemushi (*Leptocorisa acuta*), Hosokobanenagakamemushi (*Macropes obnubilus*), Hosoharikamemushi (*Cletus punctiger*), Hosoherikamemushi (*Riptortus clavatus*), Potetopishirido (*Paratrioza cockerelli*), Maekiawafuki (*Aphrophora costalis*), Makibakasumikame (*Lygus disponsi*), Madarakasumikame (*Lygus saundersi*), Matsukonakaigaramushi (*Crisicoccus pini*), Pine leafhopper (*Empoasca abietis*), Matsumotokonakaigaramushi (*Crisicoccus matsumotoi*), Bean aphid (*Aphis craccivora*), Plataspid bug (*Megacopta punctatissimum*), Marushirahoshikamemushi (*Eysarcoris guttiger*), Purple scale insects (*Lepidosaphes beckii*), Mikankijirami (*Diaphorina citri*), Mikankuroaburamushi (*Toxoptera citricidus*), Mikankonakaigaramushi (*Planococcus citri*), Citrus whitefly (*Dialeurodes citri*), Orange spiny whitefly (*Aleurocanthus spiniferus*), Mikanhimekonakaigaramushi (*Pseudococcus citriculus*), Mikanhimeyokobai (*Zyginella citri*), Mikanhimewatakaigaramushi (*Pulvinaria citricola*), Mikanhiratakaigaramushi (*Coccus discrepans*), Mikanmarukaigaramushi (*Pseudaonidia duplex*), Mikanwatakaigaramushi (*Pulvinaria aurantii*), Mizukikatakaigaramushi (*Lecanium corni*), Southern blue stink bug (*Nezara viridula*), Mugikasumikame (*Stenodema calcaratum*), Mugikubireaburamushi (*Rhopalosiphum padi*), Mugihigenagaaburamushi (*Sitobion akebiae*), Wheat green aphid (*Schizaphis graminum*), Mugiyokobai (*Sorhoanus tritici*), Mugiwaragikuomaruaburamushi (*Brachycaudus helichrysi*), Purple stink bug (*Carpocoris purpureipennis*), Green peach aphid (*Myzus persicae*), Momokofukiaburamushi (*Hyalopterus pruni*), Yanagiaburamushi (*Aphis farinose yanagicola*), Yanagigunbai (*Metasalis populi*), Yanonekaigaramushi (*Unaspis yanonensis*), Yamaasakijirami (*Mesohomotoma camphorae*), Yukiyanagiaburamushi (*Aphis spiraecola*), Apple aphid (*Aphis pomi*), Oystershell scale insects (*Lepidosaphes ulmi*), Ringokijirami (*Psylla mali*), Ringokurokasumikame (*Heterocordylus flavipes*), Ringokobuaburamushi (*Myzus malisuctus*), Ringoneaburamushi (*Aphidonuguis mali*), Ringomadarayokobai (*Orientus ishidai*), Apple green aphid (*Ovatus malicolens*), Woolly apple aphid (*Eriosomalanigerum*), Rubiroumushi (*Ceroplastes rubens*), Cotton aphid (*Aphis gossypii*), and the like.

Coleoptera pest insects include, for example, Aosujikamikiri (*Xystrocera globosa*), Aobaarigatahanekakushi (*Paederus fuscipes*), Aohanamuguri (*Eucetonia roelofsi*), Adzuki bean weevil (*Callosobruchus chinensis*), Sweet potato weevil (*Cylas formicarius*), alfalfa weevil (*Hypera postica*), Rice plant weevil (*Echinocnemus squameus*), Inedorooimushi (*Oulema oryzae*), Inenekuihamushi (*Donacia provosti*), Rice water weevil (*Lissorhoptrus oryzophilus*), Imosaruhamushi (*Colasposoma dauricum*), Imozoumushi (*Euscepes postfasciatus*), Mexican bean beetle (*Epilachna varivestis*), Common beans weevil (*Acanthoscelides obtectus*), Western corn rootworm (*Diabrotica virgifera virgifera*), Umechokkirizoumushi (*Involvulus cupreus*), Cucurbit leaf beetle (*Aulacophora femoralis*), Pea weevil (*Bruchus pisorum*), Oonijyuyahoshitentou (*Epilachna vigintioctomaculata*), Corn-sap beetle (*Carpophilus dimidiatus*), Tortoise beetle (*Cassida nebulosa*), Kiashinomihamushi (*Luperomorpha tunebrosa*), Striped flea beetle (*Phyllotreta striolata*), Kiboshikamikiri (*Psacothea hilaris*), Kimadarakamikiri (*Aeolesthes chrysothrix*), Chestnut weevil (*Curculio sikkimensis*), Dried-fruit beetle (*Carpophilus hemipterus*), Koaohanamuguri (*Oxycetonia jucunda*), Corn rootworm (*Diabrotica* spp.), Gold beetles (*Mimela splendens*), Maize weevil (*Sitophilus zeamais*), Red flour beetle (*Tribolium castaneum*), Rice weevil (*Sitophilus oryzae*), Kohimekokunusutomodoki (*Palorus subdepressus*), Melolonthid (*Melolontha japonica*), Gomadarakamikiri (*Anoplophora malasiaca*), Mealworm (*Neatus picipes*), Colorado potato beetle (*Leptinotarsa decemlineata*), Southern corn rootworm (*Diabrotica undecimpunctata howardi*), Shibaosazoumushi (*Sphenophorus venatus*), Jyushihoshikubinagahamushi (*Crioceris quatuordecimpunctata*), Plums weevil (*Conotrachelus nenuphar*), Daikonsaruzoumushi (*Ceuthorhynchidius albosuturalis*), Radish leaf beetle (*Phaedon brassicae*), Tabakoshibanmushi (*Lasioderma serricorne*), Chibikofukizoumushi (*Sitona japonicus*), Chairokogane (*Adoretus tenuimaculatus*), Chirokomenogomumushidamashi (*Tenebrio molitor*), Chirosaruhamushi (*Basilepta balyi*), Tsumekusatakozoumushi (*Hypera nigrirostris*), Tensaitobihamushi (*Chaetocnema concinna*), Cupreous chafer (*Anomala cuprea*), Nagachakogane (*Heptophylla picea*), Nijuuyahoshi beetle (*Epilachna vigintioctopunctata*), Northern corn rootworm (*Diabrotica longicornis*), Flower beetle (*Eucetonia pilifera*), Wireworms (*Agriotes* spp.), Himekatsuobushimushi (*Attagenus unicolor japonicus*), Himekibanesaruhamushi (*Pagria signata*), Rufocuprea (*Anomala rufocuprea*), Himekokunusutomodoki (*Palorus ratzeburgii*), Himegomimushidamashi (*Alphitobius laevigatus*), Himemaru carpet beetle (*Anthrenus verbasci*), Hiratakikuimushi (*Lyctus brunneus*), Confused flour beetle (*Tribolium confusum*), Futasujihimehamushi (*Medythia nigrobilineata*), Budoutorakamikiri (*Xylotrechus pyrrhoderus*), Potato free Beetle (*Epitrix cucumeris*), Pine bark beetle (*Tomicus piniperda*), Japanese pine sawyer (*Monochamus alternatus*), Japanese beetle (*Popillia japonica*), Beans tiger beetle (*Epicauta gorhami*), Maize weevil (*Sitophilus zeamais*), Momochokkirizoumushi (*Rhynchites heros*), Vegetable weevil (*Listroderes costirostris*), Cowpea weevil (*Callosobruchus maculatus*), Ringokofukizoumushi (*Phyllobius armatus*), Ringohanazoumushi (*Anthonomus pomorum*), Rurihamushi (*Linaeidea aenea*), Boll weevil (*Anthonomus grandis*), and the like.

Diptera pest insects include, for example, Common house mosquito (*Culex pipiens pallens*), Beetfly (*Pegomya hyoscyami*), Ashigurohamoguribae (*Liriomyza huidobrensis*), Housefly (*Musca domestica*), Inekimoguribae (*Chlorops oryzae*), Inekukimigiwabae (*Hydrellia sasakii*), Rice leafminer (*Agromyza oryzae*), Inehime leafminer (*Hydrellia griseola*), Ingenmoguribae (*Ophiomyia phaseoli*), Melon fly (*Dacus cucurbitae*), Spotted-wing drosophila (*Drosophila suzukii*), Outouhamadaramibae (*Rhacochlaena japonica*), Ooiebae (*Muscina stabulans*), Nomibae such as Okimonnomibae (*Megaselia spiracularis*), Oochobae (*Clogmia albipunctata*), Kiriujikagambo (*Tipula aino*), Kurokinbae (*Phormia regina*), Kogataakaieka (*Culex tritaeniorhynchus*), Chinese anopheles (*Anopheles sinensis*), Daikonbae (*Hylemya brassicae*), Soybean pod gall midge (*Asphondylia* sp.),Seed-corn fly (*Delia platura*), Onion maggot (*Delia antiqua*), European cherry fruit fly (*Rhagoletis cerasi*), Autogenic house mosquito (*Culex pipiens molestus* Forskal), Mediterranean fruit fly (*Ceratitis capitata*), Chibikurobanekinokobae (*Bradysia agrestis*), Tensaimogurihanabae (*Pegomya cunicularia*), Tomato leafminer (*Liriomyza sativae*), Eggplant leafminer (*Liriomyza bryoniae*), Namoguribae (*Chromatomyia horticola*), Green onion leafminer (*Liriomyza chinensis*), Tropical house mosquitos (*Culex quinquefasciatus*), Yellow-fever mosquitos (*Aedes aegypti*), Tiger mosquito (*Aedes albopictus*), Beans leafminer (*Liriomyza trifolii*), Oriental fruit fly (*Dacus dorsalis*), Mikanbae (*Dacus tsuneonis*), Wheat red gall midge (*Sitodiplosis mosellana*), Mugikimoguribae (*Meromuza nigriventris*), Mexican fruit fly (*Anastrepha ludens*), Apple maggot fly (*Rhagoletis pomonella*), and the like.

Hymenoptera pest insects include, for example, Amimeari (*Pristomyrmex pungens*), Bethylidae such, Little black ant (*Monomorium pharaonis*), Oozuari (*Pheidole noda*), Kaburahabachi (*Athalia rosae*), Chestnut gall wasp (*Dryocosmus kuriphilus*), Negro ant (Formica *fusca japonica*), Vespids, Black-backed turnip sawfly (*Athalia infumata infumata*), Churenji sawfly (*Arge pagana*), Japanese neep sawfly (*Athalia japonica*), Leaf-cutting ant (*Acromyrmex* spp.), Fire ant (*Solenopsis* spp.), Ringohabachi (*Arge mali*), Ruriari (*Ochetellus glaber*), and the like Orthoptera pest insects include, for example, *Ruspolia lineosa* (*Homorocoryphus lineosus*), Mole cricket (*Gryllotalpa* sp.), Koinago (*Oxya hyla intricata*), Kobaneinago (*Oxya yezoensis*), migratory locust (*Locusta migratoria*), Hanenagainago (*Oxya japonica*), Himekusakiri (*Homorocoryphus jezoensis*), Emmakoorogi (*Teleogryllus emma*), and the like.

Thysanoptera pest insects include, for example, Akaobi thrips (*Selenothrips rubrocinctus*), Rice thrips (*Stenchaetothrips biformis*), Inekuda thrips (*Haplothrips aculeatus*), Kakikuda thrips (*Ponticulothrips diospyrosi*), Kiirohana thrips (*Thrips flavus*), Kusakiiro thrips (*Anaphothrips obscurus*), Kusukuda thrips (*Liothrips floridensis*), Gladiolus thrips (*thrips simplex*), Kurogehana thrips (*thrips nigropilosus*), Croton thrips (*Heliothrips haemorrhoidalis*), Mulberry thrips (*Pseudodendrothrips mori*), Cosmos thrips (*Microcephalothrips abdominalis*), Shiionagakuda thrips (*Leeuwenia pasanii*), Shiimarukuda thrips (*Litotetothrips pasaniae*), Citrus thrips (*Scirtothrips citri*), Sinakuda thrips (*Haplothrips chinensis*), Daizu thrips (*Mycterothrips glycines*), Daizuusuiro thrips (*thrips setosus*), Chanokiiro thrips (*Scirtothrips dorsalis*), Chanokuro thrips (*Dendrothrips minowai*), Tsumekusakuda thrips (*Haplothrips niger*), Negi thrips (*Thrips tabaci*), Negikuro thrips (*Thrips alliorum*), Hana thrips (*Thrips hawaiiensis*), Hana Kuda thrips (*Haplothrips kurdjumovi*), Higebuto thrips (*Chirothrips manicatus*), Hirazuhanaazamiuma (*Frankliniella intonsa*), Loquat Hana thrips (*Thrips coloratus*), Western flower thrips (*Franklinella occidentalis*), Minamikiiro thrips (*Thrips palmi*), Yurikiiro thrips (*Frankliniella lilivora*), Yurinokuda thrips (*Liothrips vaneeckei*), and the like.

Acari pest insects include, for example, Blue chiggers (*Leptotrombidium akamushi*), Ashinowahadani (*Tetranychus ludeni*), American dock tick (*Dermacentor variabilis*), Ishiinami spider mites (*Tetranychus truncatus*), House dust mite (*Ornithonyssus bacoti*), Inunikibidani (*Demodex canis*), Cherry spider mites (*Tetranychus viennensis*), Kanzawa spider mite (*Tetranychus kanzawai*), ticks such as Kuriirokita tick (*Rhipicephalus sanguineus*), Stag tsumedani (*Cheyletus malaccensis*), *Tyrophagus dimidiatus* (*Tyrophagus putrescentiae*), Konahyouhidani (*Dermatophagoides farinae*), Redback spider (*Latrodectus hasseltii*), Taiwankaku ticks (*Dermacentor taiwanicus*), Chanonagasabi mite (*Acaphylla theavagrans*), Chanohokoridani (*Polyphagotarsonemus latus*), Tomatosabi mite (*Aculops lycopersici*), Northern fowl mite (*Ornithonyssus sylviarum*), Two-spotted spider mite (*Tetranychus urticae*), Nisenashisabi mite (*Eriophyes chibaensis*), Scabies mites (*Sarcoptes scabiei*), Futatogechima mite (*Haemaphysalis longicornis*), Black leged tick (*Ixodes scapularis*), *Tyrophagus dimidiatus* (*Tyrophagus similis*), Hosotsumedani (*Cheyletus eruditus*), Citrus red mite (*Panonychus citri*), Minami tsumedani (*Cheyletus moorei*), Minami hime spider mites (*Brevipalpus phoenicis*), Mimihizen mites (*Otodectes cynotis*), European house dust mite (*Dermatophagoides pteronyssinus*), Yamatochimadani (*Haemaphysalis flava*), Ixodes ovatus (*Ixodes ovatus*), Ryukyu tangerine rust mite (*Phyllocoptruta citri*),Apple rust mite (*Aculus schlechtendali*), European red mite (*Panonychus ulmi*), Loan star tick (*Amblyomma americanum*), Chicken mites (*Dermanyssus gallinae*), Robinnedani (*Rhyzoglyphus robini*), a kind of Nedanimodoki (*Sancassania* sp.), and the like.

Isoptera pest insects include, for example, Amami termite (*Reticulitermes miyatakei*), the United States drywood termites (*Incisitermes minor*), Formosan subterranean termite (*Coptotermes formosanus*), giant termite (*Hodotermopsis japonica*), Kanmon termite (*Reticulitermes* sp.), Kiashishiroari (*Reticulitermes flaviceps amamianus*), Kushimoto termite (*Glyptotermes kushimensis*), Koushu formosan subterranean termite (*Coptotermes guangzhoensis*), Koushun termite (*Neotermes koshunensis*), Kodama termite (*Glyptotermes kodamai*), Satsuma termite (*Glyptotermes satsumensis*), Daikoku termite (*Cryptotermes domesticus*), Taiwan termite (*Odontotermes formosanus*), Nakajima termite (*Glyptotermes nakajimai*), Nitobe termite (*Pericapritermes nitobei*), Yamato termite (*Reticulitermes speratus*), and the like.

Blattodea pest insects include, for example, Smokybrown cockroach (*Periplaneta fuliginosa*), German cockroach (*Blattella germanica*), Oriental cockroach (*Blatta orientalis*), Brown cockroach (*Periplaneta brunnea*), Hime German cockroach (*Blattella lituricollis*), Japanese cockroach (*Periplaneta japonica*), American cockroach (*Periplaneta americana*), and the like.

Siphonaptera pest insects include, for example, Human flea (*Pulex irritans*), Cat flea (*Ctenocephalides felis*), Chicken flea (*Ceratophyllus gallinae*), and the like.

Nematodes include, for example, Strawberry nematode (*Nothotylenchus acris*), Ineshingare nematode (*Aphelenchoides besseyi*), Northern meadow nematode (*Pratylenchus penetrans*), Northern root-knot nematode (*Meloidogyne hapla*), Sweet potato root-knot nematode (*Meloidogyne incognita*), Potato cyst nematode (*Globodera rostochiensis*), Java root-knot nematode (*Meloidogyne javanica*), Soybean cyst nematode (*Heterodera glycines*), Southern meadow nematode (*Pratylenchus coffeae*), Wheat meadow nematode (*Pratylenchus neglectus*), Mandarin orange root nematodes (*Tylenchus semipenetrans*), and the like.

Molluscs include, for example, Apple snail (*Pomacea canaliculata*), Giant African snail (*Achatina fulica*), Slugs (*Meghimatium bilineatum*), Chaco slug (*Lehmannina valentiana*), Kouranamekuji (*Limax flavus*), Siebold s globular snail (*Acusta despecta sieboldiana*), and the like.

In addition, the agricultural/horticultural insecticide proposed by the present invention has strong insecticidal effects on other pest insects such as tomato leaf miner (*Tuta absoluta*).

In addition, zoobiotic mites, which can also be controlled, include, for example, ticks such as *Rhipicephalus microplus* (*Boophilus microplus*), Kuriiro koitamadani (*Rhipicephalus sanguineus*), Futatogechimadani (*Haemaphysalis longicornis*), Kichimadani (*Haemaphysalis flava*), Adenophora chimadani (*Haemaphysalis campanulata*), Isukachimadani (*Haemaphysalis concinna*), Yamatochimadani (*Haemaphysalis japonica*), Higenagachimadani (*Haemaphysalis kitaokai*), Iyasuchi tick (*Haemaphysalis ias*), Yamato tick (*Ixodes ovatus*), Tanegata tick (*Ixodes nipponensis*), Schulze ticks (*Ixodes persulcatus*), Takasago Kirara ticks (*Amblyomma testudinarium*), Ootogechimadani (*Haemaphysalis megaspinosa*), Aminokaku ticks (*Dermacentor reticulatus*), and Taiwan Kaku ticks (*Dermacentor taiwanesis*), Torisashidani such as Chicken mites (*Dermanyssus gallinae*), Northern fowl mite (*Ornithonyssus sylviarum*), and Sthouthern fowl mite (*Ornithonyssus bursa*), chiggers, such as Nanyo chiggers (*Eutrombicula wichmanni*), Scrub typhus mite (*Leptotrombidium akamushi*), Off thorns chiggers (*Leptotrombidium pallidum*), Fuji chiggers (*Leptotrombidium fuji*), Tosa chiggers (*Leptotrombidium tosa*), Europe Aki mite (*Neotrombicula autumnalis*), America chiggers (*Eutrombicula alfreddugesi*), and Miyagawa Tama chiggers (*Helenicula miyagawai*), Tsumedani such as Inutsumedani (*Cheyletiella yasguri*), Rabbit tsumedani (*Cheyletiella parasitivorax*), and Nekotsumedani (*Cheyletiella blakei*), Sarcoptes such as Rabbit mite (*Psoroptes cuniculi*), Ushishokuhidani (*Chorioptes bovis*), Dog ear mites (*Otodectes cynotis*), Itch mite (*Sarcoptes scabiei*), and Cat foraminous mites (*Notoedres cati*), Demodex such as Inunikibidani (*Demodex canis*) kind, and the like.

Fleas, which can also be controlled, include, for example, ectoparasitic apterous insects in the Siphonaptera order, or specifically, fleas belonging to the Pulicidae family and Ceratephyllus family, among others. Fleas belonging to the Pulicidae family include, for example, Dog flea (*Ctenocephalides canis*), Cat flea (*Ctenocephalides felis*), Human flea (*Pulex irritans*), Sticktight flea (*Echidnophaga gallinacea*), Cheops rat flea (*Xenopsylla cheopis*), Mole rat flea (*Leptopsylla segnis*), Europe rat flea (*Nosopsyllus fasciatus*), Yamato rat flea (*Monopsyllus anisus*), and the like.

Furthermore, other external parasites that can be controlled include, for example, lice such as Short-nosed cattle louse (*Haematopinus eurysternus*), Umajirami (*Haematopinus asini*), Hitsujijirami (*Dalmalinia ovis*), Ushihosojirami (*Linognathus vituli*), Pig louse (*Haematopinus suis*), Pubic louse (*Phthirus pubis*), and Head lice (*Pediculus capitis*), Body louse such as Inuhajirami (*Trichodectes canis*), and other blood-sucking diptera pest insects, such as Horsefly (*Tabanus trigonus*), Uainukaka (*Culicoides schultzei*), Tsumetogebuyu (*Simulium ornatum*), and the like. Also, internal parasites include, for example, lungworms, whipworms, nodular worms, gastric parasites, round worms, filiform insects and other nematodes; *Diphyllobothrium mansoni, Diphyllobothurium latum, Dipylidium caninum, Taenia multiceps, Echinococcus granulosus, Echinococcus multilocularis* and other cestodes; *Schistosomiasis japonica, Fasciola hepatica* and other trematodes; coccidium, malaria parasite, chounainikuhoushichu, *Toxoplasma gondii, Cryptosporidium* and other protozoans, etc.

Since an agricultural/horticultural insecticide that contains, as its active ingredient, an oxazepine compound or salt thereof expressed by General Formula (I) according to the present invention has a remarkable effect of controlling the aforementioned pest insects that damage paddy crops, field crops, fruit trees, vegetables, and other crops as well as flowers, it can be applied in or on nurseries, rice paddies, crop fields, fruit trees, vegetables and other crops, flowers, etc., and their seeds, water in rice paddies, stems and leaves, soil and other cultivation carriers, etc., when pest insects are expected to generate, before pest insects generate, or when their generation is confirmed, and the agricultural/horticultural insecticide proposed by the present invention will achieve the specified effects. In particular, a preferred mode of use is one that utilizes the so-called "penetration migration characteristics," which involves application to the soil at nurseries for crops, flowers, etc., soil around planting holes used for transplantation, plant roots, irrigation water, water used for hydroponic farming, etc., so that the compound proposed by the present invention will be absorbed through the soil, or from the roots without going through the soil.

Useful plants on which the agricultural/horticultural insecticide proposed by the present invention can be used are not limited in any way, and examples include grains (such as rice, barley, wheat, rye, oats, corn, etc.), beans (soybeans, azuki beans, broad beans, peas, kidney beans, peanuts, etc.), fruit trees/fruits (apple, citrus, pear, grapes, peach, plum, yellow peach, walnuts, chestnuts, almonds, bananas, etc.), leafy/fruit vegetables (cabbage, tomatoes, spinach, broccoli, lettuce, onions, green onions (chives, wakegi), bell peppers, eggplant, strawberries, peppers, okra, leeks, etc.), root vegetables (carrots, potatoes, sweet potatoes, taro, daikon radish, turnips, lotus root, burdock, garlic, shallots, etc.), crops for processing (cotton, hemp, beets, hops, sugar cane, sugar beets, olives, gum, coffee, tobacco, tea, etc.), gourds (pumpkins, cucumbers, watermelon, oriental melons, melons, etc.), pasture grass (orchard grass, sorghum, timothy, clover, alfalfa, etc.), lawn (Korean lawn, bent grass, etc.), herbs and other ornamental crops (lavender, rosemary, thyme, parsley, pepper, ginger, etc.), flowers (chrysanthemums, roses, carnations, orchids, tulips, lilies, etc.), garden trees (ginkgo, cherry, Japanese laurel, etc.), forest trees (fir, Japanese spruce, pine, hiba, cedar, hinoki, *eucalyptus*, etc.), and other plants.

The aforementioned "plants" include plants to which resistance to isoxaflutole and other HPPD inhibitors, imazethapyr, thifensulfuron methyl, and other ALS inhibitors, glyphosate and other EPSP synthetic enzyme inhibitors, glufosinate and other glutamine synthetic enzyme inhibitors, sethoxydim and other acetyl CoA carboxylase inhibitors, and bromoxynil, dicamba, 2,4-D, and other herbicides, has been provided by traditional breeding methods or genetic modification engineering.

Examples of "plants" to which resistance has been provided by traditional breeding methods include rapeseed, wheat, sunflower, and rice resistant to imazethapyr and other imidazolinone ALS inhibitor-type herbicides, such as those currently sold under the product name Clearfield (registered trademark). Also, a soybean that has been made resistant to thifensulfuron methyl and other sulfonyl urea ALS inhibitor-type herbicides using a traditional breeding method is already available on the market under the product name STS Soybean. Similarly, SR Corn is one example of plants to which resistance to acetyl CoA carboxylase inhibitors, such as trione oxime, allyloxy fenoxy propionate and other herbicides, has been added using a traditional breeding method.

Also, plants to which resistance to acetyl CoA carboxylase inhibitors has been added are described in Proceedings of the National Academy of Sciences of the United States of America (Proc. Natl. Acad. Sci. USA), vol. 87, pp. 7175-7179 (1990), etc. Also, mutant acetyl CoA carboxylases resistant to acetyl CoA carboxylase inhibitors are reported in Weed Science, vol. 53, pp. 728-746 (2005), etc. By introducing these mutant acetyl CoA carboxylase genes to plants via genetic modification engineering, or by introducing the mutation relating to the adding of resistance to plant acetyl CoA carboxylases, plants resistant to acetyl CoA carboxylase inhibitors can be created; furthermore, by introducing a site-specific amino acid substitution mutation to plant acetyl CoA carboxylase genes, ALS genes, etc., which is done by introducing into plant cells a nucleic acid to which a base substitution mutation has been introduced using chimeraplasty (Gura T. 1999. Repairing the Genome's Spelling Mistakes. Science 285: 316-318), plants resistant to acetyl CoA carboxylase inhibitors, ALS inhibitors, etc., can be created, and the agricultural/horticultural insecticide proposed by the present invention can also be used on these plants.

Furthermore, toxins that manifest in genetically modified plants include, for example, insecticidal proteins derived from *Bacillus cereus* and *Bacillus popilliae*; Cry1Ab, Cry1Ac, Cry1F, Cry1Fa2, Cry2Ab, Cry3A, Cry3Bb1, Cry9C and other δ-endotoxins, VIP1, VIP2, VIP3, VIP3A and other insecticidal proteins derived from *Bacillus thuringiensis*; insecticidal proteins derived from nematodes; scorpion toxin, spider toxin, bee toxin, insect-specific nerve toxin and other toxins produced in animals; filiform toxins; plant lectin; agglutinins; trypsin inhibitors, serin protease inhibitors, patatin, cystatin, papain inhibitors and other protease inhibitors; ricin, corn-RIP, abrin, luffin, saporin, bryodine and other ribosome inactivating proteins (RIP); 3-hydroxy steroid oxidase, ecdysteroid-UDP-glucosyl transferase, cholesterol oxidase and other steroid metabolic enzyme; ecdysone inhibitors; HMG-CoA reductase; sodium channel and calcium channel inhibitors and other ion channel inhibitors; young hormone esterase; diuretic hormone receptors; stilbene synthase; bi-benzyl synthase; chitinase; glucanase, etc.

Also, toxins that manifest in these genetically modified plants include hybrid toxins based on Cry1Ab, Cry1Ac, Cry1F, Cry1Fa2, Cry2Ab, Cry3A, Cry3Bb1, Cry9C, Cry34Ab, Cry35Ab and other δ-endotoxin proteins, VIP1, VIP2, VIP3, VIP3A and other insecticidal proteins, as well as partially defective toxins and modified toxins. Hybrid toxins are created by modification engineering, based on new combinations of different domains of these proteins. Among partially defective toxins, Cry1Ab whose amino acid sequence is partially defective is known. Modified toxins are natural toxins whose amino acid or acids is/are substituted.

Examples of these toxins, and modified plants capable of synthesizing these toxins, are described in EP-A-0 374 753, WO 93/07278, WO 95/34656, EP-A-0 427 529, EP-A-451 878, WO 03/052073, etc.

Toxins contained in these modified plants add resistance to plants, especially resistance to coleoptera pest insects, hemiptera pest insects, diptera pest insects, lepidoptera pest insects and nematodes. The agricultural/horticultural insecticide proposed by the present invention may be combined or systematized with such technology.

The agricultural/horticultural insecticide proposed by the present invention may be used directly, or in a state diluted or suspended in water, etc., as appropriate, on plants where pest insects and nematodes are expected to generate, by an amount effective in controlling such pest insects and nematodes; to control pest insects and nematodes generating on fruit trees, grains, vegetables, etc., for example, it may be sprayed over stems and leaves, made into a solution agent in which seeds are soaked, prepared as powder to coat or otherwise treat seeds using Calper, etc., mixed into the entire layers of soil, applied in planting rows, mixed into bed soil, applied in cell seedlings, planting holes, around plant roots, in top dressing, rice boxes, on water surfaces, etc., or applied in soil, etc., to be absorbed through the roots. It may also be applied in nutrient solution in nutrient solution (hydroponic) cultivation, or used by means of smoking, tree trunk injection, etc.

Furthermore, the agricultural/horticultural insecticide proposed by the present invention may be used directly, or in a state diluted or suspended in water, etc., as appropriate, in locations where pest insects are expected to generate, by an amount effective in controlling such pest insects; for example, it may be sprayed over stored grain pest insects, house pest insects, hygiene pest insects, forest pest insects, etc., and may also be applied to residential construction materials, smoked, used as bait, etc.

Methods for treating seeds include, for example, a method to soak the seeds in the product in liquid form or in a liquid prepared from the product in solid form, with or without dilution, and let the reagent permeate in the seeds; a method to mix and powder-coat the product in solid form or liquid form with/on the seeds to cause the reagent to attach to the surface of the seeds; a method to mix the reagent with resin, polymer, or other adhesive carrier and then coat the mixture on the seeds; and a method to spray a reagent near the seeds when they are planted.

"Seeds" treated by these methods refer to initial forms of plants to be cultivated for propagation of plants, where examples, other than seeds, include bulbs, tubers, seed potatoes, stock sprouts, propagule, scaly bulbs, and plant forms used for vegetative propagation for the purpose of grafting.

When applying a method of use of the present invention, "soil" or "cultivation carrier" refers to a support on which to cultivate a crop, or specifically a support in which to grow roots, and its material, which is not limited in any way so long a plant can grow in it, may be a so-called soil, nursery mat, water, etc., or specifically it may be sand, pumice, vermiculite, diatomaceous earth, agar, gel-like substance, polymeric substance, rock wool, glass wool, wood chips, bark, etc.

Methods for spraying over stems and leaves of crops or over stored grain pest insects, house pest insects, hygiene pest insects, forest pest insects, etc., include a method to spray the product in emulsion form, flowable form, or other liquid form, or in wettable powder form, water-dispersible granular form, or other solid form that has been diluted in water as deemed appropriate; a method to spray the product in powder form; smoking, or the like Methods for application to soil include, for example, a method to apply the product in liquid form with or without dilution in water, to roots of plant forms, nursery beds, etc.; a method to spray the product in granular form over roots of plant forms, nursery beds, etc.; a method to spray the product in powder form, wettable powder form, water-dispersible granular form, granular form, etc., before seeding or transplanting, and mix it with the entire soil; and a method to spray the product in powder form, wettable powder form, water-dispersible granular form, granular form, etc., to planting holes, planting rows, etc., before seeding or before planting of plant forms, etc.

Concerning methods for application to rice nursery beds, the product may be in different forms depending on the timing of application, such as the seeding stage, vegetation stage, transplantation stage, etc., where it may be applied in such forms as powder, water-dispersible granules, granules, etc. The product may also be mixed with cultivation soil, in the form of mixing of cultivation soil with powder, water-dispersible granules, granules, etc., such as mixing with bed soil, mixing with cover soil, mixing with the entire cultivation soil, etc. Cultivation soil may be simply layered with various forms of the product.

On methods for application to rice paddies, the product in jumbo pack form, pack form, granular form, water-dispersible granular form or other solid form, or in flowable form, emulsion form, or other liquid form, is normally sprayed over rice paddies that are flooded with water. In addition, when planting rice seedlings the product in an appropriate form may be directly, or mixed with fertilizer first, sprayed over or injected into soil. Also, the reagent in emulsion form, flowable form, etc., may be used at water gates, irrigation systems or other sources of water, etc., that flows into rice paddies, so that it is applied with the supply of water and labor can be saved.

With field crops, cultivation carriers, etc., in close proximity of seeds and plant forms can be treated in the seeding stage through nursery stage. With plants whose seeds are directly sown on fields, ideally the product is directly applied to seeds or to plant roots during cultivation. The product may be sprayed in granular form, or the product in liquid form with or without dilution in water may be applied through irrigation, etc. It is also desirable to mix the product in granular form with a cultivation carrier before seeding, and then perform seeding.

For treatment in the seeding and nursery periods of plants to be cultivated for transplantation, desirably the seeds are treated directly or the product in liquid form is applied through irrigation to, or the product in granular form is sprayed over, nursery beds. It is also desirable to apply the product in granular form to planting holes at the time of final planting, or mix it with the cultivation carrier near the transplanting destination.

The agricultural/horticultural insecticide proposed by the present invention is generally formed into shapes convenient for use, according to normal methods of formulation of agricultural chemicals.

To be specific, an oxazepine compound or salt thereof expressed by General Formula (I) according to the present invention may be blended into an appropriate inert carrier, by an appropriate ratio, together with an auxiliary agent(s), if necessary, and dissolved, separated, suspended, mixed, impregnated, adsorbed or attached, and formulated into an appropriate form such as a suspension, emulsion, liquid, wettable powder, water-dispersible granules, granules, powder, tablets, pack, etc., for use.

The composition proposed by the present invention (agricultural/horticultural insecticide or zoobiotic parasite control agent) may contain, in addition to its active ingredient, those additive ingredients normally used in agricultural/horticultural insecticides or zoobiotic parasite control agents. These additive ingredients include solid carriers, liquid carriers and other carriers, surface-active agents, dispersants, wetting agents, binders, tackifiers, thickening agents, coloring agents, extenders, spreading agents, anti-freeze agents, anti-caking agents, disintegrating agents, stabilizing agents, etc. In addition to the above, preservatives, plant pieces, etc., may also be used as additive ingredients, if necessary. Any of these additive ingredients may be used alone or two or more types may be combined.

Solid carries include, for example, quartz, clay, kaolinite, pyrophyllite, sericite, talc, bentonite, acid clay, attapulgite, zeolite, diatomaceous earth and other natural minerals, calcium carbonate, ammonium sulfate, sodium sulfate, potassium chloride and other inorganic salts, synthetic silicic acid, synthetic silicate, starch, cellulose, plant powders (such as sawdust, coconut shell, corn cob, tobacco stem, etc.) and other organic solid carriers, polyethylene, polypropylene, polyvinylidene chloride and other plastic carriers, urea, inorganic hollows, plastic hollows, fumed silica (white carbon), etc. Any of these may be used alone or two or more types may be combined.

Liquid carries include, for example, methanol, ethanol, propanol, isopropanol, butanol and other monohydric alcohols, ethylene glycol, diethylene glycol, propylene glycol, hexylene glycol, polyethylene glycol, polypropylene glycol, glycerin, and other polyhydric alcohols, propylene glycol ether and other polyhydric alcohol compounds, acetone, methyl ethyl ketone, methyl isobutyl ketone, diisobutyl ketone, cyclohexanone and other ketones, ethyl ether, dioxane, ethylene glycol monoethyl ether, dipropyl ether, THF, and other ethers, normal paraffin, naphthene, isoparaffin, kerosene, mineral oil and other fatty acid hydrocarbons, benzene, toluene, xylene, solvent naphtha, alkyl naphthalene and other aromatic hydrocarbons, dichloromethane, chloroform, carbon tetrachloride and other halogenated hydrocarbons, ethyl acetate, diisopropyl phthalate, dibutyl phthalate, dioctyl phthalate, dimethyl adipate and other esters, γ-butyrolactone and other lactones, dimethyl formamide, diethyl formamide, dimethyl acetamide, N-alkyl pyrolidinone and other amides, acetonitrile and other nitriles, dimethyl sulfoxide and other sulfur compounds, soybean oil, rape seed oil, cotton seed oil, castor oil and other vegetable oils, water, etc. Any of these may be used alone or two or more types may be combined.

Surface active agents used as dispersants and wetting agents include, for example, sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl allyl ether, polyoxyethylene alkyl phenyl ether, polyoxyethylene dialkyl phenyl ether, polyoxyethylene alkyl phenyl ether formalin condensation product, polyoxyethylene polyoxypropylene block copolymer, polystyrene polyoxyethylene block polymer, alkyl polyoxyethylene polypropylene block copolymer ether, polyoxyethylene alkyl amine, polyoxyethylene fatty acid amide, polyoxyethylene fatty acid bisphenyl ether, polyalkylene benzyl phenyl ether, polyoxyalkylene styryl phenyl ether, acetylene diol, polyoxy alkylene added acetylene diol, polyoxyethylene ether-type silicone, ester-type silicone, fluorine surface active agents, polyoxyethylene castor oil, polyoxyethylene hardened castor oil and other non-ionic surface active agents, alkyl sulfate, polyoxyethylene alkyl ether sulfate, polyoxyethylene alkyl phenyl ether sulfate, polyoxyethylene styryl phenyl ether sulfate, alkyl benzene sulfonate, alkyl allyl sulfonate, lignin sulfonate, alkyl sulfone succinate, naphthalene sulfonate, alkyl naphthalene sulfonate, salt of formalin condensation product of naphtyalene sulfonate, salt of formalin condensation product of alkyl naphthalene sulfonate, fatty acid salt, polycarbonate, polyacrylate, N-methyl-fatty acid sarcocinate, resin acid salt, polyoxyethylene alkyl ether phosphate, polyoxyethylene alkyl phenyl ether phosphate and other anionic surface active agents, lauryl amine hydrochloride, stearyl amine hydrochloride, oleyl amine hydrochloride, stearyl amine acetate, stearyl aminopropyl amine acetate, alkyl trimethyl ammonium chloride, alkyl dimethyl benzalkonium chloride and other alkyl amine salts and other cationic surface active agents, amino acid-type or betaine-type and other ampholytic surface active agents, etc. Any of these surface active agents may be used alone or two or more types may be combined.

Binders and tackifiers include, for example, carboxy methyl cellulose and salt thereof, dextrin, water-soluble starch, xanthan gum, guar gum, sucrose, polyvinyl pyrolidone, gum arabic, polyvinyl alcohol, polyvinyl acetate, sodium polyacrylate, polyethylene glycol with an average molecular weight of 6000 to 20000, polyethylene oxide with an average molecular weight of 100000 to 5000000, phospholipids (such as cephaline, lecithin, etc.), cellulose powder, processed starch, polyamino carboxylic chelate compound, cross-linked polyvinyl pyrolidone, maleate and styrene copolymer, (meth)acrylate copolymer, half ester of polyhydric alcohol-based polymer and dicarboxylic unhydride, water-soluble salt of polystyrene sulfonate, paraffin, terpene, polyamide resin, polyacrylate, polyoxyethylene, wax, polyvinyl alkyl ether, alkyl phenol formalin condensation product, synthetic resin emulsion, etc.

Thickening agents include, for example, xanthan gum, guar gum, diutan gum, carboxy methyl cellulose, polyvinyl pyrolidone, carboxy vinyl polymer, acrylic polymers, starch compounds, polysaccharides and other water-soluble polymers, highly pure bentonite, fumed silica (white carbon) and other inorganic fine powders, etc.

Coloring agents include, for example, iron oxide, titanium oxide, Prussian blue and other inorganic pigments, alizarin dyes, azo dyes, metal phthalocyanine dies and other organic dyes, etc.

Anti-freeze agents include, for example, ethylene glycol, diethylene glycol, propylene glycol, glycerin and other polyhydric alcohols, etc.

Auxiliary agents to prevent caking or promote disintegration include, for example, starch, alginic acid, mannose, galactose and other polysaccharides, polyvinyl pyrolidone, fumed silica (white carbon), ester gum, petroleum resin, sodium tripolyphosphate, sodium hexamethaphosphate, stearate metal salt, cellulose powder, dextrin, methacylate ester copolymer, polyvinyl pyrolidone, polyamino carboxylic chelate compound, sulfonated styrene-isobutylene-maleate anhydride copolymer, starch-polyacrylonitrile graft copolymer, etc.

Stabilizing agents include, for example, zeolite, raw lime, magnesium oxide and other drying agents, phenol compounds, amine compounds, sulfur compounds, phosphate compounds and other anti-oxidants, salicylate compounds, benzophenone compounds and other UV absorbents, etc.

Preservatives include, for example, potassium sorbate, 1,2-benzothiazoline-3-one, etc.

Furthermore, functional spreading agents, piperonyl butoxide and other metabolic breakdown inhibitors and other activity enhancing agents, propylene glycol and other anti-freeze agents, BHT and other anti-oxidants, UV absorbents and other auxiliary agents may also be used, as necessary.

The blending ratio of the active ingredient compound may be increased or decreased as necessary, to a level selected as deemed appropriate in a range of 0.01 to 90 parts by weight relative to 100 parts by weight of the agricultural/horticultural insecticide proposed by the present invention. In the case of powder, granules, emulsion, or wettable powder, for example, 0.01 to 50 parts by weight (0.01 to 50 percent by weight relative to the total weight of the agricultural/horticultural insecticide) is appropriate.

How much the agricultural/horticultural insecticide proposed by the present invention is used varies depending on various factors, such as purpose, pest insect to be controlled, condition of growth of the crop, trend of generation of the pest insect, weather, environmental conditions, form of the product, application method, application location, application timing, etc.; however, a desired amount of the active ingredient compound may be selected as deemed appropriate in a range of 0.001 g to 10 kg, or preferably 0.01 g to 1 kg, per 10 ares.

The agricultural/horticultural insecticide proposed by the present invention may be mixed with other agricultural/horticultural insecticides, miticides, nemacides, bactericides, biological agrochemicals, etc., for the purpose of expanding the scope of pest insects to be controlled and timings at which they can be controlled, or for reducing the amount of chemical, or it may be mixed with herbicides, plant growth controlling agents, fertilizers, etc., depending on the application location.

Examples of other agricultural/horticultural insecticides, miticides, and nemacides used for the aforementioned purposes include, among others, 3,5-xylyl methylcarbamate (XMC), *Bacillus thuringienses aizawai, Bacillus thuringienses israelensis, Bacillus thuringienses japonensis, Bacillus thuringienses kurstaki, Bacillus thuringienses tenebrionis, Bacillus thuringienses*-produced crystal protein toxins, BPMC,Bt toxin insecticidal compounds, CPCBS (chlorfenson), DCIP (dichlorodiisopropyl ether), D-D (1, 3-Dichloropropene), DDT, NAC, O-4-dimethylsulfamoylphenyl O, O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, Potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, dicofol, salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methyneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisol hydrochloride, fenbutatin oxide, morantel tartarate, methyl bromide, cyhexatin, calcium cyanamide, calcium polysulfide, sulfur, nicotine-sulfate, etc.

Examples of agricultural/horticultural bactericides used for similar purposes include, among others, aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid octhilinone, ofurace, orysastrobin, metam-sodium and other soil sterilizers, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, Dodecylbenzenesulphonic acid bisethylenediamine copper salt (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam sodium, metalaxyl, metalaxyl-M, metiram, methyl isothiocyanate, mepthyldinocap, metconazole, metsulfovax, methfuroxam, metominostrobin, metrafenone, mepanipyrim, mefenoxam, meptyldinocap, mepronil, mebenil iodomethane, rabenzazole, benzalkonium chloride, basic copper chloride, basic copper sulfate, silver and other inorganic bactericides, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, 8-hydroxy quinoline copper (oxine copper) and other copper compounds, zinc sulfate, copper sulfate pentahydrate, etc.

Similarly, examples of herbicides include, among others, 1-Naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, diallate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide, methyl bromide, etc.

Also, similar effects can be expected by mixing with biological agrochemicals, such as nuclear polyhedrosis virus (NPV), granulosis virus (GV), cytoplasmic polyhedrosis virus (CPV), entomopoxi virus (EPV) and other virus agents, *Monacrosporium phymatophagum*, *Steinernema carpocapsae*, *Steinernema kushidai*, *Pasteuria penetrans*, and other microbial agrochemicals used as insecticides or nemacides, *Trichoderma lignorum*, *Agrobacterium radiobactor*, *Apathogenic erwinia carotovora*, *Bacillus subtilis*, and other microbial agrochemicals used as bactericides, *Xanthomonas campestris* and other biological agrochemicals used as herbicides, and the like.

Furthermore, it is also possible to mix with such biological agrochemicals as Onshitsutsuyakobachi (*Encarsia formosa*), Koremanaburabachi (*Aphidius colemani*), Shokugatamabae (*Aphidoletes aphidimyza*), Isaeahimekobachi (*Diglyphus isaea*), Hamogurikomayubachi (*Dacnusa sibirica*), Chirikaburidani (*Phytoseiulus persimilis*), Kukumerisukaburidani (*Amblyseius cucumeris*), Namihimehanakamemushi (*Orius sauteri*), and other natural predators, *Beauveria brongniartii* and other microbial agrochemicals, (Z)-10-tetradecenyl=acetate, (E,Z)-4,10-tetradecadienyl=acetate, (Z)-8-dodecenyl=acetate, (Z)-11-tetradecenyl=acetate, (Z)-13-icosen-10-one, 14-methyl-1-octadecene, and other pheromone agents.

Representative examples of the present invention are shown below; it should be noted, however, that the present invention is not limited to these examples.

REFERENCE EXAMPLE 1

Manufacturing of Ethyl (E)-4-Chloro-3-Oxo-2-(2-(Pyridine-3-Yl) Hydrazono) Butanoate

[Chemical 24]

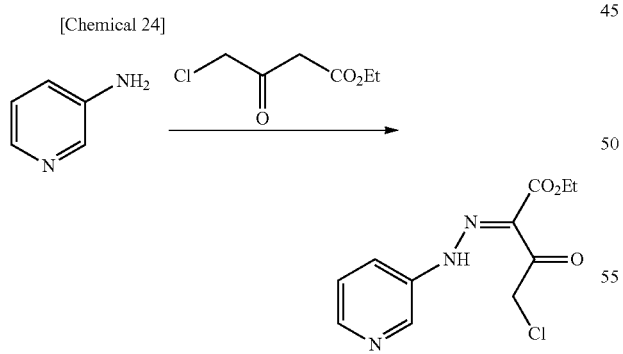

3-amino pyridine (7.52 g, 80.0 mmol) was added to 6N-hydrochloric acid (27 mL, 160 mmol). Into this solution, aqueous solution (40 mL) of sodium nitrite (5.52 g, 80.0 mmol) was dripped by keeping the temperature at 3° C. or below, to cause and maintain reaction for 20 minutes. Thereafter, ethyl 4-chloroaceto acetate (13.2 g, 80.0 mmol), ethyl acetate (30 mL), and sodium acetate (15.0 g, 183 mmol) were added, to cause and maintain reaction for 1 hour at 0° C. Ethyl acetate and water were added to the reaction solution and an organic layer was extracted with ethyl acetate, after which the organic layer was washed with saturated salt water, dried using anhydrous magnesium sulfate, and then vacuum concentrated. The residue was refined by silica gel column chromatography, to obtain ethyl (E)-4-chloro-3-oxo-2-(2-(pyridine-3-yl) hydrazono) butanoate (17.8 g, 66.0 mmol, 82%). 1H-NMR δ: 13.02 (1H, s), 8.67-8.63 (1H, m), 8.47-8.44 (1H, m), 7.75-7.69 (1H, m), 7.41-7.35 (1H, m), 4.69 (2H, m), 4.41 (2H, q), 1.42 (3H, t)

REFERENCE EXAMPLE 2

Manufacturing of Ethyl 4-Hydroxy-1-(Pyridine-3-Yl)-1H-Pyrazole-3-Carboxylate

[Chemical 25]

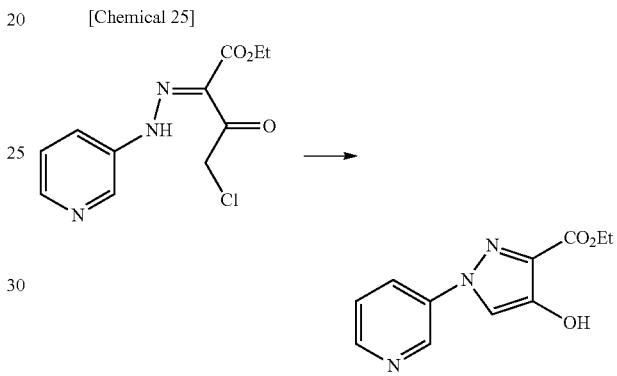

Tert-butoxy potassium (7.84 g, 70.0 mmol) was added to THF (70 mL) solution of ethyl (E) 4-chloro-3-oxo-2-(2-(pyridine-3-yl) hydrazono) butanoate (17.0 g, 63.0 mmol) at 0° C., to cause and maintain reaction for 1 hour at room temperature. Aqueous solution of saturated ammonium chloride was added to the reaction solution and an organic layer was extracted with ethyl acetate, after which the organic layer was washed with saturated salt water, dried using anhydrous magnesium sulfate, and then vacuum concentrated. The obtained crystal was washed with hexane/ethyl acetate and then filtered out, to obtain ethyl 4-hydroxy-1-(pyridine-3-yl)-1H-pyrazole-3-carboxylate (12.0 g, 51.4 mmol, 82%). Melting point: 135-137° C.

EXAMPLE 1

Manufacturing of Ethyl 4-(2-Nitrophenoxy)-1-(Pyridine-3-Yl)-1H-Pyrazole-3-Carboxylate

[Chemical 26]

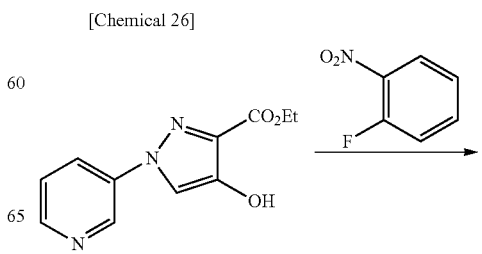

-continued

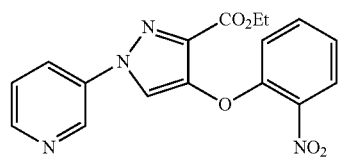

2-fluoronitrobenzene (1.48 g, 10.3 mmol) and potassium carbonate (1.55 g, 11.2 mmol) were added to acetonitrile (40 mL) solution of ethyl 4-hydroxy-1-(pyridine-3-yl)-1H-pyrazole-3-carboxylate (2.00 g, 8.58 mmol), to cause and maintain reaction for 1 hour under heating to reflux. The reaction solution was returned to room temperature, and then filtered out using Celite and the filtrate was vacuum concentrated. The obtained crystal was washed with hexane/MTBE and then filtered out, to obtain ethyl 4-(2-nitrophenoxy)-1-(pyridine-3-yl)-1H-pyrazole-3-carboxylate (2.81 g, 7.92 mmol, 92%). Melting point: 136-138° C.

EXAMPLE 2

Manufacturing of Ethyl 4-(2-Aminophenoxy)-1-(Pyridine-3-Yl)-1H-Pyrazole-3-Carboxylate

[Chemical 27]

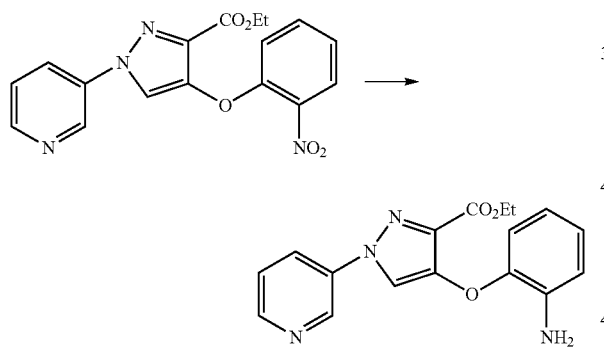

Ammonium chloride (0.21 g, 3.95 mmol) and electrolytic iron powder (1.32 g, 23.7 mmol) were added to ethanol/water (20 mL/10 mL) solution of ethyl 4-(2-nitrophenoxy)-1-(pyridine-3-yl)-1H-pyrazole-3-carboxylate (2.80 g, 7.90 mmol), to cause and maintain reaction for 1 hour under heating to reflux. The reaction solution was returned to room temperature, and then filtered out using Celite and the filtrate was vacuum concentrated. Ethyl acetate and water were added to this solution and an organic layer was extracted with ethyl acetate, after which the organic layer was washed with saturated salt water, dried using anhydrous magnesium sulfate, and then vacuum concentrated. The obtained crystal was washed with hexane/MTBE and then filtered out, to obtain ethyl 4-(2-aminophenoxy)-1-(pyridine-3-yl)-1H-pyrazole-3-carboxylate (1.88 g, 5.80 mmol, 73%). Melting point: 120-122° C.

EXAMPLE 3

Manufacturing of 2-(Pyridine-3-Yl)-2H-Benzo [B]Pyrazolo [3,4-F][1,4]Oxazepine-10(9H)-One (Compound No. 1-1)

[Chemical 28]

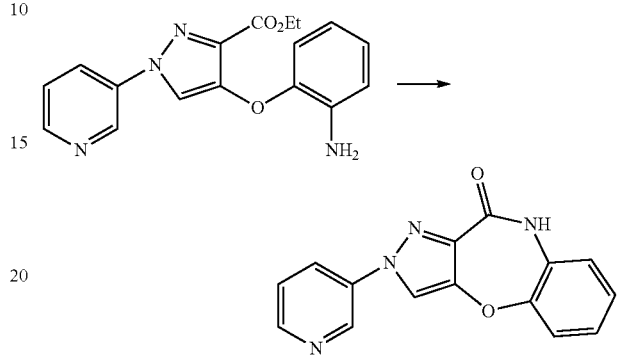

Tert-butoxy potassium (1.44 g, 12.8 mmol) was added to THF (40 mL) solution of ethyl 4-(2-aminophenoxy)-1-(pyridine-3-yl)-1H-pyrazole-3-carboxylate (1.88 g, 5.80 mmol) at 0° C., to cause and maintain reaction for 1 hour at room temperature. Aqueous solution of saturated ammonium chloride was added to the reaction solution and an organic layer was extracted with ethyl acetate, after which the organic layer was washed with saturated salt water, dried using anhydrous magnesium sulfate, and then vacuum concentrated. The obtained crystal was washed with hexane/MTBE and then filtered out, to obtain 2-(pyridine-3-yl)-2H-benzo [b]pyrazolo [3,4-f][1,4]oxazepine-10 (9H)-one (1.39 g, 4.99 mmol, 86%). Melting point: 259-262° C.

EXAMPLE 4

Manufacturing of 9-Methyl-2-(Pyridine-3-Yl)-2H-Benzo [B]Pyrazolo [3,4-F][1,4]Oxazepine-10 (9H)-One (Compound No. 1-2)

[Chemical 29]

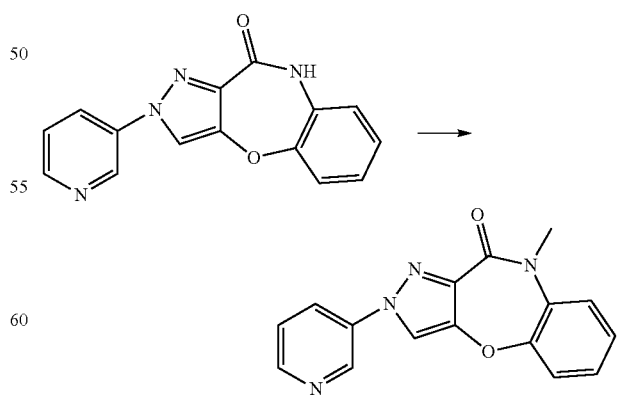

Sodium hydride (60%, 0.036 g, 0.91 mmol) was added to DMF (8 mL) solution of 2-(pyridine-3-yl)-2H-benzo [b]pyrazolo [3,4-f][1,4]oxazepine-10 (9H)-one (0.18 g, 0.65 mmol) at 0° C., to cause and maintain reaction for 10 minutes. Methyl iodide (0.13 g, 0.91 mmol) was added, to cause and maintain reaction for 1 hour at room temperature. Aqueous solution of saturated ammonium chloride was added to the reaction solution and an organic layer was extracted with ethyl acetate, after which the organic layer was washed with saturated salt water, dried using anhydrous magnesium sulfate, and then vacuum concentrated. The residue was refined by silica gel column chromatography, and the obtained crystal was washed with hexane/MTBE and then filtered out, to obtain 9-methyl-2-(pyridine-3-yl)-2H-benzo [b]pyrazolo [3,4-f][1,4]oxazepine-10 (9H)-one (0.13 g, 0.46 mmol, 71%). Melting point: 195-196° C.

EXAMPLE 5

Manufacturing of 4-Hydroxy-N-Methyl-1-(Pyridine-3-Y1)-1H-Pyrazole-3-Carboxamide

[Chemical 30]

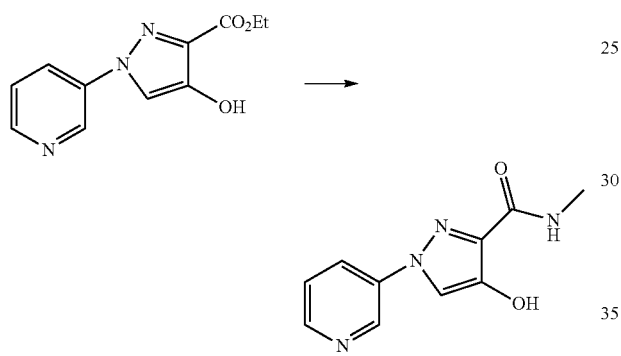

Methyl amine 40% methanol (10 mL) solution was added to methanol (10 mL) solution of ethyl 4-hydroxy-1-(pyridine-3-yl)-1H-pyrazole-3-carboxylate (1.00 g, 4.29 mmol), to cause and maintain reaction for 8 hours. The reaction solution was vacuum concentrated, and the obtained crystal was washed with hexane/acetone and then filtered out, to obtain 4-hydroxy-N-methyl-1-(pyridine-3-yl)-1H-pyrazole-3-carboxamide (0.94 g, 4.29 mmol, 100%). Melting point: 200-201° C.

EXAMPLE 6

Manufacturing of 6-Fluoro-9-Methyl-2-(Pyridine-3-Y1)-2H-Benzo [B]Pyrazolo [3,4-F][1,4]Oxazepine-10 (9H)-One (Compound No. 1-11)

[Chemical 31]

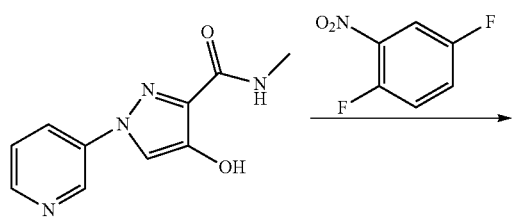

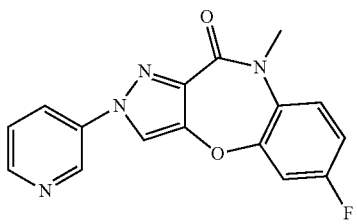

Potassium carbonate (0.21 g, 1.52 mmol) and 2,5-difluoronitrobenzene (0.15 g, 0.96 mmol) were added to acetonitrile (20 mL) solution of 4-hydroxy-N-methyl-1-(pyridine-3-yl)-1H-pyrazole-3-carboxamide (0.15 g, 0.69 mmol), to cause and maintain reaction for 7 hours under heating to reflux. The reaction solution was returned to room temperature, after which the deposited solids were dissolved with THF/methanol, and then filtered out using Celite and the filtrate was vacuum concentrated. The residue was refined by silica gel column chromatography, to obtain 6-fluoro-9-methyl-2-(pyridine-3-yl)-2H-benzo [b]pyrazolo [3,4-f][1,4]oxazepine-10 (9H)-one (0.14 g, 0.44 mmol, 64%). Melting point: 225-226° C.

EXAMPLE 7

Manufacturing of Ethyl 4-(4-Fluoro-2-Nitrophenoxy)-1-(Pyridine-3-Y1)-1H-Pyrazole-3-Carboxylate

[Chemical 32]

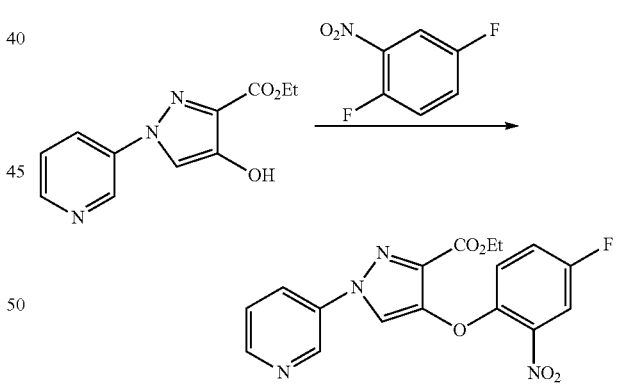

2,5-difluoronitrobenzene (2.70 g, 17.0 mmol) and potassium carbonate (2.35 g, 17.0 mmol) were added to acetonitrile (100 mL) solution of ethyl 4-hydroxy-1-(pyridine-3-yl)-1H-pyrazole-3-carboxylate (3.05 g, 13.1 mmol), to cause and maintain reaction for 2 hours under heating to reflux. The reaction solution was returned to room temperature, and then filtered out using Celite and the filtrate was vacuum concentrated. The obtained crystal was washed with hexane/MTBE and then filtered out, to obtain ethyl 4-(4-fluoro-2-nitrophenoxy)-1-(pyridine-3-yl)-1H-pyrazole-3-carboxylate (4.78 g, 12.8 mmol, 98%). Melting point: 133-135° C.

EXAMPLE 8

Manufacturing of 4-(4-Fluoro-2-Nitrophenoxy)-1-(Pyridine-3-Yl)-1H-Pyrazole-3-Carboxylate

[Chemical 33]

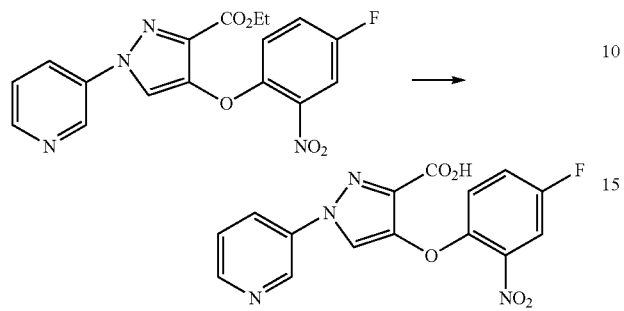

Lithium hydroxide monohydrate (1.07 g, 25.6 mmol) was added to methanol/water (50 mL/10 mL) solution of ethyl 4-(4-fluoro-2-nitrophenoxy)-1-(pyridine-3-yl)-1H-pyrazole-3-carboxylate (4.77 g, 12.8 mmol), to cause and maintain reaction for 16 hours. 6N-hydrochloric acid was added to the reaction solution to make it mildly acid, after which the reaction solution was vacuum concentrated. The obtained crystal was washed with water, filtered out, and dried using a specimen dryer, to obtain 4-(4-fluoro-2-nitrophenoxy)-1-(pyridine-3-yl)-1H-pyrazole-3-carboxylate. This was used directly for the reaction in Example 9. 1H-NMR (d6-DMSO) δ: 9.15-9.12 (1H, m), 8.94 (1H, s), 8.66-8.62 (1H, m), 8.32-8.26 (1H, m), 8.05 (1H, dd), 7.66-7.60 (1H, m), 7.56 (1H, ddd), 7.34 (1H, dd)

EXAMPLE 9

Manufacturing of N-(Cyanomethyl)-4-(4-Fluoro-2-Nitrophenoxy)-1-(Pyridine-3-Yl)-1H-Pyrazole-3-Carboxamide

[Chemical 34]

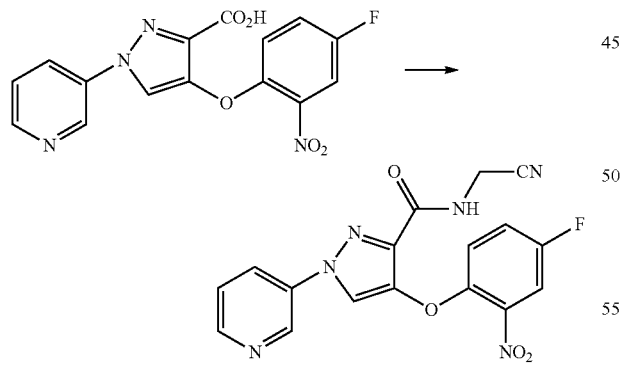

Triethyl amine (5.38 g, 53.2 mmol), amino acetonitrile hydrochloride (1.80 g, 19.5 mmol) and 2-chloro-1-methyl-pyridinium iodide (5.08 g, 19.5 mmol) were added to THF/DMF (40 mL/40 mL) solution of the 4-(4-fluoro-2-nitrophenoxy)-1-(pyridine-3-yl)-1H-pyrazole-3-carboxylate obtained in Example 8, to cause and maintain reaction for 18 hours. Water was added to the reaction solution and an organic layer was extracted with ethyl acetate, after which the organic layer was washed with saturated salt water, dried using anhydrous magnesium sulfate, and then vacuum concentrated. The residue was coarsely refined by silica gel column chromatography, to obtain N-(cyanomethyl)-4-(4-fluoro-2-nitrophenoxy)-1-(pyridine-3-yl)-1H-pyrazole-3-carboxamide. This was used directly for the reaction in Example 10. 1H-NMR δ: 8.99-8.95 (1H, m), 8.70-8.65 (1H, m), 8.08-8.03 (1H, m), 7.94 (1H, s), 7.76 (1H, dd), 7.51-7.46 (1H, m), 7.33-7.23 (2H, m), 7.19 (1H, dd), 4.36 (2H, d)

EXAMPLE 10

Manufacturing of 2-(6-Fluoro-10-Oxo-2-(Pyridine-3-Yl)-2H-Benzo [B]Pyrazolo [3,4-F][1,4]Oxazepine-9 (10H)-Yl) Acetonitrile (Compound No. 1-13)

[Chemical 35]

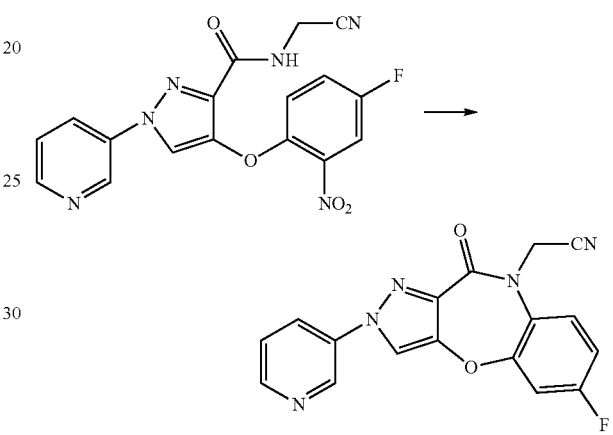

Potassium carbonate (5.06 g, 36.6 mmol) was added to acetonitrile (100 mL) solution of the N-(cyanomethyl)-4-(4-fluoro-2-nitrophenoxy)-1-(pyridine-3-yl)-1H-pyrazole-3-carboxamide obtained in Example 9, to cause and maintain reaction for 2 hours under heating to reflux. The reaction solution was returned to room temperature, after which the deposited solids were dissolved with THF, and then filtered out using Celite and the filtrate was vacuum concentrated. The obtained crystal was washed with hexane/MTBE and then filtered out, to obtain 2-(6-fluoro-10-oxo-2-(pyridine-3-yl)-2H-benzo [b]pyrazolo [3,4-f][1,4]oxazepine-9 (10H)-yl) acetonitrile (3.67 g, 10.9 mmol, 85% (3 steps)). Melting point: 212-214° C.

EXAMPLE 11

Manufacturing of 9-Methyl-2-(Pyridine-3-Yl)-2H-Benzo [B]Pyrazolo[3,4-F][1,4]Oxazepine-10 (9H)-Thione (Compound No. 2-2)

[Chemical 36]

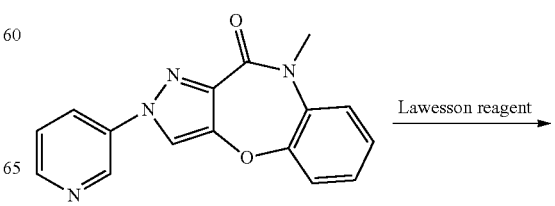

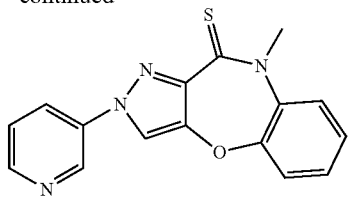

Lawesson's reagent (0.15 g, 0.37 mmol) was added to toluene (10 mL) solution of 9-methyl-2-(pyridine-3-yl)-2H-benzo [b]pyrazolo [3,4-f][1,4]oxazepine-10 (9H)-one (0.091 g, 0.31 mmol), and the mixture was agitated for 4 hours under heating to reflux. The reaction solution was returned to room temperature, and then filtered out using Celite and the filtrate was vacuum concentrated. The residue was refined by silica gel column chromatography, to obtain 9-methyl-2-(pyridine-3-yl)-2H-benzo [b]pyrazolo [3,4-f][1,4]oxazepine-10 (9H)-thione (0.064 g, 0.21 mmol, 66%). Melting point: 206-210° C.

EXAMPLE 12

Manufacturing of 7-Fluoro-2-(Pyridine-3-Yl)-9,10-Dihydro-2H-Benzo [B]Pyrazolo [3,4-F][1,4]Oxazepine (Compound No. 3-6)

[Chemical 37]

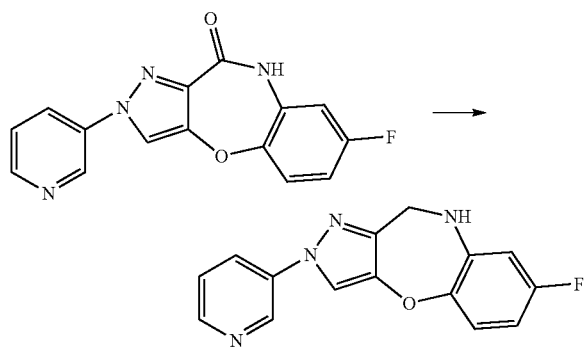

LiALH$_4$ (0.046 g, 1.01 mmol) was added to THF (10 mL) solution of 7-fluoro-2-(pyridine-3-yl)-2H-benzo [b]pyrazolo [3,4-f][1,4]oxazepine-10 (9H)-one (0.15 g, 0.51 mmol) at 0° C., and the mixture was agitated for 20 hours at room temperature. The reaction solution was cooled to 0° C., after which water (0.1 mL), 15% NaOH aqueous solution (0.1 mL) and water (0.1 mL) were added one by one, and the mixture was agitated for 1.5 hours at room temperature. The resulting solution was filtered out using Celite, and the filtrate was vacuum concentrated. The residue was refined by silica gel column chromatography, to obtain 7-fluoro-2-(pyridine-3-yl)-9,10-dihydro-2H-benzo [b]pyrazolo [3,4-f][1,4]oxazepine (0.072 g, 0.25 mmol, 50%). Melting point: 186-188° C.

Similarly Compound Nos. 14-1 to 14-5 and 15-1 to 15-8 were manufactured according to the conditions described in Examples 1 to 4.

Examples of products are shown below; it should be noted, however, that products are not limited to these examples. In Product Examples, "parts" refers to "parts by weight."

PRODUCT EXAMPLE 1

| | |
|---|---|
| Compound according to the present invention | 10 parts |
| Xylene | 70 parts |
| N-methyl pyrolidone | 10 parts |
| Mixture of polyoxyethylene nonyl phenyl ether and calcium alkyl benzene sulfonate | 10 parts |

The above ingredients were homogeneously mixed and dissolved, and made into an emulsion.

PRODUCT EXAMPLE 2

| | |
|---|---|
| Compound according to the present invention | 3 parts |
| Clay powder | 82 parts |
| Diatomaceous earth powder | 15 parts |

The above ingredients were homogeneously mixed and crushed, and made into a powder.

PRODUCT EXAMPLE 3

| | |
|---|---|
| Compound according to the present invention | 5 parts |
| Mixed powder of bentonite and clay | 90 parts |
| Calcium lignin sulfonate | 5 parts |

The above ingredients were homogeneously mixed and kneaded, with an appropriate amount of water being added to it, after which the kneaded mixture was granulated and dried, and made into granules.

PRODUCT EXAMPLE 4

| | |
|---|---|
| Compound according to the present invention | 20 parts |
| Kaolin and synthetic high-dispersion silicic acid | 75 parts |
| Mixture of polyoxyethylene nonyl phenyl ether and calcium alkyl benzene sulfonate | 5 parts |

The above ingredients were homogeneously mixed and crushed, and made into a wettable powder.

TEST EXAMPLE 1

Test of Preventive Value Against Green Peach Aphid (*Myzus Persicae*)

Chinese cabbages were planted in plastic pots, each with a size of 8 cm in diameter and 8 cm in height, after which green peach aphids were propagated and the number of parasitic insects was examined in each pot. An oxazepine compound or salt thereof expressed by General Formula (I) according to the present invention was dispersed in water and the dispersion was diluted to 500 ppm in the form of a reagent, after which the reagent was sprayed over stems and leaves of potted Chinese cabbages and let dry under wind, and the pots were kept in a greenhouse, and on the sixth day after the reagent was sprayed, the number of green peach aphids living parasitically on each Chinese cabbage was examined and the preventive value was calculated based on the formula below, and judgment was made according to the criteria below.

Preventive value=100−{(T×Ca)/(Ta×C)}×100 [Mathematical Formula 1]

Ta: Number of parasitic insects inside the treatment area before spraying
T: Number of parasitic insects inside the treatment area after spraying
Ca: Number of parasitic insects inside the non-treatment area before spraying
C: Number of parasitic insects inside the non-treatment area after spraying Judgment Criteria
A - - - Preventive value: 100%
B - - - Preventive value: 99%~90%
C - - - Preventive value: 89%~80%
D - - - Preventive value: 79%~50%

TEST EXAMPLE 2

Test of Insecticidal Efficacy Against Small Brown Planthopper (*Laodelphax Striatellus*)

An oxazepine compound or salt thereof expressed by General Formula (I) according to the present invention was dispersed in water and the dispersion was diluted to 500 ppm in the form of a reagent, after which rice plants raised from seeds (variety: Nipponbare) were soaked in the reagent for 30 seconds and dried under wind, and then placed in glass test tubes, each of which was inoculated with 10 third-instar larvae of small brown planthoppers and sealed with cotton, and eight days after the inoculation, the number of live insects and that of dead insects were examined and the corrected insect mortality was calculated based on the formula below, and judgment was made according to the criteria below.

Corrected insect mortality (%)=(Survival rate in non-treatment area−Survival rate in treatment area)/(Survival rate in non-treatment area)×100 [Mathematical Formula 2]

Judgment Criteria - - - Same as in Test Example 1.
The results show that, in Test Example 1, Compound Nos. 1-1, 1-2, 1-3, 1-4, 1-5, 1-6, 1-7, 1-8, 1-9, 1-11, 1-12, 1-13, 1-14, 1-15, 1-16, 1-17, 1-19, 1-22, 1-23, 1-26, 1-27, 1-28, 1-29, 1-30, 1-32, 1-33, 1-34, 1-35, 1-36, 1-37, 1-38, 1-39, 1-40, 1-41, 1-42, 1-44, 1-45, 1-46, 1-47, 1-48, 1-50, 1-51, 1-52, 1-53, 1-55, 1-56, 1-57, 1-58, 1-62, 1-67, 1-68, 1-70, 1-71, 1-73, 1-74, 1-75, 1-76, 1-77, 1-79, 1-80, 1-81, 1-83, 1-85, 1-86, 2-1, 2-2, 2-5, 3-1, 3-2, 3-5, 3-6, 3-9, 4-10, 5-2, 6-2, 6-3, 6-5, 6-6, 6-7, 6-18, 7-1, 7-2, 8-2, 8-3, 8-4, 8-5, 8-6, 8-7, 8-8, 8-9, 8-10, 8-11, 8-12, 8-13, 8-14, 8-15, 8-16, 8-17, 8-18, 8-19, 8-20, 8-22, 8-24, 8-25, 8-26, 8-27, 8-28, 8-29, 8-30, 8-31, 8-32, 8-33, 8-34, 8-35, 8-36, 8-37, 8-38, 8-39, 8-40, 8-41, 8-42, 8-43, 8-44, 8-45, 8-46, 8-47, 8-48, 8-49, 8-50, 8-51, 8-52, 8-53, 8-54, 8-55, 8-56, 8-59, 8-60, 8-61, 8-62, 8-63, 8-65, 8-67, 8-68, 8-69, 8-70, 8-71, 8-72, 8-73, 8-74, 8-75, 8-77, 8-78, 8-79, 8-80, 8-83, 8-84, 8-85, 8-86, 8-87, 8-88, 8-89, 8-90, 8-91, 8-92, 8-93, 8-94, 8-95, 8-96, 8-97, 8-98, 8-99, 8-100, 8-101, 8-102, 8-109, 8-110, 8-112, 8-113, 8-114, 8-115, 8-118, 8-119, 8-120, 8-121, 8-122, 8-123, 8-124, 8-125, 8-126, 8-127, 8-130, 8-131, 8-132, 8-133, 8-134, 8-136, 8-137, 8-138, 8-140, 8-141, 8-142, 8-143, 8-145, 8-147, 8-148, 8-152, 8-153, 8-160, 8-161, 9-1, 9-3, 9-4, 9-5, 9-7, 10-1, 11-1, 11-2, 11-3, 11-4, 11-5, 11-6, 11-7, 11-8, 11-9, 11-10, 11-11, 11-12, 11-13, 11-14, 11-17, 11-18, 11-19, 12-1, 13-1, 14-2, 14-4, 14-5, 15-1, 15-2, 15-3, 15-4, 15-5, 15-6, 15-7, and 15-8 among the oxazepine compounds expressed by General Formula (I) according to the present invention had excellent insecticidal effects of judgments A to D against green peach aphids.

Additionally, in Test Example 2, Compound Nos. 1-1, 1-2, 1-3, 1-4, 1-5, 1-6, 1-7, 1-8, 1-9, 1-11, 1-12, 1-13, 1-14, 1-15, 1-16, 1-17, 1-19, 1-23, 1-26, 1-27, 1-28, 1-29, 1-30, 1-31, 1-32, 1-33, 1-34, 1-35, 1-36, 1-37, 1-38, 1-39, 1-40, 1-41, 1-42, 1-44, 1-45, 1-46, 1-47, 1-48, 1-50, 1-51, 1-52, 1-53, 1-55, 1-56, 1-57, 1-58, 1-62, 1-67, 1-68, 1-69, 1-70, 1-71, 1-73, 1-74, 1-75, 1-76, 1-77, 1-79, 1-80, 1-81, 1-84, 1-85, 1-86, 2-1, 2-2, 2-5, 3-1, 3-3, 3-6, 4-10, 5-2, 6-2, 6-3, 6-6, 6-7, 7-1, 7-2, 8-2, 8-4, 8-10, 8-12, 8-13, 8-20, 8-21, 8-23, 8-24, 8-25, 8-26, 8-31, 8-32, 8-34, 8-35, 8-37, 8-38, 8-40, 8-41, 8-42, 8-45, 8-46, 8-49, 8-54, 8-56, 8-57, 8-58, 8-62, 8-64, 8-66, 8-68, 8-71, 8-73, 8-77, 8-93, 8-94, 8-95, 8-96, 8-102, 8-106, 8-110, 8-112, 8-114, 8-115, 8-117, 8-121, 8-124, 8-125, 8-128, 8-129, 8-130, 8-131, 8-135, 8-137, 8-140, 8-141, 8-143, 8-145, 8-150, 8-154, 8-158, 8-159, 9-1, 9-3, 11-1, 11-2, 11-5, 11-6, 11-7, 11-9, 11-10, 11-11, 11-15, 11-16, 11-17, 11-18, 11-19, 12-1, 13-1, 14-3, 14-5, 15-6, 15-7, and 15-8 among the oxazepine compounds expressed by General Formula (I) according to the present invention had insecticidal effects of judgments A to D against small brown planthoppers.

INDUSTRIAL FIELD OF APPLICATION

The oxazepine compound or salt thereof as proposed by the present invention has excellent effects as an agricultural/horticultural insecticide.

What is claimed is:
1. A compound of formula (I) or a salt thereof

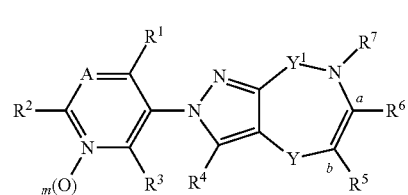

(I)

in the formula, $R^1$, $R^2$, $R^3$ and $R^4$ may be identical or different, representing:
(a1) a hydrogen atom;
(a2) a halogen atom;
(a3) a $(C_1-C_8)$ alkyl group;
(a4) a $(C_3-C_8)$ cycloalkyl group;
(a5) a $(C_1-C_8)$ alkoxy group;
(a6) a halo $(C_1-C_8)$ alkyl group;
(a7) a $(C_1-C_8)$ alkyl thio group;
(a8) a $(C_1-C_8)$ alkyl sulfinyl group;
(a9) a $(C_1-C_8)$ alkyl sulfonyl group;
(a10) a phenyl sulfonyl group;
(a11) an amino group; or
(a12) a $(C_1-C_8)$ alkyl carbonyl amino group;
$R^5$ and $R^6$ which form Structural Formula $Q^1$, $Q^2$, $Q^3$, $Q^4$, $Q^5$, $Q^6$, $Q^7$ or $Q^8$ below together with carbon atoms to which the substitution groups are bonded:

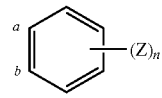

Q1

-continued

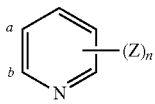
Q2

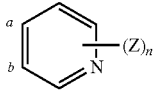
Q3

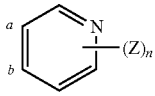
Q4

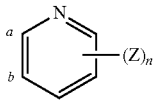
Q5

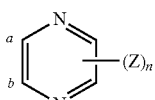
Q6

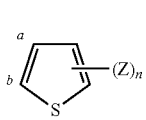
Q7

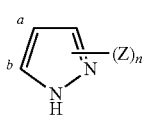
Q8

(in the formula, Z may be identical or different, representing (a) a halogen atom, (b) a cyano group, (c) a nitro group, (d) an amino group, (e) a di ($C_1$-$C_6$) alkyl amino group (($C_1$-$C_6$) alkyl may be identical or different), (f) a ($C_1$-$C_6$) alkyl group, (g) a ($C_1$-$C_6$) alkoxy group, (h) a halo ($C_1$-$C_6$) alkyl group, (i) a halo ($C_1$-$C_6$) alkoxy group, (p) a hydroxyl group, (q) a nitro group, (r) a ($C_1$-$C_6$) alkoxy ($C_1$-$C_6$) alkyl group, (s) a di ($C_1$-$C_6$) alkoxy ($C_1$-$C_6$) alkyl group (alkyl in di ($C_1$-$C_6$) alkoxy may be identical or different, and may be bonded to an identical or different carbon atom), (t) a phenyl group, (u) a mono ($C_1$-$C_6$) alkyl amino group, (v) a mono formyl amino group, (w) a mono ($C_1$-$C_6$) alkyl carbonyl amino group, (x) a mono ($C_1$-$C_6$) alkyl sulfonyl amino group, (y) a bis ($C_1$-$C_6$) alkyl sulfonyl amino group (alkyl in bis ($C_1$-$C_6$) alkyl may be identical or different), (z) a ($C_1$-$C_6$) alkoxy carbonyl group, (aa) a hydroxy carbonyl group, (ab) a ($C_1$-$C_6$) alkyl sulfonyl amino carbonyl group, (ac) a ($C_1$-$C_6$) alkyl sulfonyl group, (ad) a halo ($C_1$-$C_6$) alkyl sulfonyl group, or (ae) an amino sulfonyl group, and n represents an integer of 0 to 2; and a and b each represent a bonding position);

$R^7$ represents:
(c1) a hydrogen atom;
(c2) a ($C_1$-$C_{12}$) alkyl group;
(c3) a ($C_2$-$C_8$) alkenyl group;
(c4) a ($C_2$-$C_8$) alkynyl group;
(c5) a cyano ($C_1$-$C_8$) alkyl group;
(c6) a ($C_3$-$C_8$) cycloalkyl group;
(c7) a halo ($C_1$-$C_8$) alkyl group;
(c8) a halo ($C_2$-$C_8$) alkenyl group;
(c9) a halo ($C_2$-$C_8$) alkynyl group;
(c10) a ($C_1$-$C_8$) alkoxy ($C_1$-$C_8$) alkyl group;
(c11) a ($C_1$-$C_8$) alkyl thio ($C_1$-$C_8$) alkyl group;
(c12) a ($C_1$-$C_8$) alkyl sulfinyl ($C_1$-$C_8$) alkyl group;
(c13) a ($C_1$-$C_8$) alkyl sulfonyl ($C_1$-$C_8$) alkyl group;
(c14) a ($C_1$-$C_8$) alkyl carbonyl group;
(c15) a ($C_1$-$C_8$) alkoxy carbonyl group;
(c16) a ($C_1$-$C_8$) alkoxy carbonyl ($C_1$-$C_8$) alkyl group;
(c17) an amino ($C_1$-$C_8$) alkyl group;
(c18) a di (($C_1$-$C_8$) alkyl) amino ($C_1$-$C_8$) alkyl group (in the formula, alkyl in di ($C_1$-$C_8$) alkyl may be identical or different);
(c19) a non-aromatic heterocyclic ($C_1$-$C_8$) alkyl group selected from the group consisting of pyrrolidinyl, piperidinyl, morpholinyl, thiomorpholinyl, piperadinyl, 4-methyl piperadinyl, oxazolidinyl, thiazolidinyl, imidazolidinyl, oxazolinyl, thiazolinyl, isoxazolinyl, imidazolinyl, dioxolanyl, tetrahydrofuranyl, and dihydrofuran-2(3H)-one;
(c20) a non-aromatic heterocyclic ($C_1$-$C_8$) alkyl group selected from the group consisting of pyrrolidinyl, piperidinyl, morpholinyl, thiomorpholinyl, piperadinyl, 4-methyl piperadinyl, oxazolidinyl, thiazolidinyl, imidazolidinyl, oxazolinyl, thiazolinyl, isoxazolinyl, imidazolinyl, dioxolanyl, tetrahydrofuranyl, and dihydrofuran-2(3H)-one, wherein the non-aromatic heterocyclic ($C_1$-$C_8$) alkyl group has, on its ring, one to five substitution group(s) which may be identical or different and selected from (a) halogen atom, (b) cyano group, (c) nitro group, (af) formyl group, (f) ($C_1$-$C_6$) alkyl group and (g) ($C_1$-$C_6$) alkoxy group;
(c21) a phenyl group;
(c22) a phenyl group having, on its ring, one to five substitution group(s) which may be identical or different and selected from (a) halogen atom, (b) cyano group, (c) nitro group, (af) formyl group, (f) ($C_1$-$C_6$) alkyl group, (h) halo ($C_1$-$C_6$) alkyl group, (g) ($C_1$-$C_6$) alkoxy group, (i) halo ($C_1$-$C_6$) alkoxy group, (ag) ($C_3$-$C_6$) cycloalkyl ($C_1$-$C_6$) alkoxy group, (j) ($C_1$-$C_6$) alkyl thio group, (k) halo ($C_1$-$C_6$) alkyl thio group, (l) ($C_1$-$C_6$) alkyl sulfinyl group, (m) halo ($C_1$-$C_6$) alkyl sulfinyl group, (n) ($C_1$-$C_6$) alkyl sulfonyl group and (o) halo ($C_1$-$C_6$) alkyl sulfonyl group;
(c23) a phenyl ($C_1$-$C_8$) alkyl group;
(c24) a phenyl ($C_1$-$C_8$) alkyl group having, on its ring, one to five substitution group(s) which may be identical or different and selected from (a) halogen atom, (b) cyano group, (c) nitro group, (af) formyl group, (f) ($C_1$-$C_6$) alkyl group, (h) halo ($C_1$-$C_6$) alkyl group, (g) ($C_1$-$C_6$) alkoxy group, (i) halo ($C_1$-$C_6$) alkoxy group, (ag) ($C_3$-$C_6$) cycloalkyl ($C_1$-$C_6$) alkoxy group, (j) ($C_1$-$C_6$) alkyl thio group, (k) halo ($C_1$-$C_6$) alkyl thio group, (l) ($C_1$-$C_6$) alkyl sulfinyl group, (m) halo ($C_1$-$C_6$) alkyl sulfinyl group, (n) ($C_1$-$C_6$) alkyl sulfonyl group and (o) halo ($C_1$-$C_6$) alkyl sulfonyl group;
(c25) a phenyl carbonyl ($C_1$-$C_6$) alkyl group;
(c26) a phenyl carbonyl ($C_1$-$C_8$) alkyl group having, on its ring, one to five substitution group(s) which may be identical or different and selected from (a) halogen atom, (b) cyano group, (c) nitro group, (af) formyl group, (f) ($C_1$-$C_6$) alkyl group, (h) halo ($C_1$-$C_6$) alkyl group, (g) ($C_1$-$C_6$) alkoxy group, (i) halo ($C_1$-$C_6$) alkoxy group, (ag) ($C_3$-$C_6$) cycloalkyl ($C_1$-$C_6$) alkoxy group, (j) ($C_1$-$C_6$) alkyl thio group, (k) halo ($C_1$-$C_6$) alkyl thio group, (l) ($C_1$-$C_6$) alkyl sulfinyl group, (m)

halo ($C_1$-$C_6$) alkyl sulfinyl group, (n) ($C_1$-$C_6$) alkyl sulfonyl group and (o) halo ($C_1$-$C_6$) alkyl sulfonyl group;

(c27) an aromatic heterocyclic group selected from the group consisting of pyridyl, pyrimidinyl, pyridadinyl, pyradinyl, triadinyl, thienyl, furanyl, thiazoyl, and oxazoyl;

(c28) an aromatic heterocyclic group selected from the group consisting of pyridyl, pyrimidinyl, pyridadinyl, pyradinyl, triadinyl, thienyl, furanyl, thiazoyl, and oxazoyl, wherein the aromatic heterocyclic group has, on its ring, one to three substitution group(s) which may be identical or different and selected from (a) halogen atom, (b) cyano group, (c) nitro group, (af) formyl group, (f) ($C_1$-$C_6$) alkyl group, (h) halo ($C_1$-$C_6$) alkyl group, (g) ($C_1$-$C_6$) alkoxy group, (i) halo ($C_1$-$C_6$) alkoxy group, (ag) ($C_3$-$C_6$) cycloalkyl ($C_1$-$C_6$) alkoxy group, (j) ($C_1$-$C_6$) alkyl thio group, (k) halo ($C_1$-$C_6$) alkyl thio group, (l) ($C_1$-$C_6$) alkyl sulfinyl group, (m) halo ($C_1$-$C_6$) alkyl sulfinyl group, (n) ($C_1$-$C_6$) alkyl sulfonyl group and (o) halo ($C_1$-$C_6$) alkyl sulfonyl group;

(c29) an aromatic heterocyclic ($C_1$-$C_8$) alkyl group selected from the group consisting of pyridyl, pyrimidinyl, pyridadinyl, pyradinyl, triadinyl, thienyl, furanyl, thiazoyl, and oxazoyl;

(c30) an aromatic heterocyclic ($C_1$-$C_8$) alkyl group selected from the group consisting of pyridyl, pyrimidinyl, pyridadinyl, pyradinyl, triadinyl, thienyl, furanyl, thiazoyl, and oxazoyl wherein the aromatic heterocyclic group has, on its ring, one to three substitution group(s) which may be identical or different and selected from (a) halogen atom, (b) cyano group, (c) nitro group, (af) formyl group, (f) ($C_1$-$C_6$) alkyl group, (h) halo ($C_1$-$C_6$) alkyl group, (g) ($C_1$-$C_6$) alkoxy group, (i) halo ($C_1$-$C_6$) alkoxy group, (ag) ($C_3$-$C_6$) cycloalkyl ($C_1$-$C_6$) alkoxy group, (j) ($C_1$-$C_6$) alkyl thio group, (k) halo ($C_1$-$C_6$) alkyl thio group, (l) ($C_1$-$C_6$) alkyl sulfinyl group, (m) halo ($C_1$-$C_6$) alkyl sulfinyl group, (n) ($C_1$-$C_6$) alkyl sulfonyl group and (o) halo ($C_1$-$C_6$) alkyl sulfonyl group;

(c31) a ($C_1$-$C_8$) alkyl sulfonyl group;

(c32) an amino carbonyl ($C_1$-$C_8$) alkyl group;

(c33) a di (($C_1$-$C_8$) alkyl) amino ($C_1$-$C_8$) alkyl group (in the formula, alkyl in di ($C_1$-$C_8$) alkyl may be identical or different);

(c34) a ($C_1$-$C_8$) alkyl carbonyloxy ($C_1$-$C_8$) alkyl group;

(c35) a di ($C_1$-$C_8$) alkoxy ($C_1$-$C_8$) alkyl group (in the formula, alkyl in di ($C_1$-$C_8$) alkyl may be identical or different, and may be bonded to an identical or different carbon);

(c36) a formyl group;

(c37) a di (($C_1$-$C_8$) alkyl) amino carbonyl group (in the formula, alkyl in di ($C_1$-$C_8$) alkyl may be identical or different);

(c38) a formyl ($C_1$-$C_8$) alkyl group;

(c39) a ($C_1$-$C_8$) alkoxy imino ($C_1$-$C_8$) alkyl group;

(c40) a halo ($C_1$-$C_8$) alkyl thio ($C_1$-$C_8$) alkyl group;

(c41) a halo ($C_1$-$C_8$) alkyl sulfinyl ($C_1$-$C_8$) alkyl group;

(c42) a halo ($C_1$-$C_8$) alkyl sulfonyl ($C_1$-$C_8$) alkyl group;

(c43) a ($C_3$-$C_8$) cycloalkyl ($C_1$-$C_8$) alkyl group; or (c44) a cyano halo ($C_1$-$C_8$) alkyl group;

A represents a CH or C—$R^8$ (in the formula, $R^8$ represents (a) a halogen atom, (b) a cyano group, (c) a nitro group, (af) a formyl group, (f) a ($C_1$-$C_6$) alkyl group, (h) a halo ($C_1$-$C_6$) alkyl group, (g) a ($C_1$-$C_6$) alkoxy group, or (i) a halo ($C_1$-$C_6$) alkoxy group);

Y represents an oxygen atom;

$Y^1$ represents a C=O, C=S or $CH_2$ group; and m represents an integer of 0 or 1.

2. The compound according to claim 1, wherein:

$R^1$, $R^2$, $R^3$ and $R^4$ may be identical or different, representing:

(a1) a hydrogen atom;

(a2) a halogen atom;

(a3) a ($C_1$-$C_8$) alkyl group;

(a10) a phenyl sulfonyl group;

(a11) an amino group; or (a12) a ($C_1$-$C_8$) alkyl carbonyl amino group;

$R^7$ is:

(c1) a hydrogen atom;

(c2) a ($C_1$-$C_{12}$) alkyl group;

(c3) a ($C_2$-$C_8$) alkenyl group;

(c4) a ($C_2$-$C_8$) alkynyl group;

(c5) a cyano ($C_1$-$C_8$) alkyl group;

(c6) a ($C_3$-$C_8$) cycloalkyl group;

(c7) a halo ($C_1$-$C_8$) alkyl group;

(c10) a ($C_1$-$C_8$) alkoxy ($C_1$-$C_8$) alkyl group;

(c11) a ($C_1$-$C_8$) alkyl thio ($C_1$-$C_8$) alkyl group;

(c12) a ($C_1$-$C_8$) alkyl sulfinyl ($C_1$-$C_8$) alkyl group;

(c13) a ($C_1$-$C_8$) alkyl sulfonyl ($C_1$-$C_8$) alkyl group;

(c14) a ($C_1$-$C_8$) alkyl carbonyl group;

(c16) a ($C_1$-$C_8$) alkoxy carbonyl ($C_1$-$C_8$) alkyl group;

(c18) a di (($C_1$-$C_8$) alkyl) amino ($C_1$-$C_8$) alkyl group (in the formula, alkyl in di ($C_1$-$C_8$) alkyl may be identical or different);

(c19) a non-aromatic heterocyclic ($C_1$-$C_8$) alkyl group selected from the group consisting of pyrrolidinyl, piperidinyl, morpholinyl, thiomorpholinyl, piperadinyl, 4-methyl piperadinyl, oxazolidinyl, thiazolidinyl, imidazolidinyl, oxazolinyl, thiazolinyl, isoxazolinyl, imidazolinyl, dioxolanyl, tetrahydrofuranyl, and dihydrofuran-2(3H)-one;

(c20) a non-aromatic heterocyclic ($C_1$-$C_8$) alkyl group selected from the group consisting of pyrrolidinyl, piperidinyl, morpholinyl, thiomorpholinyl, piperadinyl, 4-methyl piperadinyl, oxazolidinyl, thiazolidinyl, imidazolidinyl, oxazolinyl, thiazolinyl, isoxazolinyl, imidazolinyl, dioxolanyl, tetrahydrofuranyl, and dihydrofuran-2(3H)-one, wherein the non-aromatic heterocyclic ($C_1$-$C_8$) alkyl group has, on its ring, one to five substitution group(s) which may be identical or different and selected from (a) halogen atom, (b) cyano group, (c) nitro group, (af) formyl group, (f) ($C_1$-$C_6$) alkyl group and (g) ($C_1$-$C_6$) alkoxy group;

(c21) a phenyl group;

(c23) a phenyl ($C_1$-$C_8$) alkyl group;

(c24) a phenyl ($C_1$-$C_8$) alkyl group having, on its ring, one to five substitution group(s) which may be identical or different and selected from (a) halogen atom, (b) cyano group, (c) nitro group, (af) formyl group, (f) ($C_1$-$C_6$) alkyl group, (h) halo ($C_1$-$C_6$) alkyl group, (g) ($C_1$-$C_6$) alkoxy group, (i) halo ($C_1$-$C_6$) alkoxy group, (ag) ($C_3$-$C_6$) cycloalkyl ($C_1$-$C_6$) alkoxy group, (j) ($C_1$-$C_6$) alkyl thio group, (k) halo ($C_1$-$C_6$) alkyl thio group, (l) ($C_1$-$C_6$) alkyl sulfinyl group, (m) halo ($C_1$-$C_6$) alkyl sulfinyl group, (n) ($C_1$-$C_6$) alkyl sulfonyl group and (o) halo ($C_1$-$C_6$) alkyl sulfonyl group;

(c26) a phenyl carbonyl ($C_1$-$C_8$) alkyl group having, on its ring, one to five substitution group(s) which may be identical or different and selected from (a) halogen atom, (b) cyano group, (c) nitro group, (af) formyl group, (f) ($C_1$-$C_6$) alkyl group, (h) halo ($C_1$-$C_6$) alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group and (o) halo $(C_1-C_6)$ alkyl sulfonyl group;
- (c27) an aromatic heterocyclic group selected from the group consisting of pyridyl, pyrimidinyl, pyridadinyl, pyradinyl, triadinyl, thienyl, furanyl, thiazoyl, and oxazoyl;
- (c29) an aromatic heterocyclic $(C_1-C_8)$ alkyl group selected from the group consisting of pyridyl, pyrimidinyl, pyridadinyl, pyradinyl, triadinyl, thienyl, furanyl, thiazoyl, and oxazoyl;
- (c30) an aromatic heterocyclic $(C_1-C_8)$ alkyl group selected from the group consisting of pyridyl, pyrimidinyl, pyridadinyl, pyradinyl, triadinyl, thienyl, furanyl, thiazoyl, and oxazoyl wherein the aromatic heterocyclic $(C_1-C_8)$ alkyl group has, on its ring, one to three substitution group(s) which may be identical or different and selected from (a) halogen atom, (b) cyano group, (c) nitro group, (af) formyl group, (f) $(C_1-C_6)$ alkyl group, (h) halo $(C_1-C_6)$ alkyl group, (g) $(C_1-C_6)$ alkoxy group, (i) halo $(C_1-C_6)$ alkoxy group, (ag) $(C_3-C_6)$ cycloalkyl $(C_1-C_6)$ alkoxy group, (j) $(C_1-C_6)$ alkyl thio group, (k) halo $(C_1-C_6)$ alkyl thio group, (l) $(C_1-C_6)$ alkyl sulfinyl group, (m) halo $(C_1-C_6)$ alkyl sulfinyl group, (n) $(C_1-C_6)$ alkyl sulfonyl group and (o) halo $(C_1-C_6)$ alkyl sulfonyl group;
- (c31) a $(C_1-C_8)$ alkyl sulfonyl group;
- (c32) an amino carbonyl $(C_1-C_8)$ alkyl group;
- (c33) a di $((C_1-C_8)$ alkyl) amino $(C_1-C_8)$ alkyl group (in the formula, alkyl in di $(C_1-C_8)$ alkyl may be identical or different);
- (c34) a $(C_1-C_8)$ alkyl carbonyloxy $(C_1-C_8)$ alkyl group;
- (c35) a di $(C_1-C_8)$ alkoxy $(C_1-C_8)$ alkyl group (in the formula, alkyl in di $(C_1-C_8)$ alkyl may be identical or different);
- (c36) a formyl group;
- (c37) a di $((C_1-C_8)$ alkyl) amino carbonyl group (in the formula, alkyl in di $(C_1-C_8)$ alkyl may be identical or different);
- (c38) a formyl $(C_1-C_8)$ alkyl group;
- (c39) a $(C_1-C_8)$ alkoxy imino $(C_1-C_8)$ alkyl group;
- (c40) a halo $(C_1-C_8)$ alkyl thio $(C_1-C_8)$ alkyl group;
- (c41) a halo $(C_1-C_8)$ alkyl sulfinyl $(C_1-C_8)$ alkyl group;
- (c42) a halo $(C_1-C_8)$ alkyl sulfonyl $(C_1-C_8)$ alkyl group;
- (c43) a $(C_3-C_8)$ cycloalkyl $(C_1-C_8)$ alkyl group; or
- (c44) a cyano halo $(C_1-C_8)$ alkyl group.

3. The compound according to claim 1, wherein:
$R^1$, $R^2$, $R^3$ and $R^4$ may be identical or different, representing:
- (a1) a hydrogen atom; or
- (a2) a halogen atom;

$R^5$ and $R^6$ form Structural Formula $Q^1$ or $Q^7$ together with carbon atoms to which they are bonded;
$R^7$ is:
- (c1) a hydrogen atom;
- (c2) a $(C_1-C_{12})$ alkyl group;
- (c4) a $(C_2-C_8)$ alkynyl group;
- (c5) a cyano $(C_1-C_8)$ alkyl group; or
- (c10) a $(C_1-C_8)$ alkoxy $(C_1-C_8)$ alkyl group;

A is a CH;
$Y^1$ is a C=O; and
m is 0.

4. An insecticidal composition comprising an effective amount of a compound according to claim 1 or a salt thereof and an agriculturally or horticulturally acceptable carrier.

5. A method of controlling unwanted insects in agriculture or horticulture comprising applying the composition according to claim 4 to plant or soil.

6. The compound according to claim 2, wherein:
$R^1$, $R^2$, $R^3$ and $R^4$ may be identical or different, representing:
- (a1) a hydrogen atom; or
- (a2) a halogen atom;

$R^5$ and $R^6$ form Structural Formula $Q^1$ or $Q^7$ together with a carbon atom bonded to it;
$R^7$ is:
- (c1) a hydrogen atom;
- (c2) a $(C_1-C_{12})$ alkyl group;
- (c4) a $(C_2-C_8)$ alkynyl group;
- (c5) a cyano $(C_1-C_8)$ alkyl group; or
- (c10) a $(C_1-C_8)$ alkoxy $(C_1-C_8)$ alkyl group;

A is a CH;
$Y^1$ is a C=O; and
m is 0.

7. An insecticidal composition comprising an effective amount of a compound according to claim 2 or a salt thereof and an agriculturally or horticulturally acceptable carrier.

8. A method of controlling unwanted insects in agriculture or horticulture comprising applying the composition according to claim 7 to plant or soil.

9. An insecticidal composition comprising an effective amount of a compound according to claim 3 or a salt thereof and an agriculturally or horticulturally acceptable carrier.

10. A method of controlling unwanted insects in agriculture or horticulture comprising applying the composition according to claim 9 to plant or soil.

11. An insecticidal composition comprising an effective amount of a compound according to claim 6 or a salt thereof and an agriculturally or horticulturally acceptable carrier.

12. A method of controlling unwanted insects in agriculture or horticulture comprising applying the composition according to claim 11 to plant or soil.

* * * * *